United States Patent
Paliwal et al.

(10) Patent No.: US 7,902,366 B2
(45) Date of Patent: *Mar. 8, 2011

(54) NK$_1$ ANTAGONISTS

(75) Inventors: Sunil Paliwal, Monroe Township, NJ (US); Gregory A. Reichard, Ann Arbor, MI (US); Cheng Wang, Summit, NJ (US); Dong Xiao, Warren, NJ (US); Hon-Chung Tsui, East Brunswick, NJ (US); Neng-Yang Shih, Warren, NJ (US); Juan D. Arredondo, Montclair, NJ (US); Michelle Laci Wrobleski, Whitehouse Station, NJ (US); Anandan Palani, Bridgewater, NJ (US)

(73) Assignee: OPKO Health, Inc., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/358,827

(22) Filed: Feb. 21, 2006

(65) Prior Publication Data
US 2006/0199815 A1    Sep. 7, 2006

Related U.S. Application Data

(62) Division of application No. 10/321,687, filed on Dec. 17, 2002, now Pat. No. 7,049,320.

(60) Provisional application No. 60/341,452, filed on Dec. 18, 2001.

(51) Int. Cl.
A61K 31/445 (2006.01)
C07D 211/12 (2006.01)

(52) U.S. Cl. .................. 546/192; 514/317

(58) Field of Classification Search .......... 546/180, 546/192; 514/317
See application file for complete search history.

(56) References Cited

U.S. PATENT DOCUMENTS

| | | | |
|---|---|---|---|
| 6,436,928 B1 * | 8/2002 | Shih et al. | 514/227.8 |
| 6,635,639 B2 * | 10/2003 | Arora et al. | 514/234.5 |
| 7,041,682 B2 * | 5/2006 | Shih et al. | 514/326 |
| 7,122,677 B2 * | 10/2006 | Reichard et al. | 548/407 |
| 2006/0094720 A1 * | 5/2006 | Shih et al. | 514/235.2 |
| 2006/0223804 A1 * | 10/2006 | Shah et al. | 514/241 |

FOREIGN PATENT DOCUMENTS

EP    0790 248 A    8/1997

OTHER PUBLICATIONS

Xiujuan Wu et al 2000. , Stereoselective transformation of 2H-1,4-Oxazin-2-ones into 2,(2),5,5-tri- and tetrasubstituted Analogues. . . .*
English translation of Knabe, J., et al., "Racemates and Enantiomers of . . . ," Pharmazie 52(12):912-919 (1997).
English translation of Schult, Karl E., et al., "Hydantoin-Derivate as Potential . . . ," Eur. J. Med. Chem.—Chimica Therapeutics 13(1):25-31 (1978).
Knabe, J., et al., "Racemates and Enantiomers of Basic Substituted 5-Phenylhydantoins . . . ," Pharmazie 52(12): 912-919 (1997).
Oh, Chang-Hyun et al., "Synthesis of New Hydantoin-3-Acetic Acid Derivatives . . . ," Bull. Korean Chem. Soc. 9(4):231-235 (1988).
Shulte, Karl E., et al., "Hydantoin-Derivate als . . . ," Eur. J. Med. Chem.—Chimica Therapeutica 13(1):25-31 (1978).
Wu, X. et al., "Generation of Cyclopenta [c] piperidines and Pyrrolo [3,4-c]piperidines- . . . ," Tetrahedron 56(34): 6279-6290 (2000).

* cited by examiner

Primary Examiner — Rita J Desai

(57) ABSTRACT

A NK$_1$ antagonist having the formula (I),

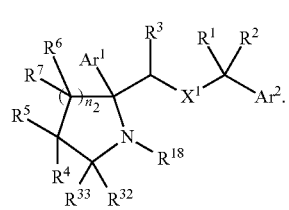

wherein Ar$^1$ and Ar$^2$ are optionally substituted phenyl or heteroaryl, X$^1$ is an ether, thio or imino linkage, R$^4$ and R$^5$ are not both H or alkyl, and the remaining variables are as defined in the specification, useful for treating a number of disorders, including emesis, depression, anxiety and cough. Pharmaceutical compositions. Methods of treatment and combinations with other agents are also disclosed.

19 Claims, No Drawings

NK₁ ANTAGONISTS

RELATED APPLICATIONS

This application is a divisional of application U.S. application Ser. No. 10/321,687, filed Dec. 17, 2002, now allowed and herein incorporated by reference, which in turn claims the benefit under 35 USC 119(e) to provisional application U.S. application Ser. No. 60/341,452, filed Dec. 18, 2001.

CROSS REFERENCE TO RELATED APPLICATION

This application claims the benefit of U.S. Provisional Application 60/341,452, filed Dec. 18, 2001.

BACKGROUND OF THE INVENTION

1. Field of the Invention

The invention relates to an antagonist of the neuropeptide neurokinin-1 ($NK_1$ or NK-1) receptor.

2. Description of Related Art

Tachykinins are peptide ligands for neurokinin receptors. Neurokinin receptors, such as $NK_1$, $NK_2$ and $NK_3$, are involved in a variety of biological processes. They can be found in a mammal's nervous and circulatory systems, as well as in peripheral tissues. Consequently, the modulation of these types of receptors have been studied to potentially treat or prevent various mammalian disease states. For instance, $NK_1$ receptors have been reported to be involved in microvascular leakage and mucus secretion. Representative types of neurokinin receptor antagonists and their uses can be found in: U.S. Pat. No. 5,760,018 (1998) (pain, inflammation, migraine and emesis), U.S. Pat. No. 5,620,989 (1997) (pain, nociception and inflammation), WO 95/19344 (1995) (same), WO 94/13639 (1994) (same) and WO 94/10165 (1994) (same). Further types of $NK_1$ receptor antagonists can be found in Wu et al, *Tetrahedron* 56, 3043-3051 (2000); Rombouts et al, *Tetrahedron Letters* 42, 7397-7399 (2001); and Rogiers et al, *Tetrahedron* 57, 8971-8981 (2001).

It would be beneficial to provide a $NK_1$ antagonist that is potent, selective, and possesses beneficial therapeutic and pharmacological properties, and good metabolic stability. It would further be beneficial to provide a $NK_1$ antagonist that is effective for treating a variety of physiological disorders, symptoms and diseases while minimizing side effects. The invention seeks to provide these and other benefits, which will become apparent as the description progresses.

SUMMARY OF THE INVENTION

In one aspect of the invention, a compound is provided having the formula (I):

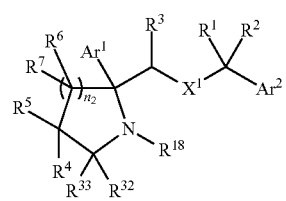

(I)

or a pharmaceutically-acceptable salt thereof, wherein $Ar^1$ and $Ar^2$ are each independently selected from the group consisting of $R^{17}$-heteroaryl and

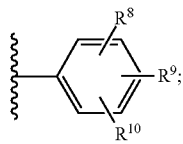

$X^1$ is —O—, —S—, —SO—, —$SO_2$—, —$NR^{34}$—, —N($COR^{12}$)— or —N($SO_2R^{15}$)—;

when $X^1$ is —SO—, —$SO_2$—, —N($COR^{12}$)— or —N($SO_2R^{15}$)—, then:

$R^1$ and $R^2$ are each independently selected from the group consisting of H, $C_1$-$C_6$ alkyl, hydroxy($C_1$-$C_3$alkyl), $C_3$-$C_8$ cycloalkyl, —$CH_2F$, —$CHF_2$ and —$CF_3$; or $R^1$ and $R^2$, together with the carbon atom to which they are both attached, form a chemically feasible $C_3$ to $C_6$ alkylene ring; or when $X^1$ is —O—, —S— or —$NR^{34}$—, then:

$R^1$ and $R^2$ are each independently selected from the group consisting of H, $C_1$-$C_6$ alkyl, hydroxy($C_1$-$C_3$alkyl), $C_3$-$C_8$ cycloalkyl, —$CH_2F$, —$CHF_2$ and —$CF_3$; or $R^1$ and $R^2$, together with the carbon atom to which they are both attached, form a chemically feasible $C_3$ to $C_6$ alkylene ring; or $R^1$ and $R^2$, together with one another and the carbon atom to which they are both attached, form a C=O group;

$R^3$ is selected from the group consisting of H, $C_1$-$C_6$ alkyl, hydroxy($C_1$-$C_3$ alkyl), $C_3$-$C_8$ cycloalkyl, —$CH_2F$, —$CHF_2$ and —$CF_3$;

each $R^6$ is independently selected from the group consisting of H, $C_1$-$C_6$ alkyl and —OH;

each $R^7$ is independently selected from the group consisting of H and $C_1$-$C_6$ alkyl;

$n_2$ is 1 to 4;

$R^4$ and $R^5$ are each independently selected from the group consisting of —($CR^{28}R^{29})_{n1}$-G, where, $n_1$ is 0 to 5; and G is H, —$CF_3$, —$CHF_2$, —$CH_2F$, —OH, —O—($C_1$-$C_6$ alkyl), —$OCH_2F$, —$OCHF_2$, —$OCF_3$, —$OCH_2CF_3$, —O—($C_3$-$C_8$ cycloalkyl), —O—($C_1$-$C_6$)alkyl($C_3$-$C_8$ cycloalkyl), —$NR^{13}R^{14}$, —$SO_2NR^{13}R^{14}$, —$NR^{12}SO_2R^{13}$, —$NR^{12}C(O)R^{14}$, —$NR^{12}C(O)O^{13}$, —$NR^{12}(C(O)NR^{13}R^{14})$, —$C(O)NR^{13}R^{14}$, —C(O)$OR^{13}$, —$C_3$-$C_8$ cycloalkyl, $(R^{19})_r$-aryl, $(R^{19})$r-heteroaryl, —$OC(O)R^{14}$, —$OC(O)NR^{13}R^{14}$, —C(=$NOR^{14}$)($R^{13}$), —C(O)$R^{13}$, —C($OR^{12}$)($R^{13}$)($R^{14}$), heterocycloalkenyl optionally substituted by 1 to 4 substituents independently selected from the group consisting of $R^{30}$ and $R^{31}$,

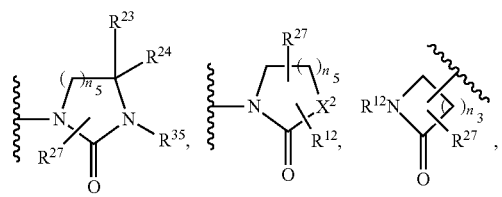

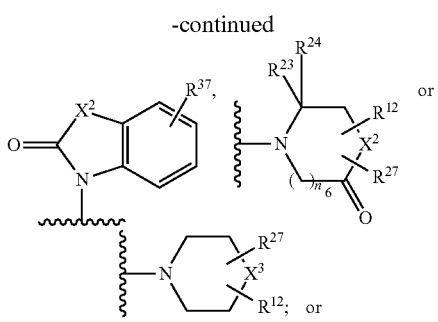

$R^4$ and $R^5$ together are =O, =NOR$^{12}$; or $R^4$ and $R^5$, together with the carbon atom to which they are both attached, form a chemically feasible 4- to 8-membered heterocycloalkyl or heterocycloalkenyl ring containing 1 to 3 groups independently selected from $X^2$, provided that at least one $X^2$ is —NR$^{35}$—, —O—, —S—, —S(O)— or —SO$_2$—, the chemically feasible ring being optionally substituted with from 1 to 6 substituents independently selected from the group consisting of R$^{30}$ and R$^{31}$;

provided that R$^4$ and R$^5$ are not both selected from the group consisting of H, alkyl and cycloalkyl;

further provided that, when one of R$^4$ and R$^5$ is —OH, then the other one of R$^4$ and R$^5$ is not alkyl or (R$^{19}$)$_r$-aryl;

R$^8$, R$^9$ and R$^{10}$ are each independently selected from the group consisting of H, C$_1$-C$_6$ alkyl, C$_3$-C$_8$ cycloalkyl, —OR$^{12}$, halogen, —CN, —NO$_2$, —CF$_3$, —CHF$_2$, —CH$_2$F, —CH$_2$CF$_3$, —OCF$_3$, —OCHF$_2$, —OCH$_2$F, —OCH$_2$CF$_3$, —COOR$^{12}$, —CONR$^{21}$R$^{22}$, —OC(O)NR$^{21}$R$^{22}$, —OC(O)R$^{12}$, —NR$^{21}$COR$^{12}$, —NR$^{21}$CO$_2$R$^{15}$, —NR$^{21}$CONR$^{21}$R$^{22}$, —NR$^{21}$SO$_2$R$^{15}$, —NR$^{21}$R$^{22}$, —SO$_2$NR$^{21}$R$^{22}$, —S(O)$_{n6}$R$^{15}$, (R$^{19}$)$_r$-aryl and (R$^{19}$)$_r$-heteroaryl:

R$^{12}$ is H, C$_1$-C$_6$ alkyl or C$_3$-C$_8$ cycloalkyl;

R$^{13}$ and R$^{14}$ are each independently selected from the group consisting of H, C$_1$-C$_6$ alkyl, C$_3$-C$_8$ cycloalkyl, (C$_3$-C$_8$)cycloalkyl(C$_1$-C$_6$)alkyl, —CH$_2$CF$_3$, aryl and heteroaryl; or R$^{13}$ and R$^{14}$, together with the nitrogen atom to which they are both attached, form a chemically feasible 4- to 7-membered saturated or unsaturated ring that is optionally substituted with —OR$^{12}$, where one of the carbon atoms in the ring is optionally replaced by a heteroatom selected from the group consisting of —O—, —S— and —NR$^{34}$—;

n$_6$ is 0, 1 or 2;

R$^{15}$ is C$_1$-C$_6$ alkyl, C$_3$-C8 cycloalkyl, —CF$_3$ or —CH$_2$CF$_3$;

R$^{18}$ is H, C$_1$-C$_6$ alkyl, C$_3$-C$_8$ cycloalkyl, (C$_3$-C$_8$)cycloalkyl(C$_1$-C$_6$)alkyl, hydroxy(C$_2$-C$_6$)alkyl or —P(O)(OH)$_2$;

each R$^{19}$ is a substituent on the aryl or heteroaryl ring to which it is attached, and is independently selected from the group consisting of H, C$_1$-C$_6$ alkyl, C$_3$-C$_8$ cycloalkyl, C$_1$-C$_6$ alkoxy, —OH, halogen, —CN, —NO$_2$, —CF$_3$, —CHF$_2$, —CH$_2$F, —OCF$_3$, —OCHF$_2$, —OCH$_2$F, —O—(C$_1$-C$_6$ alkyl), —O—(C$_3$-C$_8$ cycloalkyl), —COOR$^{12}$, —CONR$^{21}$R$^{22}$, —OC(O)NR$^{21}$R$^{22}$, —OC(O)R$^{12}$, —NR$^{21}$R$^{22}$, —NR$^{21}$COR$^{12}$, —NR$^{21}$CO$_2$R$^{12}$, —NR$^{21}$CONR$^{21}$R$^{22}$, —NR$^{21}$SO$_2$R$^{15}$ and —S(O)$_{n6}$R$^{15}$;

R$^{21}$ and R$^{22}$ are each independently selected from the group consisting of H, C$_1$-C$_6$ alkyl, C$_3$-C$_8$ cycloalkyl and benzyl; or R$^{21}$ and R$^{22}$, together with the nitrogen atom to which they are both attached, form a chemically feasible 4- to 7-membered saturated or unsaturated ring, where one of the carbon atoms in the ring is optionally replaced by a heteroatom selected from the group consisting of —O—, —S— and —NR$^{34}$—;

R$^{23}$ and R$^{24}$ are each independently selected from the group consisting of H and C$_1$-C$_6$ alkyl; or R$^{23}$ and R$^{24}$, together with the carbon atom to which they are both attached, form a C=O or cyclopropyl group;

R$^{27}$ is H, —OH or C$_1$-C$_6$ alkyl;

R$^{28}$ and R$^{29}$ are each independently selected from the group consisting of H and C$_1$-C$_2$ alkyl;

R$^{30}$ and R$^{31}$ are each independently selected from the group consisting of H, —OH, C$_1$-C$_6$alkyl, C$_3$-C$_8$ cycloalkyl, (C$_3$-C$_8$)cycloalkyl(C$_1$-C$_6$)alkyl and —C(O)NR$^{13}$R$^{14}$; or R$^{30}$ and R$^{31}$, together with the carbon atom to which they are both attached, form =O, =S, a cyclopropyl ring or =NR$^{36}$;

R$^{32}$ and R$^{33}$ are each independently selected from the group consisting of H and C$_1$-C$_6$ alkyl;

R$^{34}$ is H, C$_1$-C$_6$ alkyl, C$_3$-C$_8$ cycloalkyl, (C$_3$-C$_8$)cycloalkyl(C$_1$-C$_6$)alkyl or hydroxy(C$_2$-C$_6$)alkyl;

R$^{35}$ is H, C$_1$-C$_6$ alkyl, C$_3$-C$_8$ cycloalkyl, (C$_3$-C$_8$)cycloalkyl(C$_1$-C$_6$)alkyl, —P(O)(OH)$_2$, allyl, hydroxy(C$_2$-C$_6$)alkyl, (C$_1$-C$_6$)alkoxy(C$_1$-C$_6$)alkyl, —SO$_2$R$^{15}$, or —(CH$_2$)$_2$—N(R$^{12}$)—SO$_2$—R$^{15}$;

R$^{36}$ is H, C$_1$-C$_6$ alkyl, C$_3$-C$_8$ cycloalkyl, (C$_3$-C$_8$)cycloalkyl(C$_1$-C$_6$)alkyl, —NO$_2$, —CN or OR$^{12}$;

R$^{37}$ is 1 to 3 substituents independently selected from the group consisting of H, C$_1$-C$_6$ alkyl, —OH, C$_1$-C$_6$ alkoxy and halogen;

r is 1 to 3;

$X^2$ is —NR$^{35}$—, —O—, —S—, —S(O)—, —SO$_2$—, —CH$_2$—, —CF$_2$— or —CR$^{12}$F—;

$X^3$ is —NR$^{34}$—, —N(CONR$^{13}$R$^{14}$)—, —N(CO$_2$R$^{13}$)—, —N(SO$_2$R$^{15}$)—, —N(COR$^{12}$)—, —N(SO$_2$NHR)—, —O—, —S—, —S(O)—, —SO$_2$—, —CH$_2$—, —CF$_2$— or —CR$^{12}$F—;

n$_3$ is 1 to 5; and n$_5$ is 1 to 3.

The invention comprises at least one compound having the formula (I), including any and all diastereomers, enantiomers, stereoisomers, regiostereomers, rotomers, tautomers and prodrugs of the compounds having the formula (I) and their corresponding salts, solvates (e.g., hydrates), esters, and the like. The compounds having the formula (I) can be useful for treating a variety of diseases, symptoms and physiological disorders, such as emesis, depression, anxiety and cough.

Another aspect of the invention comprises a pharmaceutical composition comprising a compound of formula (I), alone or with another active agent, and a pharmaceutically acceptable carrier or excipient therefor. The inventive compounds and compositions can be used alone or in combination with other active agents and/or methods of treatment for treating a variety of diseases, symptoms and physiological disorders, such as the ones disclosed herein.

DETAILED DESCRIPTION

The following definitions and terms are used herein or are otherwise known to a skilled artisan. Except where stated otherwise, the following definitions apply throughout the specification and claims. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

The term "substituted," as used herein, means the replacement of one or more atoms, usually hydrogen atoms, in a given structure with an atom or radical selected from a specified group. In the situations where more than one atom may be replaced with a substituent selected from the same specified group, the substituents may be, unless otherwise specified, either the same or different at every position.

The term "heteroatom," as used herein, means a nitrogen, sulfur, or oxygen atom. Multiple heteroatoms in the same group may be the same or different.

The term "alkyl," as used herein, means a straight or branched, hydrocarbon chain having the designated number of carbon atoms. If the number of carbon atoms is not designated, the carbon chain is from one to twenty-four carbon atoms, more preferably, from one to twelve carbon atoms, and most preferably, from one to six carbon atoms.

The term "cycloalkyl" as used herein, means a saturated, stable, non-aromatic carbocyclic ring having from three to eight carbon atoms. The cycloalkyl may be attached at any endocyclic carbon atom that results in a stable structure. Preferred carbocyclic rings have from three to six carbons. Examples of cycloalkyl radicals include cyclopropyl, cyclobutyl, cyclopentyl, cyclohexyl, cycloheptyl, and the like.

The term "aryl," as used herein, means an aromatic, mono- or bicyclic, carbocyclic ring system having from one to two aromatic rings. The aryl moiety will generally have from 6 to 14 carbon atoms with all available substitutable carbon atoms of the aryl moiety being intended as possible points of attachment. Representative examples include phenyl, cumenyl, naphthyl, tetrahydronaphthyl, indanyl, indenyl and the like.

The term "heteroaryl," as used herein, means a mono- or bicyclic, chemically feasible ring system containing one or two aromatic rings and 1 to 4 nitrogen, oxygen or sulfur atoms in the aromatic ring. Typically, a heteroaryl group represents a cyclic group of five or six atoms, or a bicyclic group of nine or ten atoms, at least one of which is carbon, and having at least one oxygen, sulfur or nitrogen atom interrupting a carbocyclic ring having a sufficient number of pi (,) electrons to provide aromatic character. Representative heteroaryl (heteroaromatic) groups are pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazolyl, tetrazolyl, isothiazolyl, benzothiazolyl, benzoxazolyl, oxazolyl, pyrrolyl, isoxazolyl, 1,3,5-triazinyl and indolyl groups. The heteroaryl group can be joined to the rest of the molecule through a bond at any substitutable carbon or nitrogen.

The term "heterocycloalkyl" as used herein means a saturated cyclic ring having from 3 to 8 members, preferably 5 or 6 members, and comprising 2 to 7 carbon atoms and 1 to 3 heteroatoms independently selected from the group consisting of —O—, —S—, —S(O)—, —SO$_2$— and —NR$^{35}$—. Typical heterocycloalkyl rings are pyrrolidinyl, imidazolidinyl, piperidinyl, piperazinyl, morpholinyl, and the like. The heterocycloclkyl ring can be attached to the rest of the structure through either a substitutable ring carbon or a substitutable ring nitrogen.

The term "heterocycloalkenyl" as used herein means a cyclic ring having from 3 to 8 members, preferably 5 or 6 members, and comprising 2 to 7 carbon atoms and 1 to 3 heteroatoms independently selected from the group consisting of —O—, —S—, —S(O)—, —SO$_2$— and —NR$^{35}$—, and having at least one double bond in the ring, but not having aromatic characteristics. Examples of such rings are:

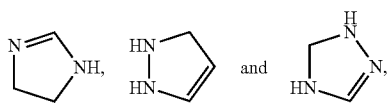

wherein the ring can be attached to the rest of the structure through either a substitutable ring carbon or a substitutable ring nitrogen (e.g., in R$^4$, when G is heterocycloalkenyl, it can be joined to the (CR$^{28}$R$^{29}$)$_{n1}$ group through either a substitutable ring carbon or a substitutable ring nitrogen).

When R$^4$ and R$^5$ form a ring with 1, 2 or 3 groups independently selected from X$^2$, and 1 or 2 of X$^2$ are carbon, the variable size of the ring can be defined by n$_4$ and n$_7$, which are independently selected from 0-5, provided that the sum of n$_4$ and n$_7$ is 1 to 5. A typical structure wherein the heteroatom is —NR$^{35}$—, X$^2$ is —CH$_2$—, and R$^{30}$ and R$^{31}$ together form a carbonyl group is represented by the formula

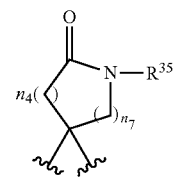

When R$^4$ and R$^5$, together with the carbon to which they are attached, form a heterocycloalkenyl ring, examples of such rings are

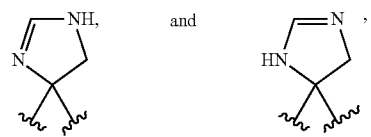

The term "alkoxy," as used herein, means an oxygen atom bonded to a hydrocarbon chain, such as an alkyl or alkenyl group (e.g., —O-alkyl or —O-alkenyl). Representative alkoxy groups include methoxy, ethoxy, and isopropoxy groups.

The term "hydroxyalkyl," as used herein, means a substituted hydrocarbon chain, preferably, an alkyl group, having at least one hydroxy substituent (i.e., —OH). Representative hydroxyalkyl groups include hydroxymethyl, hydroxyethyl and hydroxypropyl groups.

The term "halo" or "halogen" as used herein means a chloro, bromo, fluoro or iodo atom radical.

Unless otherwise known, stated or shown to be to the contrary, the point of attachment for a multiple term substituent (multiple terms that are combined to identify a single moiety) to a subject structure is through the last named term of the multiple term. For example, an "arylalkyl" substituent attaches to a targeted structure through the "alkyl" portion of the substituent. Conversely, when the substituent is "alkylaryl", it attaches to a targeted structure through the "aryl" portion of the substituent. Similarly, a cycloalkylalkyl substituent attaches to a targeted through the latter "alkyl" portion of the substituent (e.g., Structure-alkyl-cycloalkyl).

When a variable appears more than once in a structural formula, for example, R$^8$, its definition at each occurrence is independent of its definition at every other occurrence.

The term "prodrug," as used herein, represents compounds that are drug precursors which, following administration to a patient, release the drug in vivo via a chemical or physiological process (e.g., a prodrug on being brought to a physiological pH or through an enzyme action is converted to the desired drug form). A discussion of prodrugs is provided in T. Higuchi and V. Stella, *Pro-drugs as Novel Delivery Systems*, Vol. 14 of A.C.S. Symposium Series (1987), and in *Bioreversible Carriers in Drug Design*, E. B. Roche, ed., American Pharmaceutical Association and Pergamon Press (1987), each of which is incorporated herein by reference in its entirety.

As used herein, the term "composition" is intended to encompass a product comprising the specified ingredients in the specified amounts, as well as any product which results, directly or indirectly, from combination of the specified ingredients in the specified amounts.

Other than as shown in the operating examples or where is otherwise indicated, all numbers used in the specification and claims expressing quantities of ingredients, reaction conditions, and so forth, are understood as being modified in all instances by the term "about."

Referring to the compound having the formula (I):

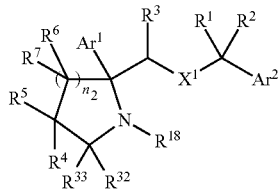

or a pharmaceutically-acceptable salt thereof, preferred are compounds wherein
$Ar^1$ and $Ar^2$ are each, preferably,

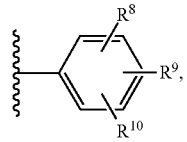

where $R^8$, $R^9$ and $R^{10}$ are each independently defined as above in the summary of the invention. More preferably, for $Ar^2$, $R^{10}$ is H, and $R^8$ and $R^9$ are independently selected from the group consisting of —$CF_3$, —$CHF_2$, —$CH_2F$, halogen, $C_1$-$C_6$ alkyl, —$OCF_3$ and —$OR^{12}$; for $Ar^1$, $R^9$ and $R^{10}$ are independently selected from the group consisting of H, —OH and halogen. The variable $n_2$ is preferably 1 or 2.

$X^1$ is, preferably —O— or —$NR^{34}$—. More preferably, $X^1$ is —O—.

$R^1$ and $R^2$ are each, preferably, independently selected from the group consisting of H and $C_1$-$C_6$ alkyl. More preferably, $R^1$ and $R^2$ are each independently selected from the group consisting of H and $CH_3$.

$R^3$ is preferably selected from the group consisting of H and $C_1$-$C_6$ alkyl. More preferably, $R^3$ is H.

Each $R^6$ is preferably independently selected from the group consisting of H and $C_1$-$C_6$ alkyl. Even more preferably, each $R^6$ is H.

Each $R^7$ is preferably independently selected from the group consisting of H and $C_1$-$C_6$ alkyl. Even more preferably, each $R^7$ is H.

More preferred are compounds of the structure II

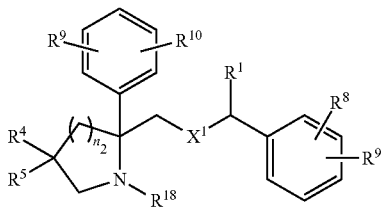

wherein $X^1$ is —O— or —$NR^{34}$—; $R^8$ and $R^9$ are independently selected from the group consisting of —$CF_3$, —$CHF_2$, —$CH_2F$, halogen, $C_1$-$C_6$ alkyl, —$OCF_3$ and —$OR^{12}$; $R^9$ and $R^{10}$ are independently selected from the group consisting of H, —OH and halogen; and $n_2$ is 1 or 2.

Preferred compounds of formula I and formula II are those wherein one of $R^4$ and $R^5$ is H and the other is —$C(R^{28}R^{29})_{n_1}$-G, wherein $n_1$ is 0, 1 or 2. More preferred are compounds wherein one of $R^4$ and $R^5$ is H and the other is selected from the group consisting of —$NR^{13}R^{14}$, —$NR^{12}C(O)R^{14}$, —$C(O)NR^{13}R^{14}$, —$OC(O)R^{14}$, —$OC(O)NR^{13}R^{14}$, $NR^{12}C(O)OR^{13}$, —$C(O)OR^{13}$, —$NR^{12}(C(O)NR^{13}R^{14})$, —$NR^{12}SO_2R^{13}$, —$SO_2NR^{13}R^{14}$, $R^{19}$-heteroaryl,

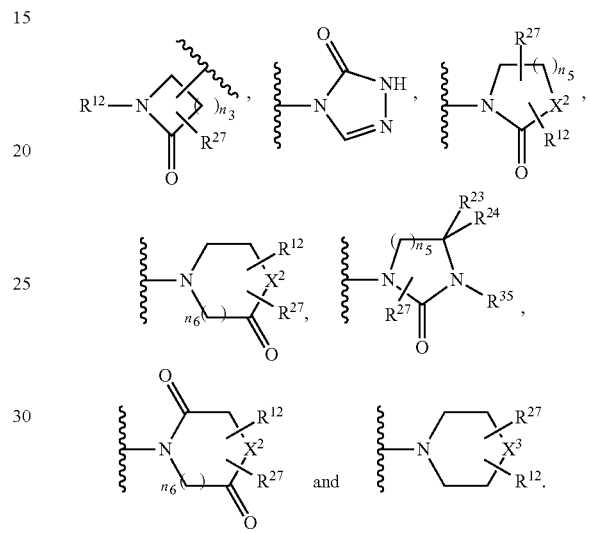

Even more preferred are such compounds wherein $R^{12}$ and $R^{27}$ are independently selected from the group consisting of H and $C_1$-$C_6$ alkyl, especially H and —$CH_3$, and more especially, both are H; $n_3$ is 2 or 3; and $n_5$ is 1 or 2.

In another embodiment, preferred compounds of formula I and formula II are those wherein $R^4$ is —$NR^{13}R^{14}$, —$NR^{12}C(O)R^{14}$, $NR^{12}C(O)OR^{13}$, —$NR^{12}(C(O)NR^{13}R^{14})$, —OH, —O—($C_1$-$C_6$)alkyl, —O—($C_3$-$C_8$)cycloalkyl, —OC(O)$R^{14}$, —OC(O)$NR^{13}R^{14}$, —$NR^{12}SO_2R^{13}$, —$SO_2NR^{13}R^{14}$, $R^{19}$-heteroaryl,

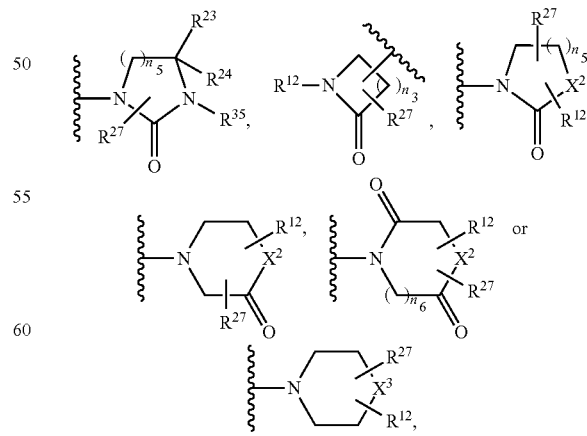

wherein $X_2$ is —O—, —S—, —$CH_2$— or —$NR^{35}$—; and $R^5$ is —$C(O)OR^{13}$ or —$C(O)NR^{13}R^{14}$. More preferred are compounds wherein $R^{12}$ is independently selected from the group consisting of H, $C_1$-$C_6$ alkyl and $C_3$-$C_8$ cycloalkyl; $R^{27}$ is H; $n_3$ is 2 or 3; and $n_5$ is 1 or 2.

Still another preferred embodiment of compounds of formula I and II is that wherein $R^4$ and $R^5$, together with the carbon atom to which they are both attached, form a 4- to 8-membered heterocycloalkyl or heterocycloalkenyl ring containing 1 to 3 groups independently selected from $X^2$, provided that at least one $X^2$ is —$NR^{35}$—, —O—, —S—, —S(O)— or —$SO_2$—, the ring being optionally substituted with from 1 to 6 substituents independently selected from the group consisting of $R^{30}$ and $R^{31}$;. More preferred are compounds wherein the 4- to 8-membered ring is selected from the group consisting of:

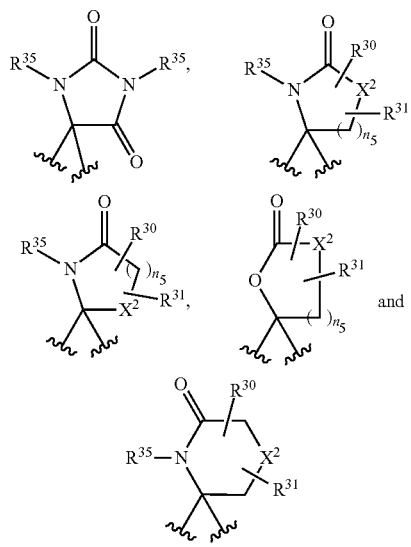

wherein $R^{35}$ is H, $C_1$-$C_6$ alkyl, $C_3$-$C_8$ cycloalkyl, $(C_3$-$C_8)$ cycloalkyl$(C_1$-$C_6)$alkyl or hydroxy$(C_1$-$C_6)$alkyl; $n_5$ is 1, 2 or 3; $X^2$ is —$NR^{35}$—, —$CH_2$—, —O— or —S—; $R^{30}$ is H, $C_1$-$C_6$ alkyl or $C_3$-$C_8$ cycloalkyl; and $R^{31}$ is H, —OH or $C_1$-$C_6$ alkyl. Especially preferred are 4- to 8-membered rings selected from the group consisting of

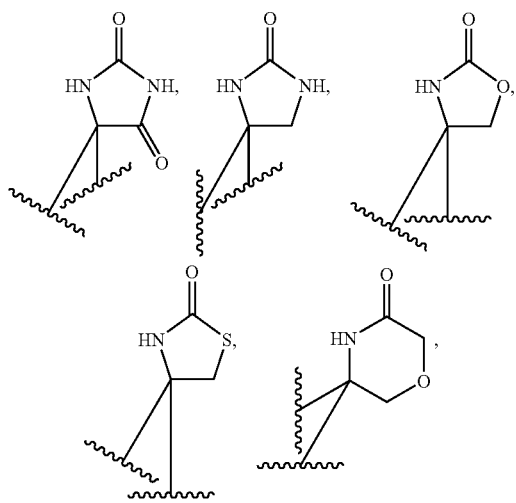

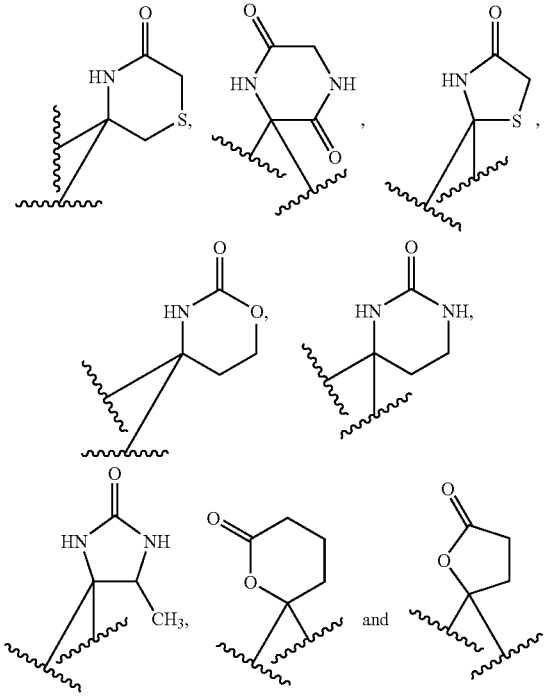

The rings are optionally substituted with $R^{30}$ and $R^{31}$.

Yet another group of preferred compounds wherein $R^4$ and $R^5$ form a ring is that wherein the ring is selected from the group consisting of

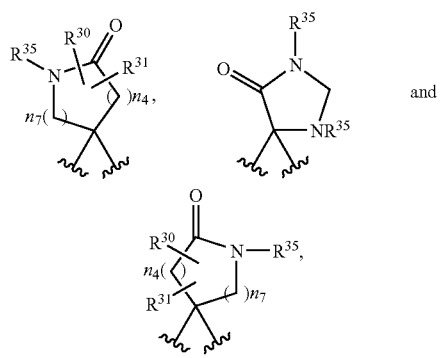

wherein $R^{30}$ is H, $C_1$-$C_6$ alkyl or $C_3$-$C_8$ cycloalkyl; $R^{31}$ is H, —OH or $C_1$-$C_6$ alkyl; each $R^{35}$ is independently selected from the group consisting of H, $C_1$-$C_6$ alkyl, $C_3$-$C_8$ cycloalkyl, $(C_3$-$C_8)$cycloalkyl$(C_1$-$C_6)$alkyl and hydroxy$(C_1$-$C_6)$alkyl; $n_4$ and $n_7$ are independently 0-5, provided that the sum of $n_4$ and $n_7$ is 1-5. Especially preferred are 4- to 8-membered rings selected from the group consisting of

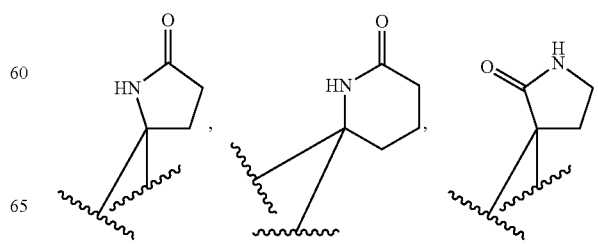

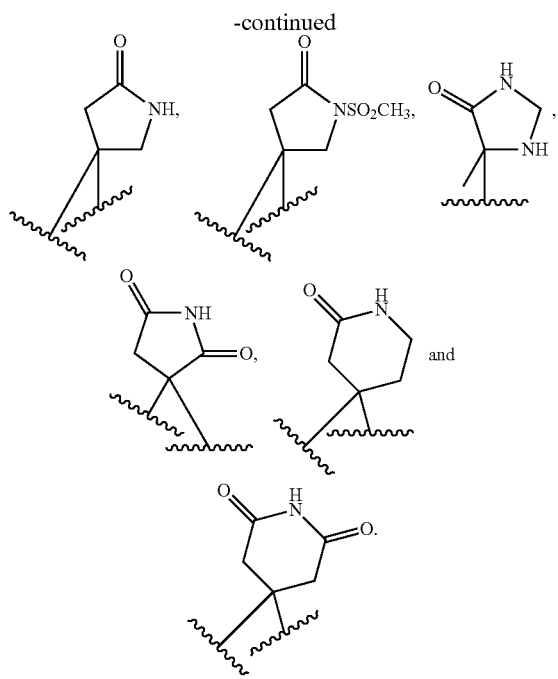

The rings are optionally substituted with $R^{30}$ and $R^{31}$.

In still another embodiment of the invention, it is preferable for at least one of $R^4$ and $R^5$ to be in a cis orientation to the $Ar^1$ substituent.

$R^{15}$ is preferably $C_1$-$C_6$ alkyl or —$CF_3$. More preferably, $R^{15}$ is $C_1$-$C_6$ alkyl.

$R^{18}$ is preferably H or —$C_1$-$C_6$ alkyl. More preferably, $R^{18}$ is H or $CH_3$. Even more preferably, $R^{18}$ is H.

Each $R^{19}$ is a substituent on the aryl or heteroaryl ring to which it is attached, and is, preferably, independently selected from the group consisting of H, $C_1$-$C_6$ alkyl, —$CF_3$, —$CHF_2$, —$CH_2F$, —$OCF_3$, —$OCHF_2$ and —$OCH_2F$. More preferably, each $R^{19}$ is selected from the group consisting of H and $C_1$-$C_6$ alkyl.

Preferably, r is 1 or 2. More preferably, r is 1.

$R^{21}$ and $R^{22}$ are each, preferably, independently selected from the group consisting of H and $C_1$-$C_6$ alkyl. More preferably, $R^{21}$ and $R^{22}$ are each independently selected from the group H and $CH_3$.

$R^{23}$ and $R^{24}$ are each, preferably, independently selected from the group consisting of H and $C_1$-$C_6$ alky, or $R^{23}$ and $R^{24}$ together are =O. More preferably, $R^{23}$ and $R^{24}$ are each independently selected from the group H and $CH_3$.

$R^{28}$ and $R^{29}$ are preferably, independently selected from the group consisting of H and —$CH_3$.

$R^{30}$ and $R^{31}$ are preferably independently selected from the group consisting of H and $C_1$-$C_2$ alkyl, or $R^{30}$ and $R^{31}$ together are =O. More preferably, $R^{30}$ and $R^{31}$ are each independently selected from the group consisting of H and —$CH_3$.

$R^{32}$ and $R^{33}$ are preferably independently selected from the group consisting of H and —$CH_3$ Even more preferably, $R^{32}$ and $R^{33}$ are each H.

$R^{36}$ is preferably H or $C_1$-$C_6$ alkyl. More preferably, $R^{36}$ is H or —$CH_3$.

$R^{37}$ is preferably 1 or 2 substituents selected from the group consisting of H, —$CH_3$ and halogen.

Preferred compounds of the invention are those shown below in Examples 3, 9, 12a, 13, 14, 15, 20, 23, 29, 36, 40, 43b, 44b, 45, 50, 53, 56b, 57, 60a, 61, 62, 63, 72a, 73b, 74a, 75b, 76a, 82a, 82b, 90, 96, 105, 106b, 109, 110a, 111a, 112 and 113. More preferred are compounds of Examples 12a, 43b, 72a, 73b, 109, 110a and 111a.

Compounds having the formula (I) can be effective antagonists of the $NK_1$ receptor, and of an effect of its endogenous agonist, Substance P, at the $NK_1$ receptor site, and therefore, can be useful in treating conditions caused or aggravated by the activity of said receptor. The in vitro and in vivo $NK_1$, $NK_2$ and $NK_3$ activities of the compounds having the formula (I) can be determined by various procedures known in the art, such as a test for their ability to inhibit the activity of the $NK_1$ agonist Substance P. The percent inhibition of neurokinin agonist activity is the difference between the percent of maximum specific binding ("MSB") and 100%. The percent of MSB is defined by the following equation, wherein "dpm" represents "disintegrations per minute":

$$\% \ MSB = \frac{(dpm \ \text{of unknown}) - (dpm \ \text{of nonspecific binding})}{(dpm \ \text{of total binding}) - (dpm \ \text{of nonspecific binding})} \times 100.$$

The concentration at which the compound produces 50% inhibition of binding is then used to determine an inhibition constant ("Ki") using the Chang-Prusoff equation.

In vivo activity may be measured by inhibition of an agonist-induced foot tapping in a gerbil, as descibed in *Science*, 281, 1640-1695 (1998), which is herein incorporated by reference in its entirety. It will be recognized that compounds having the formula (I) can exhibit $NK_1$ antagonist activities of varying degrees. For instance, certain compounds can exhibit stronger $NK_1$ antagonist activities than others.

The compounds of the invention exhibit potent affinities for the $NK_1$ receptor as measured by Ki values (in nM). The activities (potencies) for the compounds of the invention are determined by measuring their Ki values. The smaller the Ki value, the more active is a compound for antagonizing the $NK_1$ receptor. Compounds of the invention exhibit a wide range of activities. The $NK_1$ average Ki values for compounds having the formula (I) generally range from 0.01 nM to about 1000 nM, preferably, from about 0.01 nM to about 500 nM, with values of from about 0.01 nM to about 100 nM being more preferred. Even more preferred are compounds having average Ki values of from 0.01 nM to about 10 nM for the $NK_1$ receptor. The most preferred compounds have $NK_1$ average Ki values of from 0.01 nM to about 3 nM. The preferred compounds noted above have the following Ki values: Example 43b: 0.77 nM; 72a: 0.66 nM; 73b: 0.2 nM; 109: 0.1 nM; 110a: 0.41 nM; and 111a: 0.38 nM.

The inventive compounds are also highly selective for antagonizing a $NK_1$ receptor as opposed to antagonizing (i) $NK_2$ and/or (ii) $NK_3$ receptors. When a compound's selection ratio is greater than about 100 for the Ki of the $NK_1$ receptor to the Ki of the $NK_2$ receptor, and/or, independently, the Ki of the $NK_3$ receptor, then the compound is defined herein as a selective antagonist of the $NK_1$ receptor, as opposed to the $NK_2$ and/or $NK_3$ receptors, respectively.

Compounds having the formula (I) may have at least one asymmetrical carbon atom. All isomers, including stereoisomers, diastereomers, enantiomers, regiostereomers, tautomers and rotational isomers, are contemplated as being part of the invention. Prodrugs, salts, solvates, esters, etc., derived from the compounds having the formula (I) or precursors thereof are also within the scope of the invention. The invention includes d- and l-isomers in pure form and in admixture, including racemic mixtures. Isomers can be prepared using conventional techniques, either by reacting optically pure or optically enriched starting materials or by separating isomers of a compound having the formula (I). Those skilled in the art will appreciate that for some compounds having the formula (I), particular isomers can show greater pharmacological activity than other isomers.

There are many uses for the compounds having the formula (I). For instance, compounds having the formula (I) can be useful as antagonists of neurokinin receptors, particularly, $NK_1$ receptors in a mammal, such as a human. As such, they may be useful in treating and preventing one or more of a variety of mammalian (human and animal) disease states (physiolgical disorders, symptoms and diseases), for instance, respiratory diseases (e.g., chronic lung disease, bronchitis, pneumonia, asthma, allergy, cough and bronchospasm), inflammatory diseases (e.g., arthritis and psoriasis), skin disorders (e.g., atopic dermatitis and contact dermatitis), ophthalmalogical disorders (e.g., retinitis, ocular hypertension and cataracts), central nervous system conditions, such as depressions (e.g., neurotic depression), anxieties (e.g., general anxiety, social anxiety and panic anxiety disorders), phobias (e.g., social phobia), and bipolar disorder, addictions (e.g., alcohol dependence and psychoactive substance abuse), epilepsy, nociception, psychosis, schizophrenia, Alzheimer's disease, AIDs related dementia, Towne's disease, stress related disorders (e.g., post tramautic stress disorder), obsessive/compulsive disorders, eating disorders (e.g., bulemia, anorexia nervosa and binge eating), mania, premenstrual syndrome, gastrointestinal disorders (e.g., irritable bowel syndrome, Crohn's disease, colitis, and emesis), atherosclerosis, fibrosing disorders (e.g., pulmonary fibrosis), obesity, Type II diabetes, pain related disorders (e.g., headaches, such as migraines, neuropathic pain, post-operative pain, and chronic pain syndromes), bladder and genitourinary disorders (e.g., interstitial cystitis and urinary incontinence), and nausea. In particular, the compounds having the formula (I) are useful for treating disease states related to microvascular leakage and mucus secretion. Consequently, the compounds of the invention are especially useful in the treatment and prevention of asthma, emesis, nausea, depressions, anxieties, cough and pain related disorders.

In still another aspect of the invention, a method is provided for antagonizing an effect of a Substance P at a neurokinin-1 receptor site or for the blockade of one or more neurokinin-1 receptors in a mammal in need of such treatment, comprising administering to the mammal an effective amount of at least one compound having the formula (I).

In another embodiment of the invention, an effective amount of one or more of the inventive $NK_1$ receptor antagonists may be combined with an effective amount of one or more selective serotonin reuptake inhibitors ("SSRIs") to treat depression or anxiety. SSRIs alter the synaptic availability of serotonin through their inhibition of presynaptic reaccumulation of neuronally released serotonin. U.S. Pat. No. 6,162,805, which is incorporated herein by reference in its entirety, discloses a method for treating obesity with a combination therapy of a $NK_1$ receptor antagonist and an SSRI. An inventive compound(s) having the formula (I) can be combined together with an SSRI(s) in a single pharmaceutical composition or it can be administered simultaneously, concurrently or sequentially with an SSRI.

Numerous chemical substances are known to alter the synaptic availability of serotonin through their inhibition of presynaptic reaccumulation of neuronally released serotonin. Representative SSRIs include, without limitation, the following: fluoxetine, fluvoxamine, paroxetine, sertaline, and pharmaceutically-acceptable salts thereof. Other compounds can readily be evaluated to determine their ability to selectively inhibit serotonin reuptake. Thus, the invention relates to a pharmaceutical composition comprising at least one $NK_1$ receptor antagonist having the formula (I) and at least one SSRI, and a method of treating the above identified mammalian disease states, the method comprising administering to a patient in need of such treatment an effective amount of the pharmaceutical composition comprising at least one $NK_1$ receptor antagonist having the formula (I) in combination with at least one SSRI, such as one of those recited above.

In another aspect, the invention relates to a method of treating emesis, comprising administering to a patient in need of such treatment an effective amount of at least one $NK_1$ receptor antagonist having the formula (I). Compounds of the present invention are particularly useful in treating delayed onset emesis such as that experienced 24 hours to several days after the administration of chemotherapy. See Gonzales et al, *Oncology Special Edition, Vol.* 5 (2002), p. 53-58. Combinations of at least one $NK_1$ receptor antagonist and at least one other anti-emetic agent such as a serotonin $5-HT_3$ receptor antagonist, a corticosteroid or a substituted benzamide can be used to treat other forms of emesis, e.g., acute emesis induced by chemotherapy, radiation, motion and alcohol (e.g., ethanol), and post-operative nausea and vomiting. Examples of serotonin $5-HT_3$ receptor antagonists are palonsetron, dolasetron, ondansetron and granisetron, or a pharmaceutically-acceptable salts thereof. An examples of a suitable corticosteroid is dexamethasone. An example of a substituted benzamide is metoclopramide.

Preferred combinations for the treatment of emesis include a compound of formula I and a serotonin $5-HT_3$ receptor antagonist; a compound of formula I and a corticosteroid; a compound of formula I and a substituted benzamide; a compound of formula I, a serotonin $5-HT_3$ receptor antagonist and a corticosteroid; and a compound of formula I, a substituted benzamide and a corticosteroid.

When an inventive $NK_1$ receptor antagonist is combined with an SSRI, a serotonin $5-HT_3$ receptor antagonist, a corticosteroid or a substituted benzamide for administration to a patient in need of such treatment, the two or more active ingredients can be administered simultaneously, consecutively (one after the other within a relatively short period of time), or sequentially (first one and then the other over a period of time).

Thus, the compounds of the invention may be employed alone or in combination with other agents. In addition to the above described $NK_1$ receptor antagonist/SSRI or serotonin $5-HT_3$ receptor antagonist combination therapy, the compounds having the formula (I) may be combined with other active agents, such as other types of $NK_1$ receptor antagonists, prostanoids, $H_1$ receptor antagonists, α-adrenergic receptor agonists, dopamine receptor agonists, melanocortin receptor agonists, endothelin receptor antagonists, endothelin converting enzyme inhibitors, angiotensin II receptor antagonists, angiotensin converting enzyme inhibitors, neutral metalloendopeptidase inhibitors, $ET_A$ antagonists, renin inhibitors, serotonin $5-HT_{2c}$ receptor agonists, nociceptin receptor agonists, rho kinase inhibitors, potassium channel modulators and/or inhibitors of multidrug resistance protein 5. Preferable therapeutic agents for combination therapy with compounds of the invention are the following: prostanoids, such as prostaglandin $E_1$; α-adrenergic agonists, such as phentolamine mesylate; dopamine receptor agonists, such as apomorphine; angiotensin II antagonists, such as losartan, irbesartan, valsartan and candesartan; and $ET_A$ antagonists, such as bosentan and ABT-627. Dosage ranges for the other agent can be determined from the literature.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 4,000 mg, preferably from about 0.02 mg to about 1000 mg, more preferably from about 0.03 mg to about 500 mg, and most preferably from about 0.04 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.02 mg/day to about 2000 mg/day, in two to four divided doses.

The quantity of $NK_1$ receptor antagonist in combination with a SSRI or serotonin 5-$HT_3$ receptor antagonist (5-$HT_3$) in a unit dose of preparation may be varied or adjusted from about 10 to about 300 mg of $NK_1$ receptor antagonist combined with from about 10 to about 100 mg of SSRI or 5-$HT_3$. A further quantity of $NK_1$ receptor antagonist in combination with a SSRI or 5-$HT_3$ in a unit dose of preparation may be varied or adjusted from about 50 to about 300 mg of $NK_1$ receptor antagonist combined with from about 10 to about 100 mg of SSRI or 5-$HT_3$. An even further quantity of $NK_1$ receptor antagonist in combination with SSRI or 5-$HT_3$ in a unit dose of preparation may be varied or adjusted from about 50 to about 300 mg of $NK_1$ receptor antagonist combined with from about 20 to about 50 mg of SSRI or 5-$HT_3$, depending on the particular application. Dosage levels for the corticosteroids and substituted benzamides can be determined form the literature.

Alternatively, separate dosage forms of the compounds of formula I and the other agents can be provided in a single package as a kit for the convenience of the patient. This is particularly useful when the separate components must be administered in different dosage forms (e.g., a tablet and a capsule) or at different dosage schedules.

Upon improvement of a patient's condition, a maintenance dose of a compound, composition or combination of the invention may be administered, if necessary. Subsequently, the dosage or frequency of administration, or both, may be reduced, as a function of the symptoms, to a level at which the improved condition is retained. When the symptoms have been alleviated to the desired level, treatment should cease. Patients may, however, require intermittent treatment on a long-term basis upon any recurrence of disease symptoms.

The inventive compounds can exist in unsolvated as well as solvated forms, including hydrated forms. In general, the solvated forms, with pharmaceutically-acceptable solvents, such as water, ethanol, and the like, are equivalent to the unsolvated forms for purposes of this invention.

The inventive compounds may form pharmaceutically-acceptable salts with organic and inorganic acids. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in a conventional manner. The free base forms may be regenerated by treating the salt with a suitable dilute aqueous base solution, such as dilute aqueous sodium hydroxide, potassium carbonate, ammonia or sodium bicarbonate. The free base forms may differ somewhat from their respective salt forms in certain physical properties, such as solubility in polar solvents, but the salts are otherwise equivalent to their respective free base forms for purposes of the invention.

Acidic compounds of the invention (e.g., those compounds which possess a carboxyl group) form pharmaceutically-acceptable salts with inorganic and organic bases. Representative examples of such types of salts are sodium, potassium, calcium, aluminum, gold and silver salts. Also included are salts formed with pharmaceutically-acceptable amines, such as ammonia, alkyl amines, hydroxyalkylamines, N-methylglucamine, and the like.

Following are general and specific methods of preparing compounds having the formula (I). As used herein, the following abbreviations are defined as follows:
RBF is a round bottom flask;
RT is room temperature;
Me is methyl;
Bu is butyl;
Ac is acetyl;
Et is ethyl;
Ph is phenyl;

THF is tetrahydrofuran;
OAc is acetate;
(Boc)₂O is di-tert-butyl dicarbonate;
(Boc) is tert-butoxy carbonyl;
TLC is thin layer chromatography;
LAH is lithium aluminum hydride;
LDA is lithium diisopropyl amine;
CDI is 1,1-carbonyl diimidazole;
HOBT is hydroxybenzotriazole;
DEC is 1[3-(dimethylamino)propyl]-3-ethylcarbodiimide hydrochloride;
TFA is trifluoroacetic acid;
MTBE is t-butyl methyl ether;
DIEA or i-Pr₂EtN is diisopropylethyl amine;
Prep plate is preparative thin layer chromatography;
DMF is dimethyl formamide
DMPU is 1,3-dimethyl-3,4,5,6-tetrahydro-2(1H)-pyrimidinone
TEMPO is a free radical of 2,2,6,6-tetra methyl-1-piperidinyloxy;
BuLi is butyl lithium;
KHMDS is potasium bis(trimethylo silyl)amide; and
DBU is 1,8-diazabicyclo[5.4.0]un dec-7-ene.

Compounds having the formula (I) can be prepared using methods known to those skilled in the art. Typical procedures are described below, although a skilled artisan will recognize that other procedures may be applicable, and that the procedure may be suitably modified to prepare other compounds within the scope of formula (I).

General Methods of Preparation

Compounds having the formula (I) may be generally prepared from the corresponding protected oxazolidinone derivative $A_1$ as shown under the following conditions, where $Ar^1$ and $Ar^2$ are each defined as in the summary of the invention; $X^1$ is —O—; $R^1$ through $R^{33}$, independently of one another, are each defined as in the summary of the invention; and $n_2$ is 1.

The stereoselective alkylation of a protected oxazolidinone A1 provides the protected oxazolidinone A2. Partial reduction with a reducing agent, such as LAH, provides the lactol A3. A Wittig reaction provides the corresponding olefin A4. Hydrogenation of the olefin A4 and cyclization provides the lactam A5. If the protecting group (Pr) on the nitrogen is Cbz then it might cleave under hydrogenation conditions. The deprotection of the nitrogen of the lactam A5, if necessary, followed by reduction of the lactam with reducing agents such as LAH or LAH/AlCl₃, preferably LAH/AlCl₃, provides substituted pyrrolidines A6.

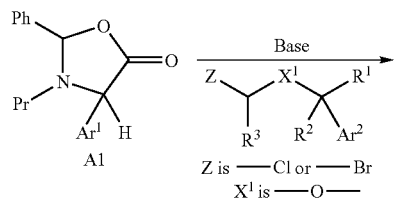

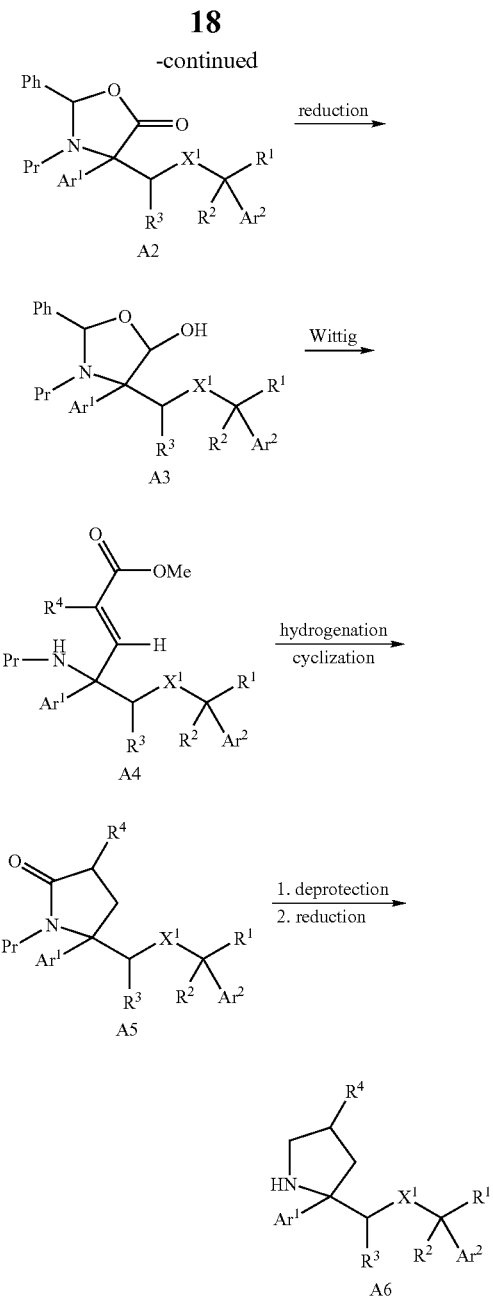

Compounds having the formula I, where $n_2$ is 1 and $R^4$ is —NR¹³R¹⁴, —NR¹²SO₂R¹³, —NR¹²C(O)R¹⁴, or —NR¹²(C(O)NR¹³R¹⁴) can also be prepared by conversion of lactol A3 to olefin A7 via Wittig reaction using a nitrogen protected (NPr') glycine ester Wittig reagent where Pr' can be a Boc or Cbz protecting group and Pr is preferably a Cbz protecting group. Palladium catalyzed hydrogenation and deprotection (if Pr is a Cbz group) of olefin A7, followed by spontaneous cyclization will provide lactam A8. When Pr is not Cbz or a protecting group readily cleaved under standard hydrogenation conditions, then hydrogenation of the olefin A7 is followed by deprotection of —NHPr and subsequent cyclization to provide lactam A8. The deprotection of the N—Pr' group, if necessary, followed by the reduction of the lactam with reducing agents as LAH or LAH/AlCl₃, preferably LAH/AlCl₃, provides amino-pyrrolidines A9 which can further be functionalized using standard conditions to give N-substituted pyrrolidines A10.

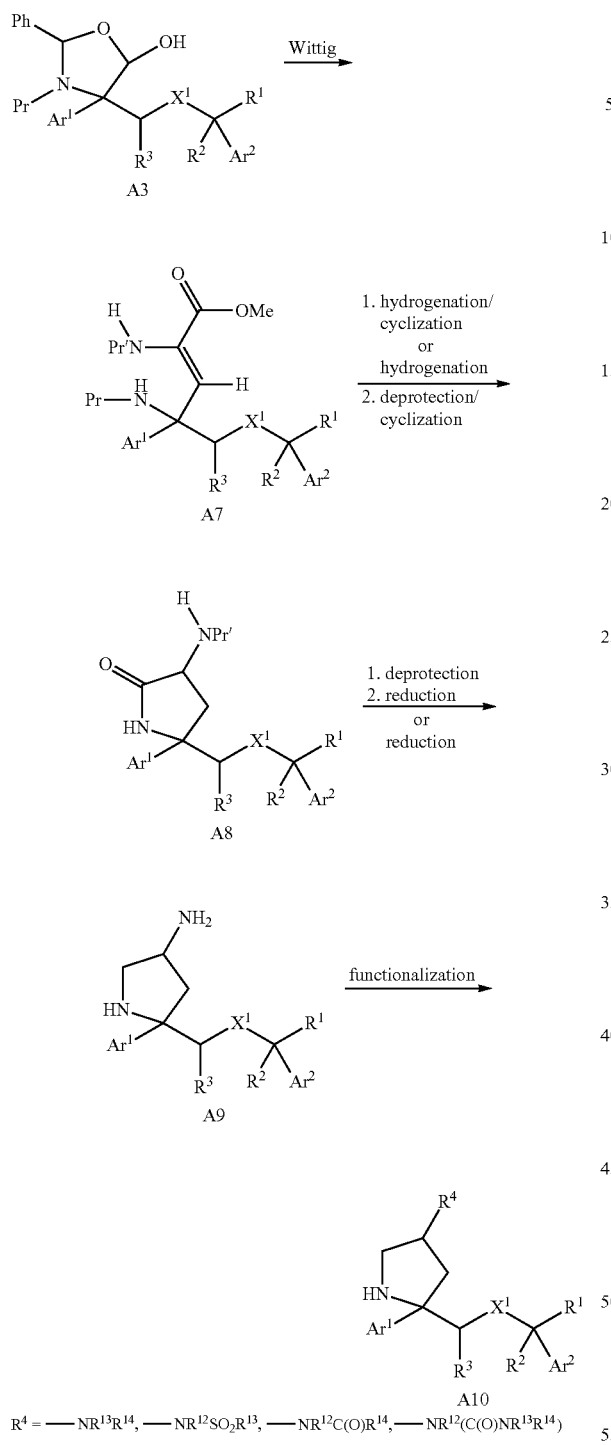

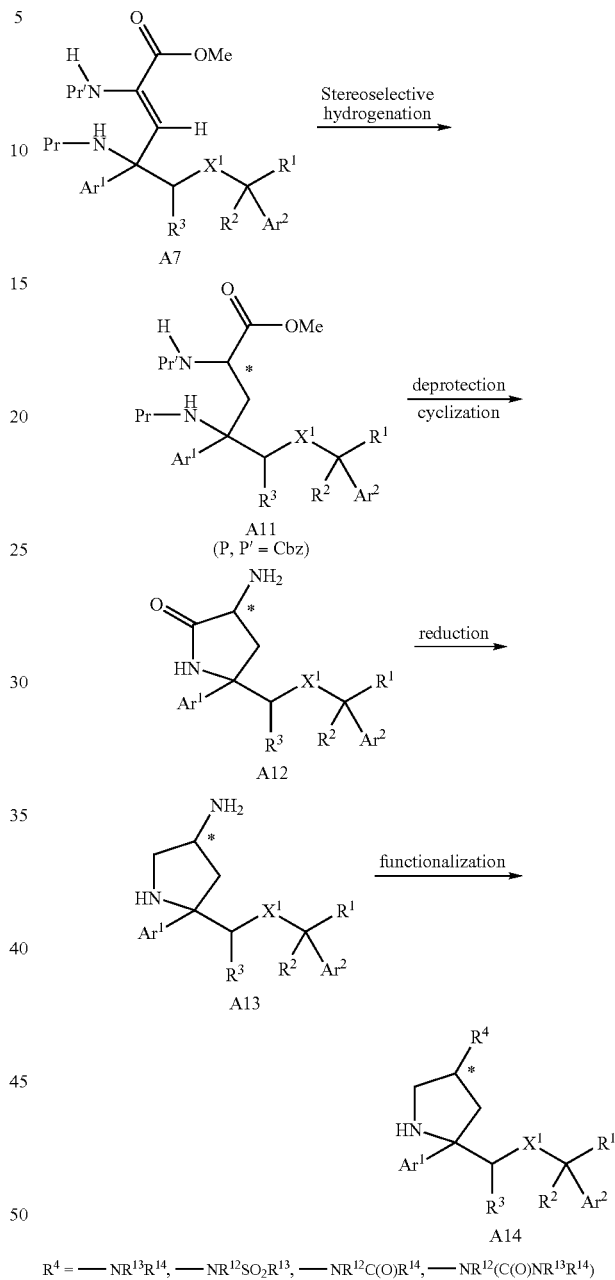

further be functionalized using standard conditions to give N-substituted pyrrolidines A14.

Those skilled in the art will appreciate that the stereoselective hydrogenation of the double bond of olefin A7 are can also be performed using a chiral hydrogenation catalyst such as chiral Rhodium catalyst which can provide chiral ester A11. Deprotection of the protecting group (if Pr, Pr' are Cbz groups) under standard hydrogenation conditions followed by spontaneous cyclization will provide chiral amino-lactam A12. The reduction of the chiral amino-lactam A12 with reducing agents as LAH or LAH/AlCl$_3$, preferably, LAH/AlCl$_3$, provides chiral amino-pyrrolidines A13 which can Compounds having the formula I, where $n_2$ is 2, 3 or 4, may be prepared by conversion of the lactol A3 to carbon homologated derivatives A15 (n is 1, 2 or 3) using routine chemistry known to those skilled in the art. Particularly useful reagents for this carbon chain homologation include: Wittig chemistry using methoxymethyl triphenylphosphonium bromide or an analogous reagent, cyanomethyl triphenylphosphonium bromide and Horner-Emmons protocols, and aldol chemistry. Hydrogenation and cyclization to the 6-, 7- and 8-membered lactams A17, respectively, and deprotection and reduction to the 6-, 7- and 8-membered substituted reduced lactams A18, are analogous to the previously described procedures.

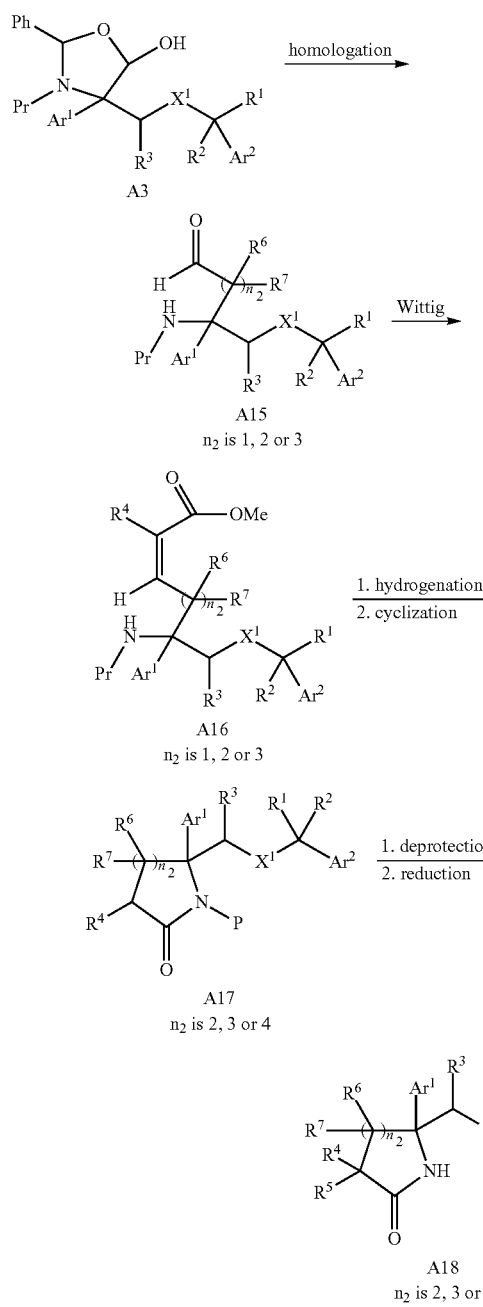

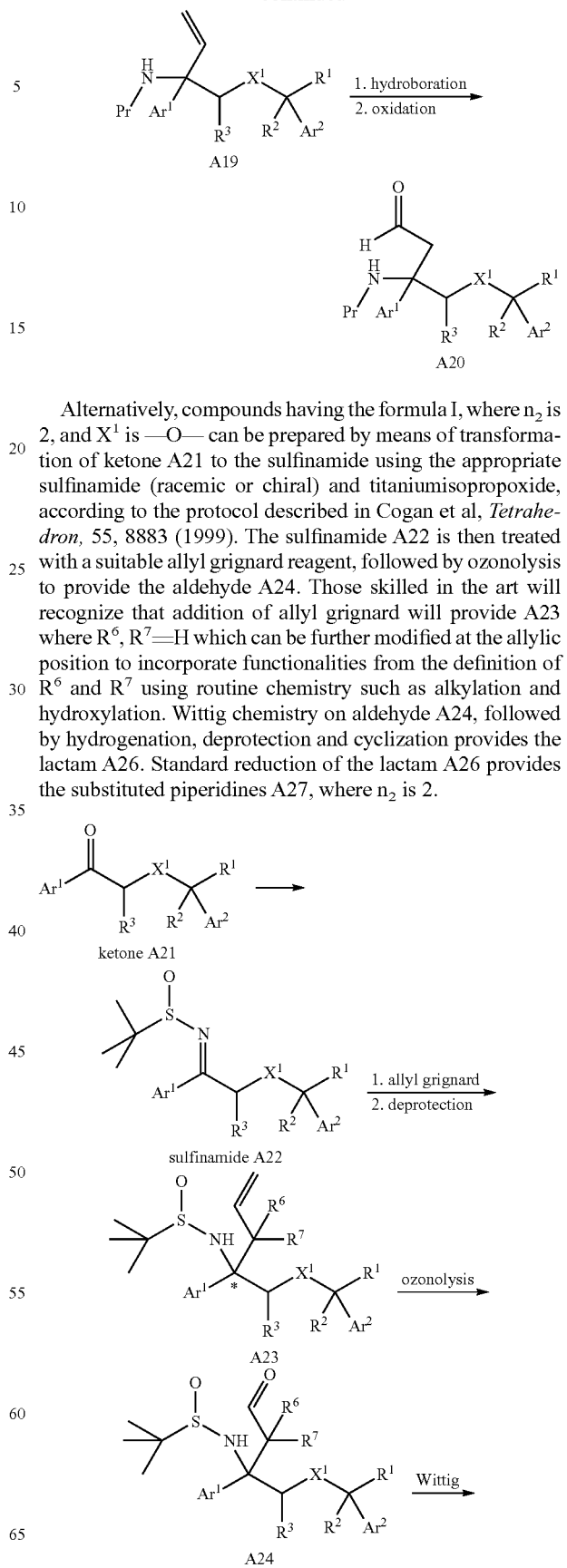

Alternatively, compounds having the formula I, where $n_2$ is 2, and $X^1$ is —O— can be prepared by means of transformation of ketone A21 to the sulfinamide using the appropriate sulfinamide (racemic or chiral) and titaniumisopropoxide, according to the protocol described in Cogan et al, *Tetrahedron*, 55, 8883 (1999). The sulfinamide A22 is then treated with a suitable allyl grignard reagent, followed by ozonolysis to provide the aldehyde A24. Those skilled in the art will recognize that addition of allyl grignard will provide A23 where $R^6$, $R^7$=H which can be further modified at the allylic position to incorporate functionalities from the definition of $R^6$ and $R^7$ using routine chemistry such as alkylation and hydroxylation. Wittig chemistry on aldehyde A24, followed by hydrogenation, deprotection and cyclization provides the lactam A26. Standard reduction of the lactam A26 provides the substituted piperidines A27, where $n_2$ is 2.

Another method for preparing aldehyde A15 where $R^6$, $R^7$=H involves Wittig homologation of lactol A3 to ethylene derivative A19 which upon hydroboration, preferably with 9-BBN, and subsequent oxidation provides aldehyde A20.

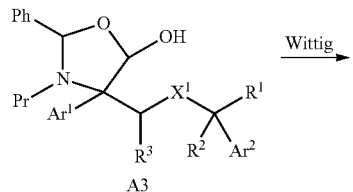

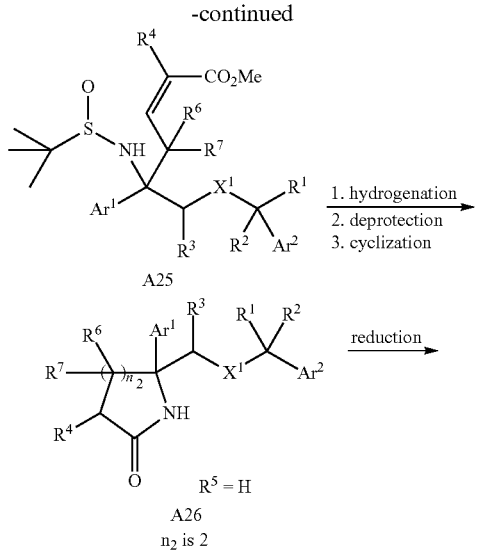

A25

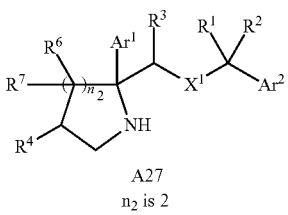

A26
$n_2$ is 2

A27
$n_2$ is 2

When $X^1$ is as defined in the summary of the invention, the ketone A21 wherein $X^1$ is an ether, thio or imino group may be prepared using several different methods employing commercially available materials. Ketone A28 can be subjected to acylation ($Q^1$ is —$NH_2$, —OH or —SH), reductive amination ($Q^1$ is —$NH_2$), ether formation ($Q^1$ is —OH) by standard alkylation methods, thio ether formation ($Q^1$ is —SH) by standard alkylation methods, or esterification ($Q^1$ is —OH or —SH). Alternatively, the corresponding alcohol A29 can be oxidized to an aldehyde and treated with an aryl or heteroaryl organometallic reagent, followed by oxidation to give ketone A21.

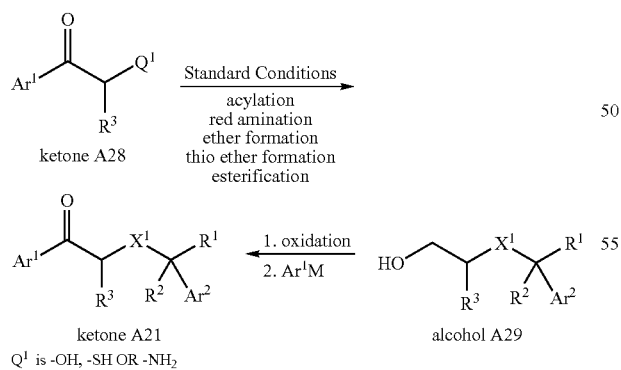

Another method for preparing ketone A21 involves nucleophilic displacement of a leaving group, such as —Cl, —Br, —I, —OMs and —OTf, adjacent to the aryl or heteroaryl ketone, for example, see WO 01/44200 (2001), which is incorporated herein in its entirety by reference. Accordingly, a suitable substituted styrene or heteroaryl epoxide may be opened with the appropriate nucleophile to give the desired $X^1$:

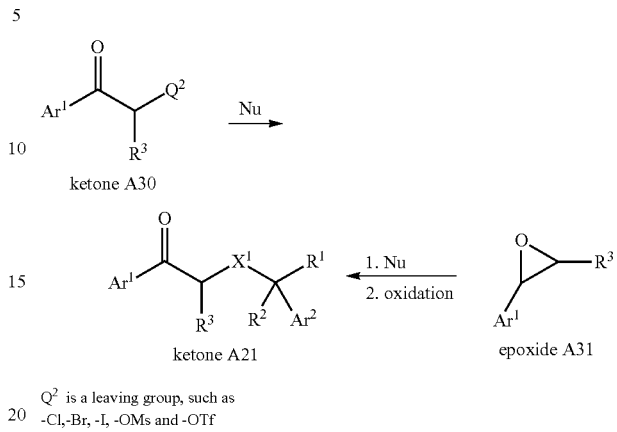

$Q^2$ is a leaving group, such as —Cl, —Br, —I, —OMs and —OTf

Compounds having the formula I where $n_2$ is 2 and $R^4$ or $R^5$ is —$NR^{13}R^{14}$, —$NR^{12}SO_2R^{13}$, —$NR^{12}C(O)R^{14}$, or —$NR^{12}(C(O)NR^{13}$ $R^4$) can also be prepared from aldehyde A15 using the chemistry as described earlier for the pyrrolidine compounds ($n_2$=1).

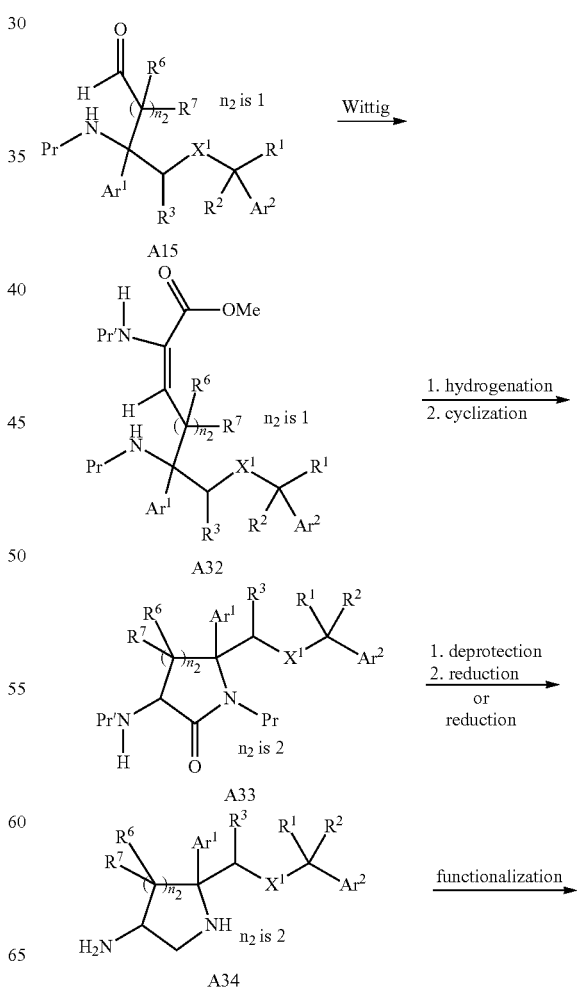

-continued

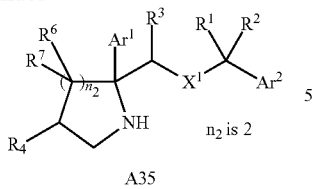

A35

$R^4 = -NR^{13}R^{14}, -NR^{12}SO_2R^{13},$
$-N^{12}C(O)R^{14}, -NR^{12}(C(O)NR^{13}R^{14})$

Those skilled in the art will appreciate that the stereoselective hydrogenation of the double bond of olefin A32 can also be performed using a chiral hydrogenation catalyst such as chiral Rhodium catalyst which can provide chiral ester A36. The chiral ester A36 can be converted to chiral functionalized amino-piperidine compounds A39 using the chemistry as described earlier for the chiral functionalized amino-pyrrolidine compounds ($n_2=1$).

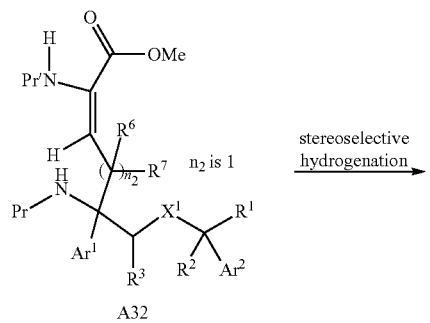

A32

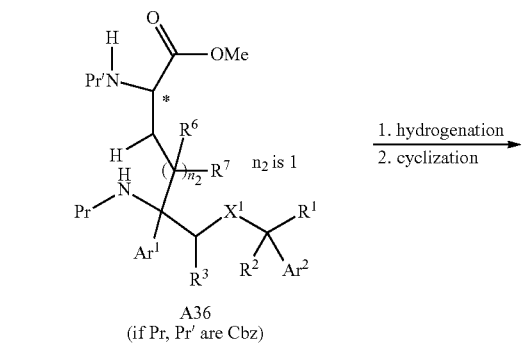

A36
(if Pr, Pr' are Cbz)

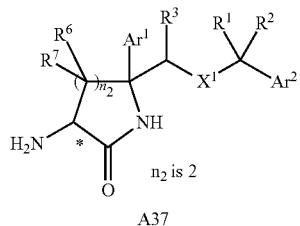

A37

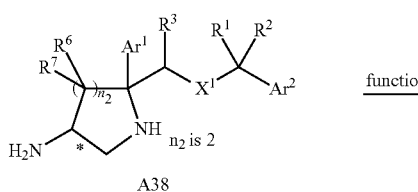

A38

-continued

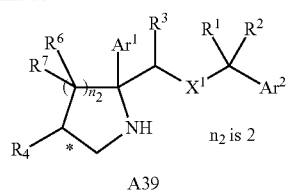

A39

$R^4 = -NR^{13}R^{14}, -NR^{12}SO_2R^{13},$
$-NR^{12}C(O)R^{14}, -NR^{12}(C(O)NR^{13}R^{14})$

Those skilled in the art will appreciate that homologation of the aldehyde A15 followed by subsequent synthetic operations as described above will result in the cyclic reduced lactams, where $n_2$ is 3 or 4.

Another method of preparing compounds having the formula I, where $n_2$ is 2, and $X^1$ is —O—, involves the alkyation of amine derivative A40 with a suitable substituted allylic halide, preferably a 2-substituted allylic bromide, to bis olefin A41. Treatment of the bis olefin A41 with Grubb's or Schrock's catalyst using standard olefin metathesis conditions provides the unsaturated piperidine derivative A42. Deprotection of the nitrogen and hydrogenation provides the six-membered cyclic reduced lactams or substituted piperidines A43. If the protecting group (Pr) on the nitrogen is Cbz, then it might cleave under hydrogenation conditions. Those skilled in the art will appreciate that alkylation of amine A40 with an appropriate substituted alkyl halide of 4 to 5 carbon atoms in length containing a terminal olefin, followed by subsequent synthetic operations as described above will result in the substituted cyclic reduced lactams, where $n_2$ is 3 or 4.

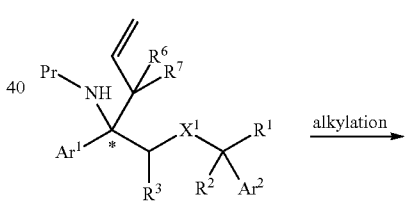

A40

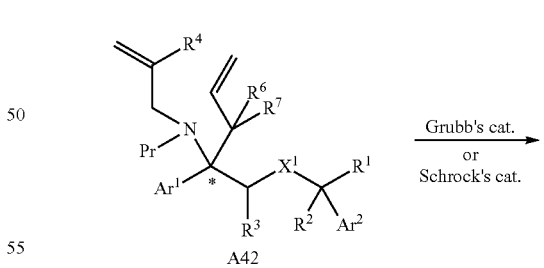

A42

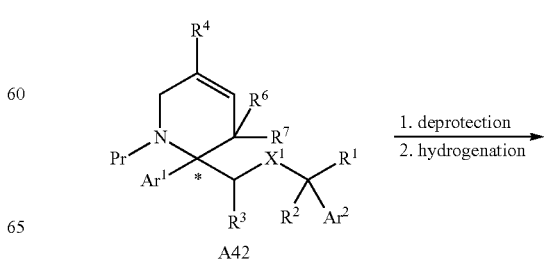

A42

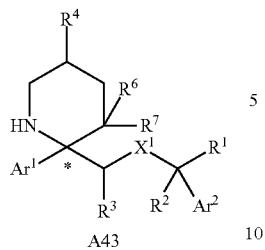

A43

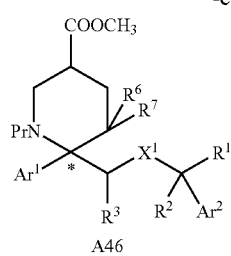

A46

When R⁴=COOCH₃, the chemistry as described above provides A46 where ester group could be further transformed to other functional groups such as amide (R⁴=CONR¹³R¹⁴) and alcohol (R⁴=CH₂OH) using standard chemistry. In addition, the piperidine A46 can be further functionalized using chemistry such as alkylation followed by deprotection of the nitrogen, if necessary, to provide substituted piperidines A47.

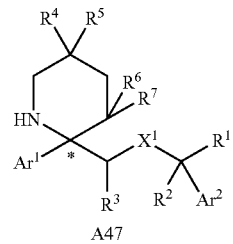

A47

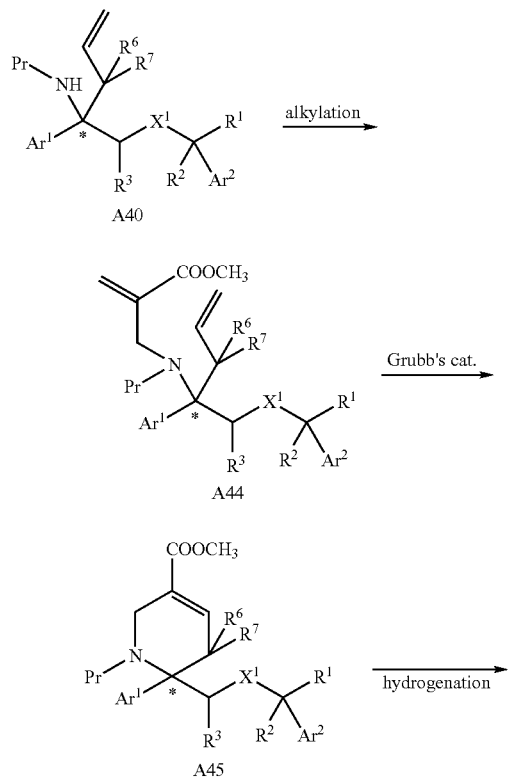

Another method of preparing compounds having the formula (I), where $n_2$ is 1, $X^1$ is —O— and $R^4$ is —OH, —O—($C_1$-$C_6$ alkyl), —O—($C_3$-$C_8$ cycloalkyl), —O—($C_1$-$C_6$ alkyl)-($C_3$-$C_8$ cycloalkyl), —OC(O)R, or —OCONR¹³R⁴, from lactol A3 involves Wittig chemistry to provide the corresponding olefin ester A48. Hydrogenation of the olefin ester A48, followed by reduction to the alcohol using metal hydride reducing agents, preferably LiBH₄, and subsequent oxidation, such as Swern or bleach, gives aldehyde A50. The cyclization of aldehyde A50 provides enamide A51 which upon hydroxylation, preferably using a borane gives alcohol A52. The alcohol A52 can be oxidized under standard oxidation conditions such as Swern oxidation to give ketone A53. Treatment of the ketone with a suitable organometallic reagent provides the tertiary alcohol A54. For instances where the desired R⁵ substituent cannot be incorporated directly with an organometallic reagent, further functionalization at the R⁵ position may be necessary. The hydroxyl group of alcohol A54 can be further functionalized using standard chemistry followed by deprotection to give disubstituted pyrrolidines A55. Alternatively, the further modification of the secondary alcohol A52 under standard conditions and deprotection of the nitrogen provides the monosubstituted pyrrolidines A56.

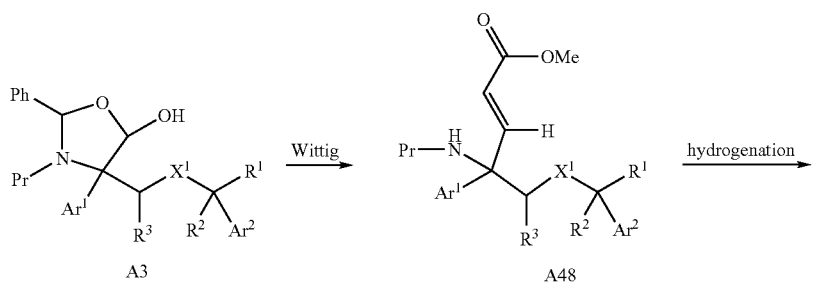

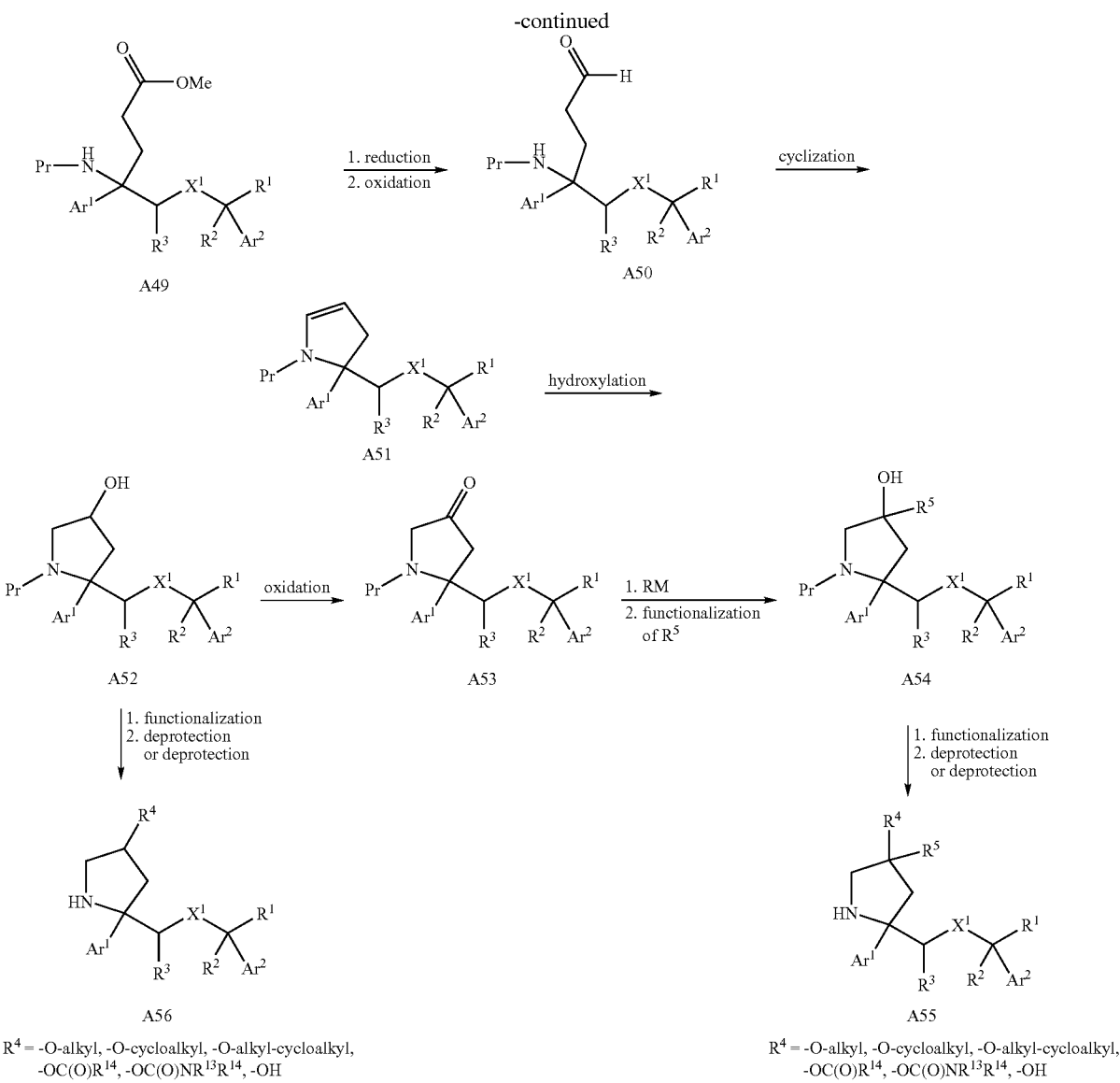

Compounds having the formula I, where $n_2$ is 2, $X^1$ is —O— and $R^4$ is —OH, —O—($C_1$-$C_6$ alkyl), —O—($C_3$-$C_8$ cycloalkyl), ), —O—($C_1$-$C_6$ alkyl)-($C_3$-$C_8$ cycloalkyl), —OC(O)$R^{14}$ or —OCONR$^{13}$R$^{14}$, can be prepared from lactol A3. Wittig chemistry followed by hydrogenation and cyclization in weakly acidic conditions such as p-toluenesulfonic acid provides the enamide A59. Using the synthetic operations as described above from the enamide A51, the enamide A59 will result in the disubstituted piperidines A63 and monosubstituted piperidines A64.

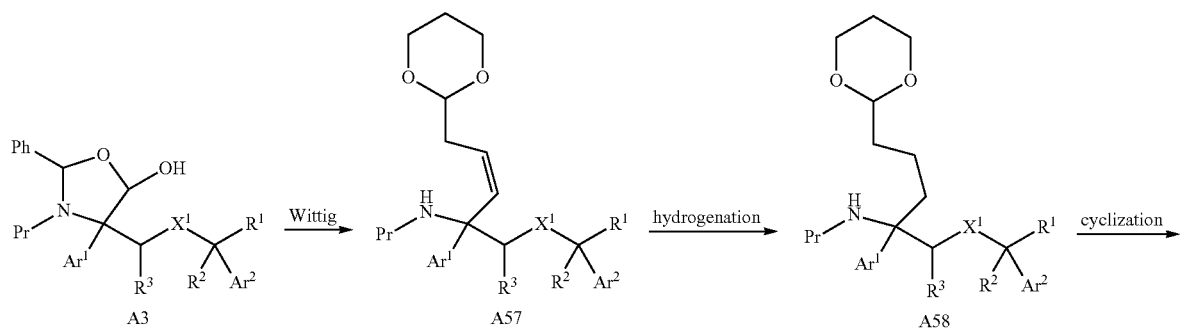

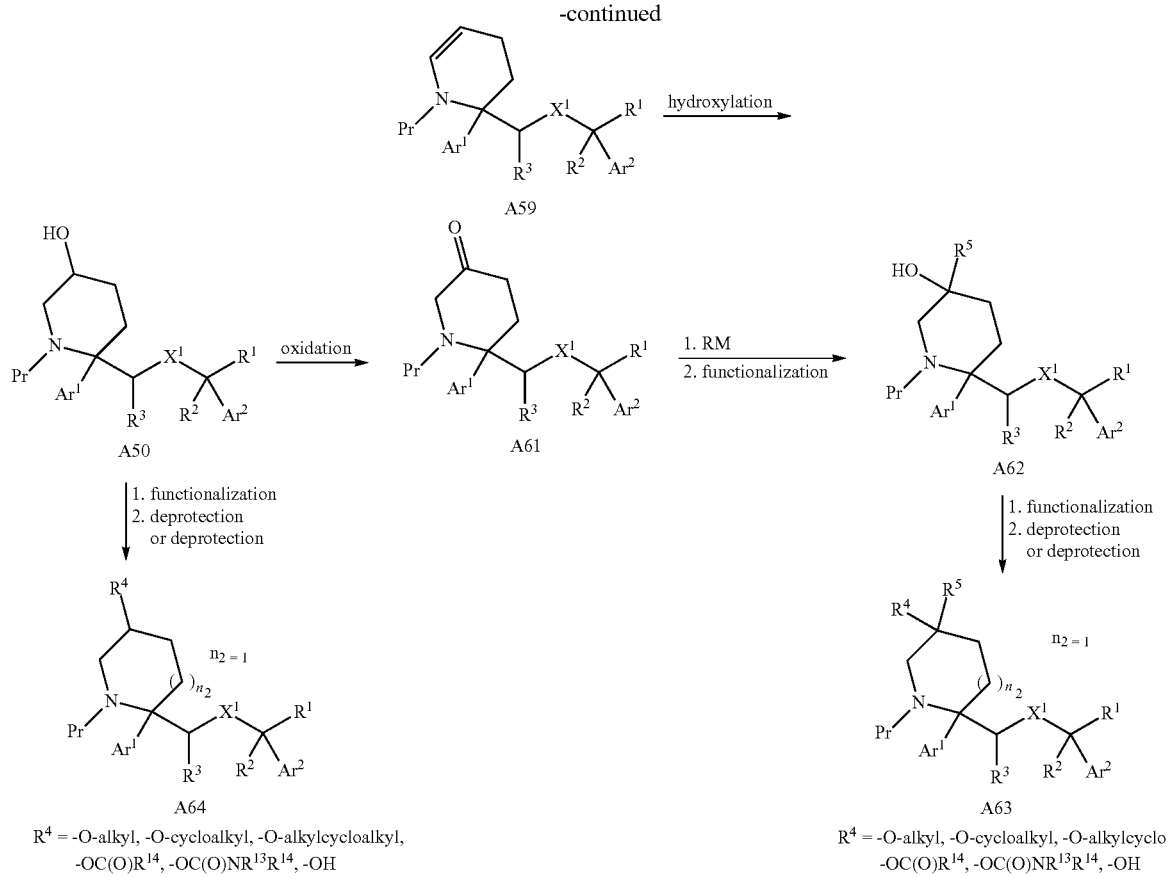

Those skilled in the art will appreciate that homologation of the lactol A3 to the aldehyde A15 where $n_2$ is 2 or 3 followed by subsequent synthetic operations as described above will result in the monosubstituted cyclic amines A64 or disubstituted cyclic amines A63 where $n_2$ is 2 or 3.

The compounds having the formula I, where $n_2$ is 1, 2, 3 or 4, $X^1$ is —O— and, $R^4$ and $R^5$, together with the carbon to which they are both attached, form a chemically feasible 5 membered ring can be prepared from corresponding ketones. The ketone A65 is transformed into the corresponding hydantoin A66 by heating with KCN/ammonium carbonate in ethanol/water mixture or by using alternate standard conditions known to those skilled in the art. The amine is deprotected to give hydanotin A67 which can be converted to corresponding urea analogs A68 by reduction preferably with LAH/AlCl$_3$. Alternatively hydanotin A66 can be cleaved to amino-acid A69 using the protocol described in Kubik, S.; Meissner, R. S.; Rebek, J. *Tetrahedron Lett.* 35, 6635 (1994). Standard protection of the amino-acid A69 as a carbamate derivative (Pr') is followed by activation of the carboxylic acid. Treatment with phosgene or a phosgene equivalent, preferably triphosgene, is one such method for acid activation. The reduction of NBoc-UNCA A71 with reducing agents, preferably lithium borohydride, gives alcohol A72 which can be converted to five membered cyclic compounds such as carbamate A73 by intramolecular cyclization (if Pr' is carbamate protecting group such as Boc) using base, preferably NaH, followed by deprotection. Alternatively, alcohol A72 can be oxidized to NBoc-aldehyde A74 by standard oxidation conditions such as Swern oxidation and using the routine chemistry known to those skilled in the art. The NBoc-aldehyde A74 can be converted to cyclic analogs such as the y-lactam A75.

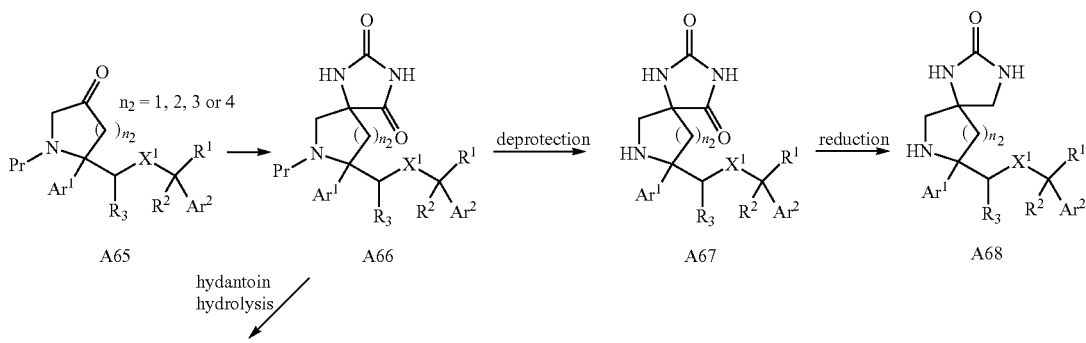

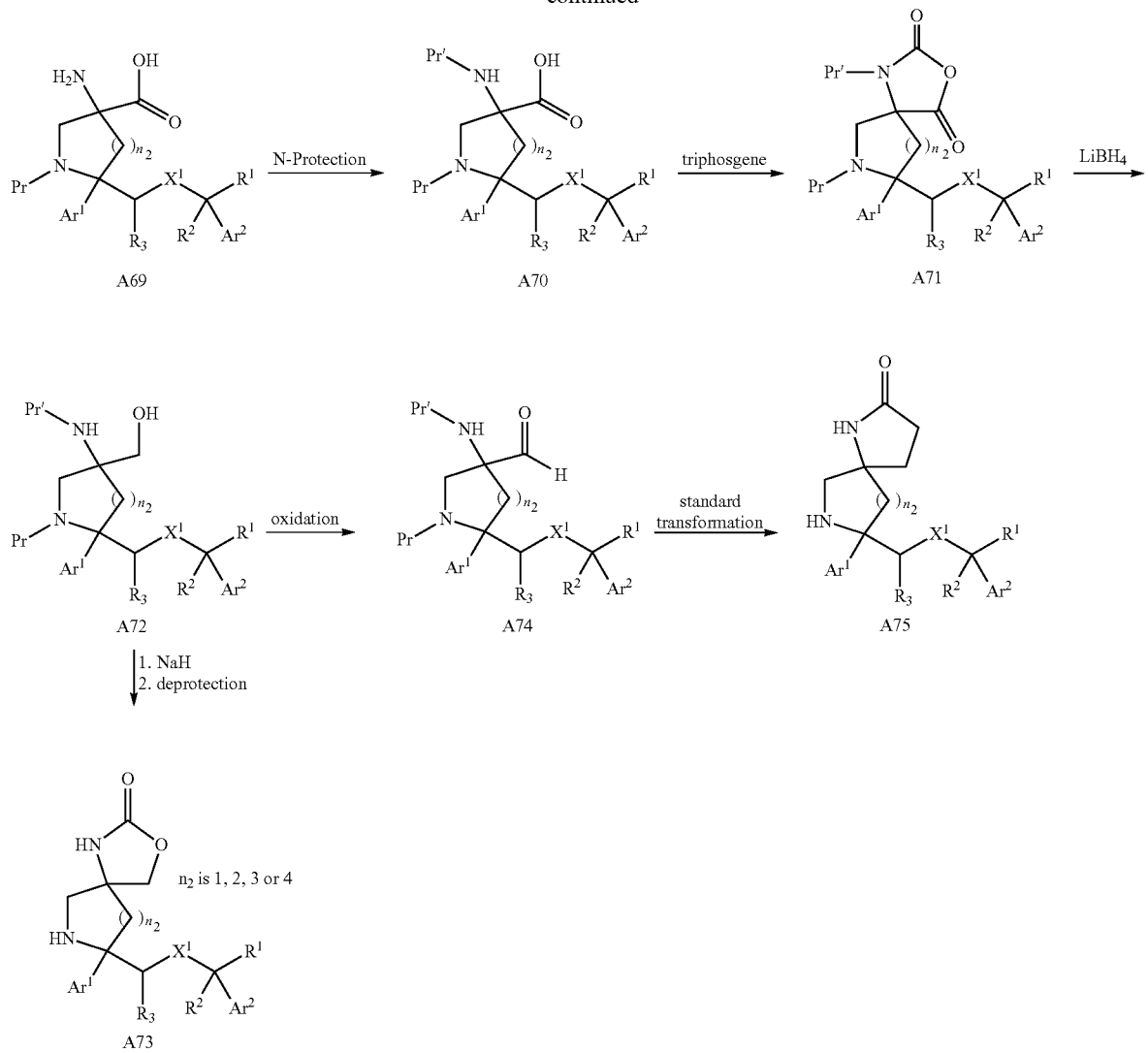

The compounds having the formula I, where $n_2$ is 1, 2, 3, or 4, $X^1$ is —O— and $R^4$ is —$NR^{13}R^{14}$, —$NR^{12}SO_2R^{13}$, —$NR^{12}COR^{14}$, —$NR^{12}C(O)OR^{13}$, or —$NR^{12}(CONR^{13}R^{14})$, and $R^5$ is —$C(O)NR^{13}R^{14}$ can be prepared by amidation of amino-acid A69 to give amino-amide A76 followed by functionalization of amino group and deprotection to provide disubstituted analogs A77. Alternatively, the NBoc-amino-acid A70 can be reacted with an amine, followed by deprotection of N—Pr' group to give amino-amide A76. The amino-amide A76 can also be deprotected to give analogs A78 where $R^4$ is —$NR^{13}R^{14}$ and $R^{13}$, $R^{14}$=H.

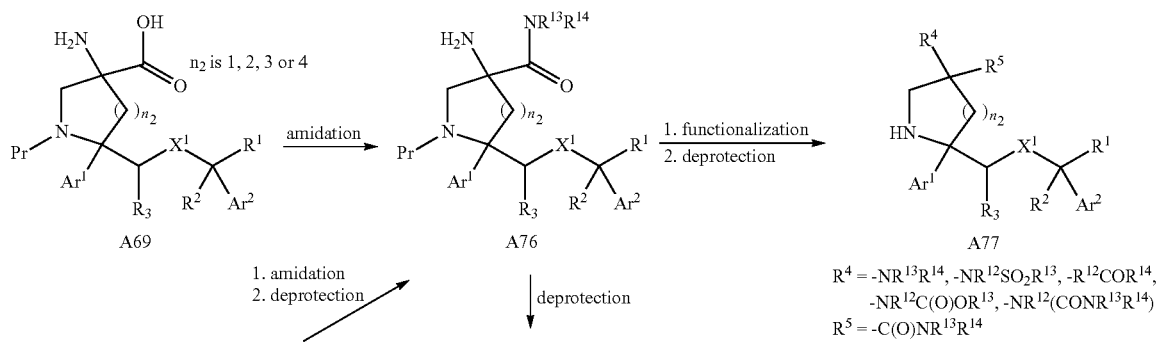

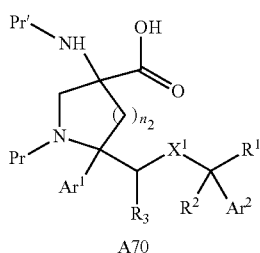
A70

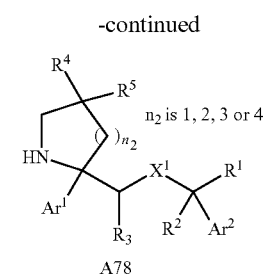
A78

$R^4 = -NR^{13}R^{14}$ where $R^{13}, R^{14} = H$
$R^5 = -C(O)NR^{13}R^{14}$

Another method of preparing compounds having the formula I, where $n_2$ is 1, 2, 3 or 4, $X^1$ is —O— and $R^{14}$ is —$NR^{13}R^{14}$, —$NR^{12}SO_2R^{13}$, —$NR^{12}COR^{14}$, —$NR^{12}C(O)OR^{13}$, or —$NR^{12}(CONR^{13}R^{14})$, involves treatment of ketone A65 with a 5 protected amine under appropriate conditions to provide imine A79. Nucleophilic addition of compatible organometallic reagents such as grignard or reduction (if $R^5$=H) of imine A79 followed by deprotection of nitrogen (N—Pr') provides amine A80. The functionalization of amine A80 under standard conditions and deprotection of nitrogen provides the substituted pyrrolidines A81.

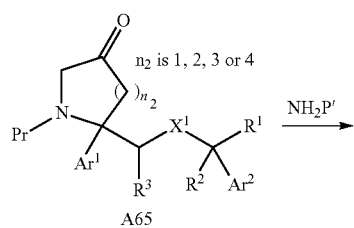
A65

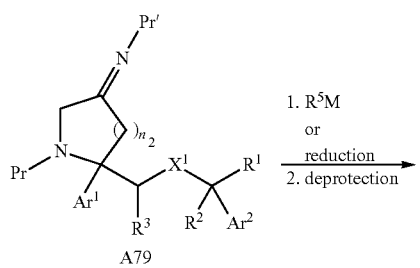
A79

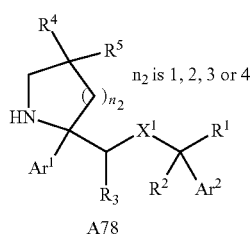
A80

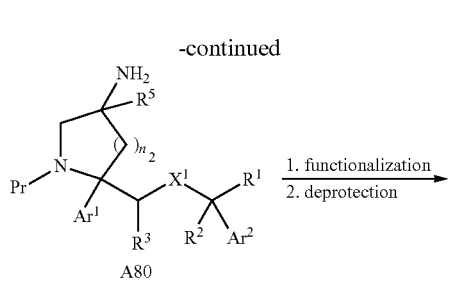
A81

$R^4 =$ —$NR^{13}R^{14}$, —$NR^{12}SO_2R^{13}$, —$NR^{12}COR^{14}$, —$NR^{12}C(O)OR^{13}$, —$NR^{12}(CONR^{13}R^{14})$

The compounds having the formula I, where $n_2$ is 1, 2, 3 or 4, $X^1$ is —O—, $R^5$ is H, and $R^4$ is a heterocyclic or heteroaryl group can be prepared by conversion of ketone A65 to nitrile A87, aldehyde A82 and a carboxylic acid A85 via aldehyde A82 using the standard oxidation conditions. Those who are skilled in the art will appreciate that the cyano, aldehyde and carboxylic acid compounds can provide the appropriate heterocyclic or heteroaryl functionality using standard chemistry.

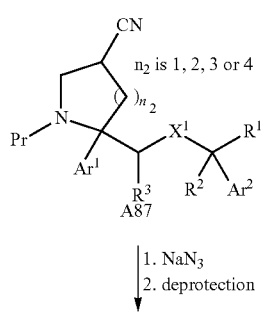
A87

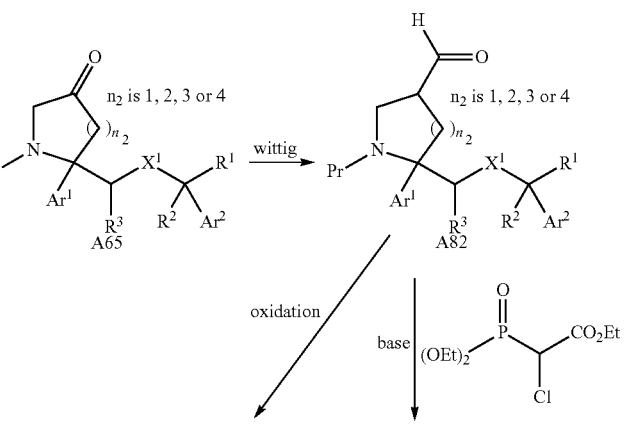

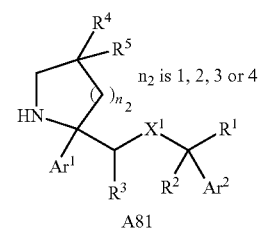

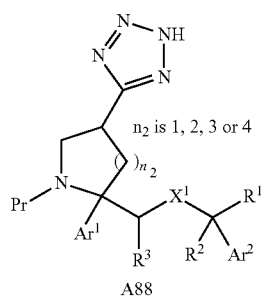

A88

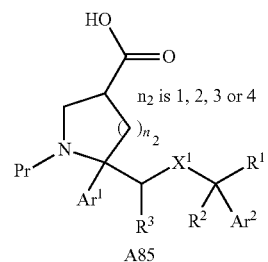

A85

1. EDC, NH$_2$NHCONH$_2$
2. cyclization
3. deprotection

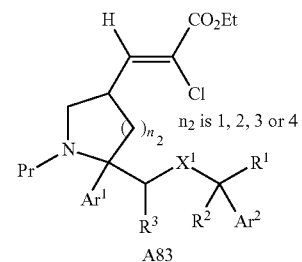

A83

1. NH$_2$NH$_2$
2. deprotection

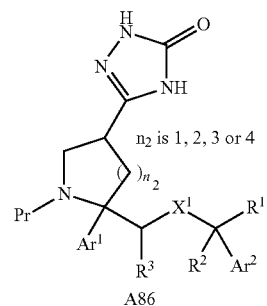

A86

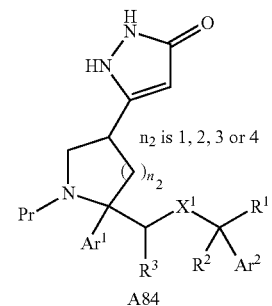

A84

Another method of preparing the compounds having the formula I, where $n_2$ is 1, 2, 3, or 4, $X^1$ is —O—, $R^5$ is H, and $R^4$ is a heterocyclic or heteroaryl group involves conversion of the ketone A65 to a vinyl triflate A89 by using a base such as LDA and triflic anhydride as an electrophile. The triflate A89 could be coupled with suitable organometalic reagents, preferably boronic acid, to give heterocyclic or heteroaryl unsaturated compound A90. The reduction of the double bond followed by deprotection of the amine (if necessary) provides heterocyclic or heteroaryl substituted cyclic amines A91.

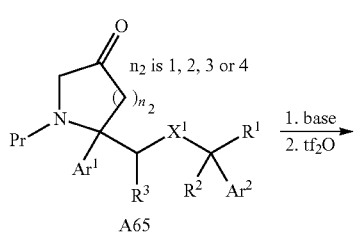

A65

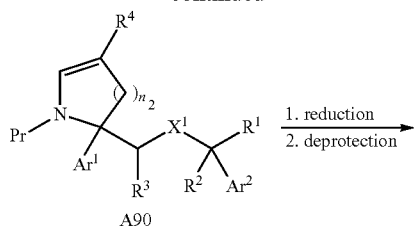

A90

1. reduction
2. deprotection

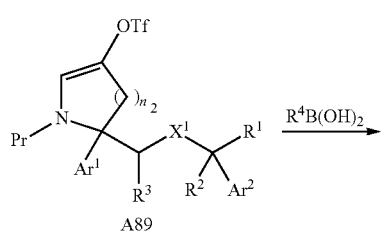

A89

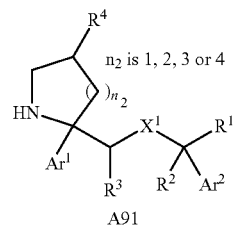

A91

$R^4$ = -heterocyclic or heteroaryl

The compounds having the formula I, where $n_2$ is 1, 2, 3, or 4, $X^1$ is —O— and $R^4$ is —C(OR$^{12}$)(R$^{13}$)(R$^{14}$), where $R^{14}$ is H, or —C(=NOR$^{14}$)(R$^{13}$) can be prepared by conversion of aldehyde A82 to an alcohol A92 via addition of an organometallic reagent. The alcohol A92 can be transformed to analogs such as A93 or it can be oxidized to ketone A94 which can provided analogs such as oxime A95 using the standard conditions.

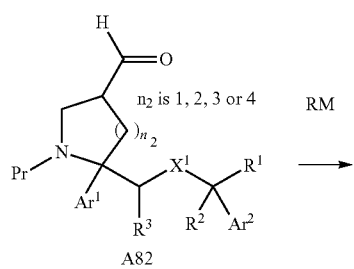

A82

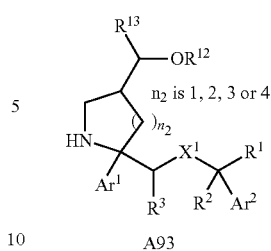

A93

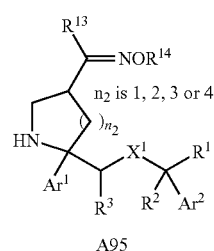

A95

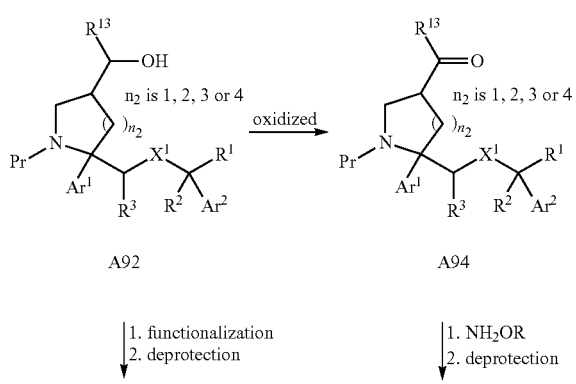

A92    A94

1. functionalization
2. deprotection

1. NH₂OR
2. deprotection

The compounds having the formula I, where n₂ is 1, 2, 3 or 4, $X^1$ is —O—, $R^5$ is H, and $R^4$ is —C($R^{28}R^{29}$)CON$R^{13}R^{14}$, where $R^{28}$, $R^{29}$=H or methyl, can be prepared by conversion of ketone A65 to unsaturated ester A96 using Wittig chemistry. Hydrogenation of the double bond and deprotection of the protecting group, if necessary, provides the ester A97. Conversion of the ester to amides A98 can be realized through treatment with amines, or transformation to the acid and subsequent coupling with amines using standard methods. In addition, the unsaturated ester A96 can also provide compounds where $R^4$ and $R^5$, together with the carbon to which they are attached, form a five membered cyclic ring such as lactam A100.

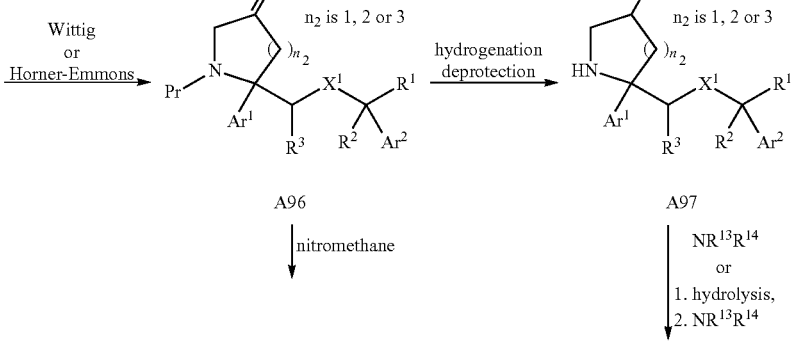

A65    A96    A97

Wittig or Horner-Emmons hydrogenation deprotection nitromethane

NR¹³R¹⁴ or
1. hydrolysis,
2. NR¹³R¹⁴

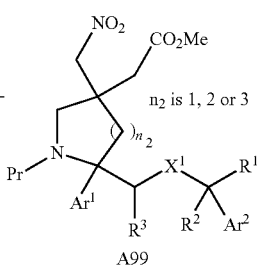

A100

1. hydrogenation deprotection
2. cyclization

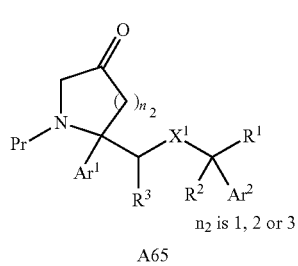

A99

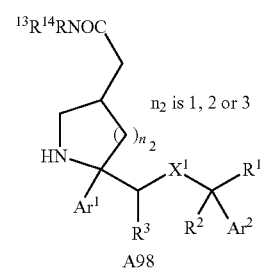

A98

Those skilled in the art will appreciate that functionalization of the nitrogen of cyclic ring formed by $R^4$ and $R^5$ when $R^4$ and $R^5$ together and to the carbon to which they are attached form cyclic rings such as hydantoin A67, urea A68 and lactam A100 may be performed at an appropriate point in the synthesis by deprotonation with a suitable base and reaction of the necessary electrophile to provide the substitutents defined for $R^{35}$. Those skilled in the art will appreciate that a substituted alkyl halide will afford the corresponding substituted $C_1$-$C_6$ alkyl group and treatment with tetrabenzylpyrophosphate, followed by hydrogenation will serve to provide for $R^{35}$=—P(O)(OH)$_2$.

Functionalization of the reduced lactam nitrogen can be performed at an appropriate point in the synthesis by deprotonation with a suitable base and reaction of the necessary electrophile to provide the substitutents defined for $R^{18}$. Those skilled in the art will appreciate that a substituted alkyl halide will afford the corresponding substituted $C_1$-$C_6$ alkyl group and treatment with tetrabenzylpyrophosphate, followed by hydrogenation will serve to provide for $R^{18}$=—P(O)(OH)$_2$.

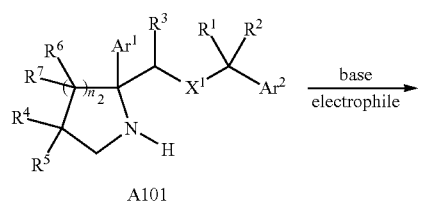

Those skilled in the art will recognize that certain additional protection and deprotection steps may be needed in order to accommodate different functional groups. Accordingly, the order of synthetic operations may be different in order to maintain functional group compatibility with the operational steps in the synthesis.

Specific Methods Of Preparation

EXAMPLES

Example 1a

Example 1b

Step 1:

Compound 1

Compound 1 was prepared using a synthetic procedure reported by M. J. O'Donnell, Z. Fang, X. Ma and J. C. Huffman, *J. Am. Chem. Soc.*, 1997, 46, 617.

Step 2:

Compound 1

Compound 2

To a nitrogen purged solution of oxazolidinone Compound 1 (10.0 g, 0.027 mol, 1equiv) in THF (500 ml) at −78° C., a solution of KHMDS (0.5M in toluene, 64 ml, 0.032 mol, 1.18 equiv) was added. After stirring at −78° C. for 30 min, a solution of bromomethyl ether (11.3 g, 0.032 mol, 1.18 equiv) in THF (100 ml) at −78° C. was cannulated into the reaction mixture. The solution was stirred at −78° C. for 1 h before being quenched with a saturated NH$_4$Cl solution at −78° C.

The reaction mixture was warmed to RT, and water and EtOAc were added. The aqueous layer was extracted with EtOAc (200 ml×2). The combined organic layers were dried (MgSO$_4$) and filtered, and solvents in the filtrate were removed by vacuum. Purification using column chromatography [hexane-toluene, 1:1 (v/v)] gave Compound 2 (11.7 g, 68%) as a colorless oil.

Electrospray MS [M+1]$^+$ 644.1.

Step 3:

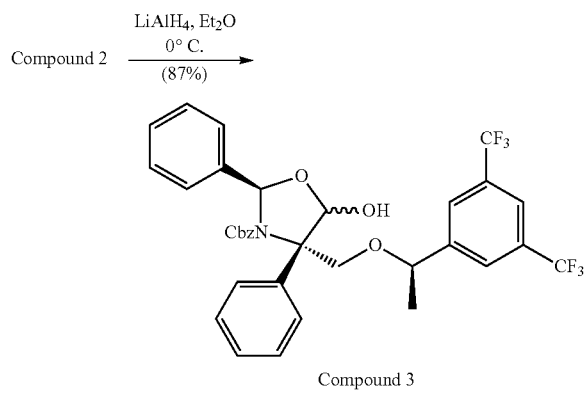

Compound 3

To a solution of lactone Compound 2 (35.2 g, 0.055 mol, 1equiv) in Et$_2$O at 0° C., a 1M solution of LAH (17.8 ml, 0.018 mol, 0.32 equiv) in Et$_2$O was added. The reaction mixture was stirred at 0° C. for 30 min before being quenched with saturated NH$_4$Cl solution. Water was added and the resulting layers were separated. The separated aqueous layer was extracted with EtOAc (300 ml×2), and the combined organic layers were dried (MgSO$_4$), and filtered. Solvents in the filtrate were removed in a vacuum to give a colorless oil. The oil was dissolved in HOAc (240 ml) at RT, and water (60 ml) was added. After being stirred at RT for 1 h, the white solid was filtered, washed with water and dried under a high vacuum. Recrystallization [hexane-toluene] gave Compound 3 (23 g) as a white powder. All filtrates were combined, and the solvents removed in a vacuum to give a yellow oil. The above procedure [HOAc—H$_2$O, followed by recrystallization] was repeated to give another batch of lactol Compound 3 (3 g). Solvents in the filtrate were removed in a vacuum, and the resulting oil was subjected to column chromatography [hexane-EtOAc, 6:1(v/v)] to give a third batch (4 g). The combined yield for Compound 3 was 30 g, 87%.

Electrospray MS [M+1]$^+$ 646.2.

Step 4:

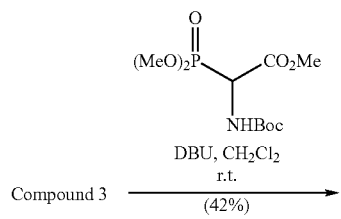

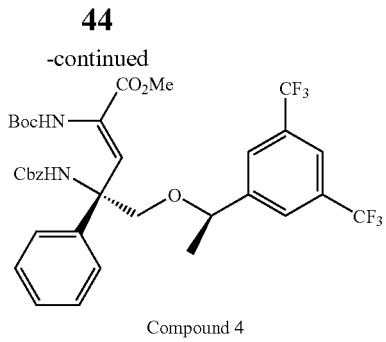

Compound 4

To a solution of Compound 3 (0.98 g, 1.52mmol, 1 equiv) and NBoc-□-phosphonoglycine trimethylester (1.26 g, 3.80mmol, 2.5 equiv) in CH$_2$Cl$_2$ (5 ml) at 23° C., DBU (0.57 ml, 3.80 mmol, 2.5 equiv) was added dropwise. The mixture was stirred at 23° C. for 4 h before it was quenched with saturated NH$_4$Cl solution. Et$_2$O was added and layers were separated. The separated aqueous layer was extracted with Et$_2$O (250 ml×2). The combined organic layers were dried (MgSO$_4$) and filtered. Removal of solvents in vacuum followed by chromatographic purification [hexane:ether, 3:1 (v/v)] gave Compound 4 (587 mg, 52%) as white foam.

Electrospray MS [M+1]$^+$ 745.1.

Step 5:

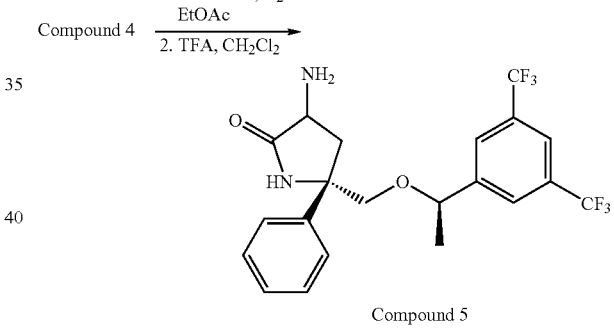

Compound 5

A solution of Compound 4 (1.4 g, 1.88mmol, 1.0 equiv.) in EtOAc (30 ml) was flushed with N$_2$. After the addition of Palladium on carbon (10%, 2 g) a H$_2$ balloon was attached to the reaction flask. The reaction mixture was stirred for 18 h at 23° C. under H$_2$ atmosphere and then filtered and concentrated. The residue was dissolved in anhydrous CH$_2$Cl$_2$ (45 ml), cooled to 0° C., then treated with TFA solution (4.5 ml, 0.059 mmol, 30.0 equiv). The reaction mixture was stirred at 0° C. for 30 min and then at 23° C. for another 4 h. Reaction mixture was diluted with CH$_2$Cl$_2$ (300 ml) washed with saturated NaHCO$_3$ solution (100 ml). The organic layer was dried (Na$_2$SO$_4$), filtered and concentrated to give Compound 5 (0.8 g, 95%).

Step 6:

Compound 5 →$\xrightarrow[90\%]{\text{LAH/AlCl}_3}$

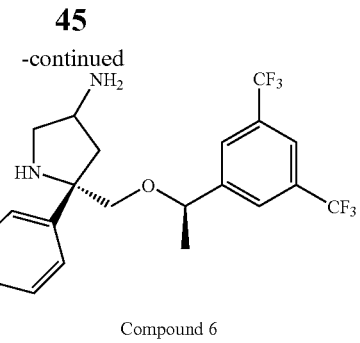

Compound 6

In a flame dry 25 ml RBF was placed AlCl₃ (0.089 g, 0.67 mmol, 1.5 equiv). The reaction flask was cooled to 0° C. and 1 M solution of LAH in Et₂O (2 ml, 1.98 mmol, 4.5 equiv) was carefully added. The reaction mixture was cooled to −78° C. and a solution of Compound 5 (0.2 g, 0.44 mmol, 1.0 equiv) in dry THF (4 ml) was slowly added. The reaction mixture was stirred at −78° C. for 2 h, then slowly warmed to 23° C. and stirred for 18 h. The reaction was then cooled to 0° C. and quenched carefully with saturated aqueous sodium potassium tartrate solution. Reaction mixture was taken up in EtOAc (200 ml) and extracted with saturated aqueous NaHCO₃ (100 ml). Aqueous layer was extracted with EtOAc (150 ml). The combined organic layers were dried over Na₂SO₄, filtered and concentrated to give Compound 6 (180 mg, 95%). Electrospray MS [M+1]⁺ 433.1.

Step 7:

To a solution of Compound 6 (0.21 g, 0.486 mmol, 1.0 equiv) in MeOH (3 ml) at 0° C. was added 2-trifluoromethyl-N,N-diacetylaniline (0.131 g, 0.535 mmol, 1.1 equiv). The mixture was stirred at 0° C. for 1 h, then warmed to 23° C. and stirred for 18 h. The reaction mixture was then concentrated and purified using a Gilson with water/CH₃CN to give a mixture of two compounds (0.16 g). Purification of the mixture by HPLC using ChiralPak column (98:2, hexane:IPA) gave less polar isomer Example 1a (0.050 g, 22%), Electrospray MS [M+1]⁺ 475.1, and more polar isomer Example 1b (0.015 g, 7%), Electrospray MS [M+1]⁺ 475.1.

Preparation of Compound 9:

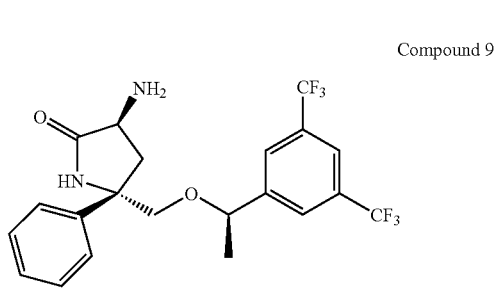

Compound 9

Step 1:

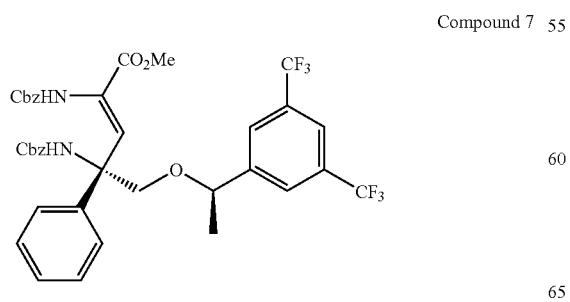

Compound 7

Compound 7 was prepared using a procedure similar to that for Compound 4, using Compound 3 and PO(OEt)₂CH(NH-Cbz)CO₂Me in place of PO(OMe)₂CH(NHBOC)CO₂Me. Electrospray MS [M+1]¹⁺ 745.1.

Step 2:

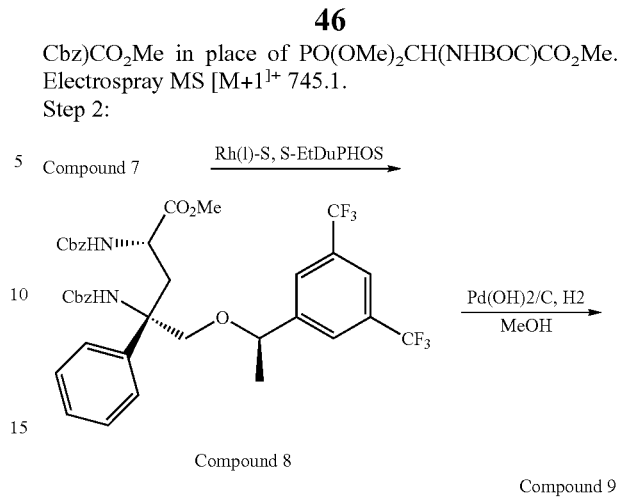

Compound 7 (3.0 g, 4.03 mmol, 1.0 equiv) was taken in MeOH (30 ml) in a parr reaction bottle. The reaction bottle was degassed using N₂ for 15 min. (+)-1,2-Bis-((2S,5S)-2,5-diethylphospholano) benzene (cyclooctadiene)rhodium(l) trifluoro-methanesulfonate (0.12 g, 0.16 mmol, 0.04 equiv) was added to the reaction mixture in a glove box, and shaken under H₂ at 60 psi for 96 h. The reaction mixture was transferred to a 200 ml RBF. 20% of Pd(OH)₂/C (1 g) was added to the reaction mixture, which was stirred under H₂ at 23° C. for 18 h. The reaction was monitored by TLC 9/1 EtOAc/CH₃OH. Once the reaction was completed it was filtered through celite and concentrated. Purification was carried out using a silica plug 9:1 EtOAc/MeOH(NH₃) to give the Compound 9 (1.3 g, 72%).

Electronspray MS [M+1]⁺ 447.1.

Preparation of Compound 10:

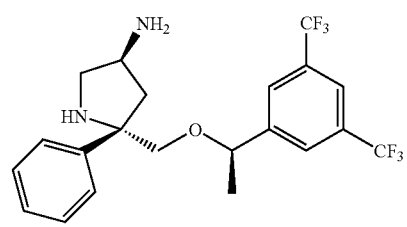

Compound 10

Compound 10 was prepared using similar procedure to Compound 6, using Compound 9 instead of Compound 5.

Example 2

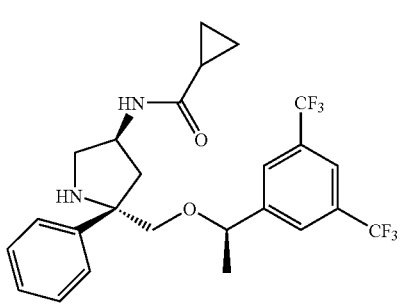

To a solution of Compound 10 (0.05 g, 0.116 mmol, 1.0 equiv) in MeOH (2 ml) at −78° C. was added cyclopropanecarbonyl chloride (12 µl, 0.127 mmol, 1.1 equiv). The mixture was stirred at −78° C. for 5 min, then warmed to 23° C. and stirred for 18 h. The reaction mixture was then concentrated and taken up in EtOAc (200 ml) and washed with sat. aq. NaHCO$_3$ (1×100 ml). The organic layer was dried over Na$_2$SO$_4$, filtered and concentrated. Purification of the resulting mixture on a Biotage with 5% MeOH/EtOAc gave Example 2 (0.04 g, 69%). Electrospray MS [M+1]$^+$ 501.

Example 3

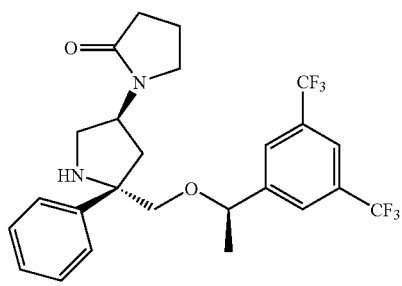

Step 1:

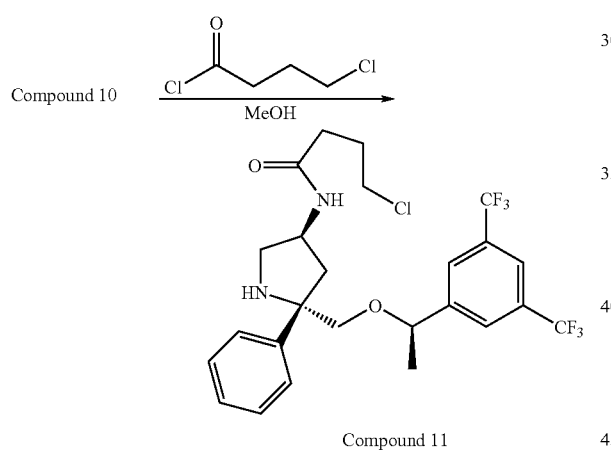

Compound 11

To a solution of Compound 10 (0.05 g, 0.116 mmol, 1.0 equiv) in MeOH (2 ml) at −78° C. was added 4-chlorobutyryl chloride (14 µl, 0.127 mmol, 1.1 equiv). The mixture was stirred at −78° C. for 5 min, then warmed to 23° C. and stirred for 18 h. The reaction mixture was then concentrated and taken up in EtOAc (200 ml) and washed with sat. aq. NaHCO$_3$ (1×100 ml). The organic layer was dried over Na$_2$SO$_4$, filtered and concentrated to provide the crude Compound 11, which was used in the next reaction without further purification.

Step 2:
To a solution of crude Compound 11 in dry THF (2 ml) was added NaH (60% dispersion in mineral oil, 0.014 g, 0.347 mmol, 3 equiv) at 0° C. and stirred for 5 min, then heated at 60° C. for 2 h. The reaction mixture was cooled to 0° C. and quenched carefully with water (3 ml). The mixture was poured into EtOAc (100 ml) and washed with saturated aqueous NaHCO$_3$ (100 ml). The organic layer was dried over anhydrous Na$_2$SO$_4$, filtered and concentrated. Purification of the resulting mixture on Biotage with 5% MeOH/EtOAc gave Example 3 (0.20 g, 34%).
Electrospray MS [M+1]$^+$ 501.1.

Example 4

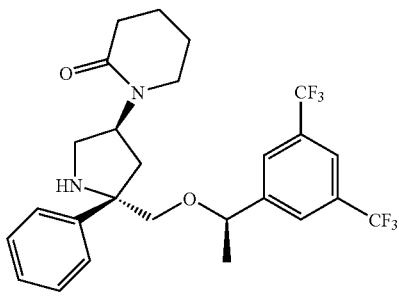

Example 4 (53% overall yield) was prepared from Compound 10 in a manner similar to that used to prepare the Example 3, but using 5-chlorovaleryl chloride in place of 4-chlorobutyryl chloride. Electrospray MS [M+1]$^+$ 515.1.

Example 5

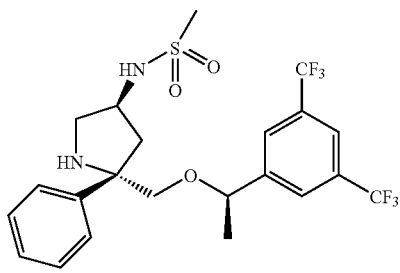

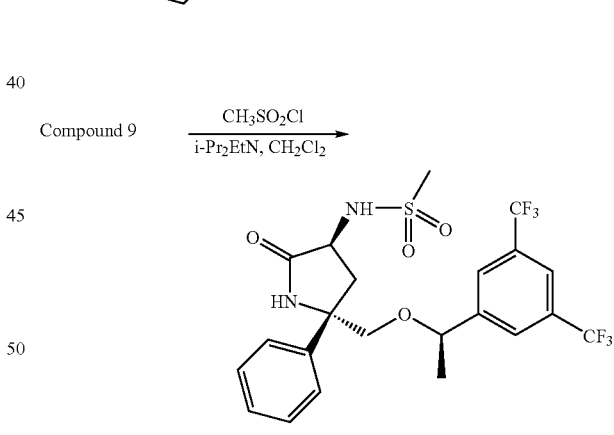

Compound 12

To a solution of Compound 9 (0.13 g, 0.29 mmol, 1.0 equiv) in CH$_2$Cl$_2$ (3 ml) at 0° C. was added DIEA (0.11 ml, 0.61 mmol, 2.1 equiv) and CH$_3$SO$_2$Cl (34 µl, 0.435 mmol, 1.5 equiv). The mixture was stirred at 0° C. for 30 min, then poured into EtOAc (150 ml) and washed with saturated aqueous NaHCO$_3$ (100 ml). The organic layer was dried over anhydrous Na$_2$SO$_4$, filtered and concentrated to provide the crude Compound 12, which was used in the next reaction without further purification.

The crude Compound 12 was converted to Example 5 (80 mg, 54% yield, two steps from Compound 9) using a method similar to the preparation Compound 6 from Compound 5. Electrospray MS [M+1]⁺ 511.1.

Example 6a and Example 6b

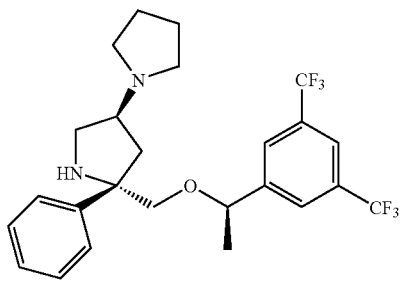
Example 6a

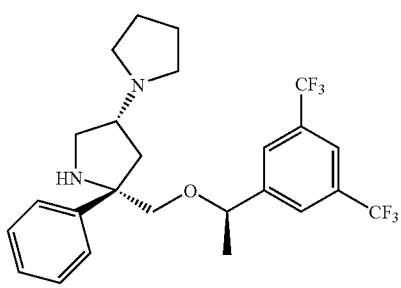
Example 6b

Step 1:

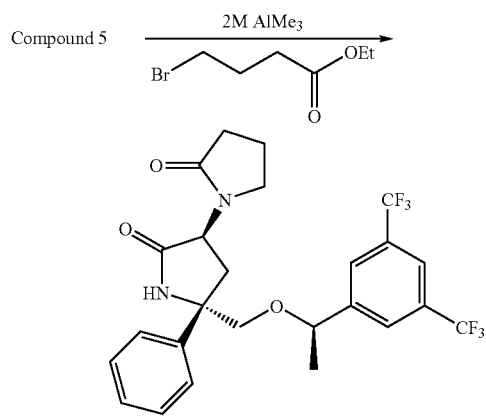

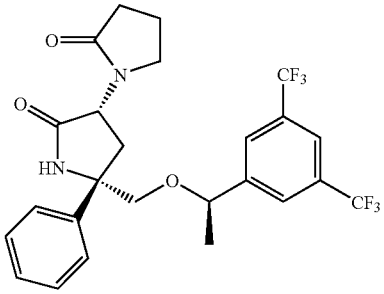
Compound 13b

To a solution of amino-lactam Compound 5 (0.100 g, 0.224 mmol, 1 equiv) in toluene (7 ml) at 0° C., was added a solution of 2M AlMe₃ in toluene (0.14 ml, 0.28 mmol, 1.25 equiv). The reaction mixture was warmed to RT and stirred for 15 min. Ethyl 4-bromobutyrate was added, and the resulting mixture was heated at 100° C. for 18 h. The reaction mixture was cooled to RT, poured into EtOAc (20 ml), and washed with of saturated aqueous NaHCO₃ (100 ml) and saturated aqueous NaCl (100 ml) successively. The organic layer was dried over anhydrous Na₂SO₄, filtered, and concentrated. HPLC separation on ChiralCel OD column using a (90/10) hexane/IPA mixture gave the Compound 13a (40 mg, 35%), and the Compound 13b (20 mg, 18%).

Electrospray MS [M+1]⁺ 515.1 for the Compound 13a.

Electrospray MS [M+1]⁺ 515.1 for the Compound 13b.

Example 6a and Example 6b were prepared using a procedure similar to Compound 6, using Compound 13a and 13b instead of Compound 5.

Electrospray MS [M+1]⁺ 487.11 for the Example 6a.

Electrospray MS [M+1]⁺ 487.11 for the Example 6b.

Example 7

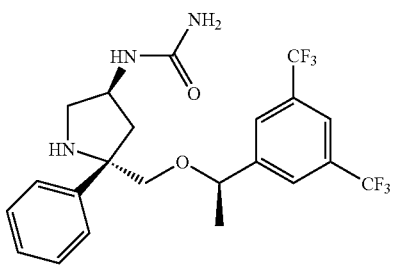

Example 7 (74% overall yield) was prepared from Compound 10 in a manner similar to that used to prepare Example 29 from Example 13.

Electrospray MS [M+1]¹⁺ 476.1.

Example 8

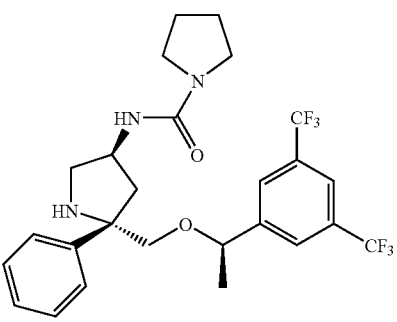

Example 8 (94% overall yield) was prepared from Compound 10 in a manner similar to that used to prepare Example 33 from Example 13.

Electrospray MS [M+1]⁺ 430.1.

Example 9

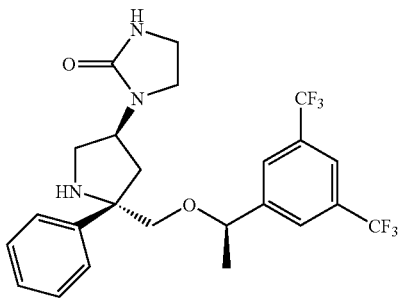

Example 9 (50% overall yield) was prepared from Compound 10 in a manner similar to that used to prepare Example 36 from Example 13.

Electrospray MS [M+1]$^+$ 502.1.

Example 10

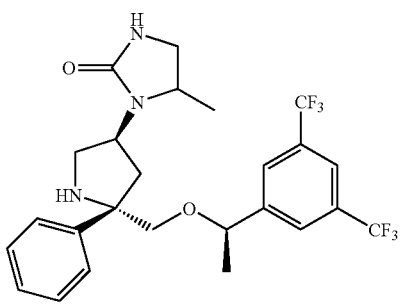

To a solution of Compound 10 (0.15 g, 0.3 mmol, 1 equiv) in CH$_2$Cl$_2$ (2 ml) was added methyl levulinate (0.041 ml, 0.33 mmol, 1.1 equiv) followed by sodium triacetoxyborohydride (0.127 g, 0.6 mmol, 2 equiv.) and the reaction mixture was stirred at 23° C. and stirred for 72 h. The reaction was quenched with saturated aq. NaHCO$_3$ (100 ml) and extracted with EtOAc (200 ml). The organic layer was separated, dried (Na$_2$SO$_4$), filtered and concentrated. The mixture was purified by chromatography over Gilson (1:9, water:CH$_3$CN) to give the title compound (0.070 g, 47%). (Electrospray MS [M+1]$^+$ 515.1.

Example 11

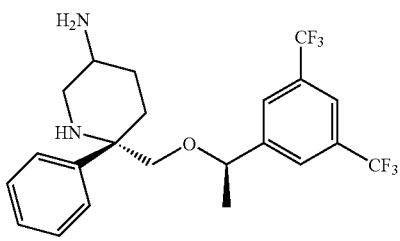

Step 1:

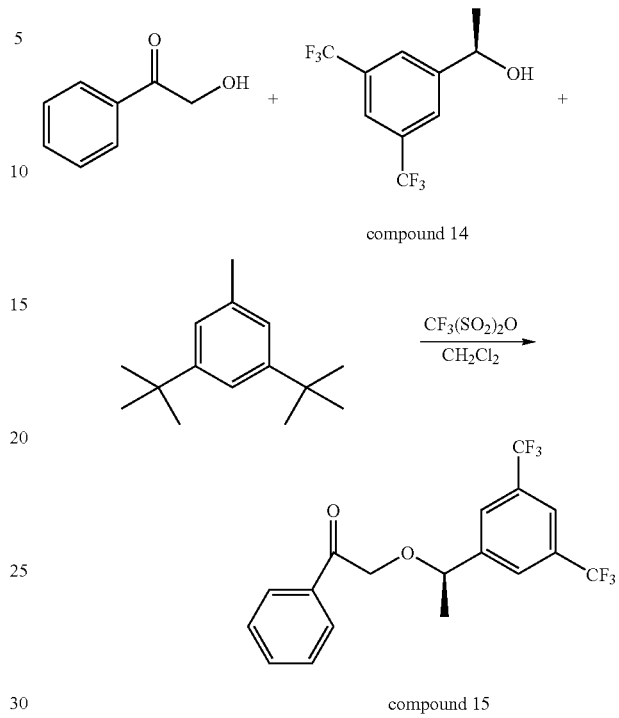

Procedures for preparing Compound 14 and Compound 15 are shown in WO 01/44200.

Step 2:

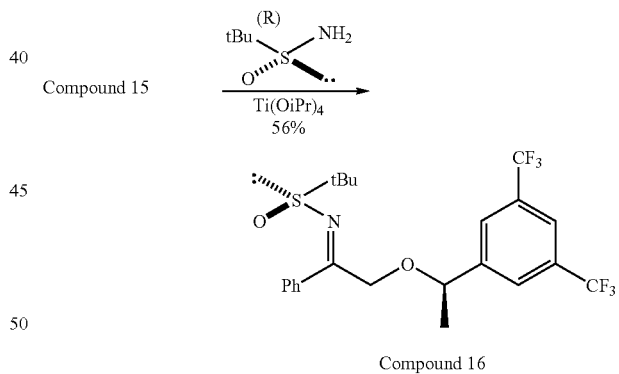

To a flask containing ketone Compound 15 (1.05 g, 2.8 mmol, 1 equiv) and (R)-t-butylsulfinamide (0.4 g, 3.3 mmol, 1.8 equiv), was applied a vacuum for 5 min. Then, the flask was filled with N$_2$. Ti(OiPr)$_4$ (1 ml) was added through a syringe dropwise to the reaction mixture. The reaction mixture was stirred at 23° C. for 36 h. The reaction mixture was then poured into brine (10 ml) and EtOAc (20 ml) and stirred vigorously for 10 min. The resulting suspension was passed through a pad of celite 545. The celite pad was washed with EtOAc several times. The combined organic solution was dried and concentrated under reduced pressure. Flash column chromatography afforded Compound 16 (0.75 g, 56%).

Step 3:

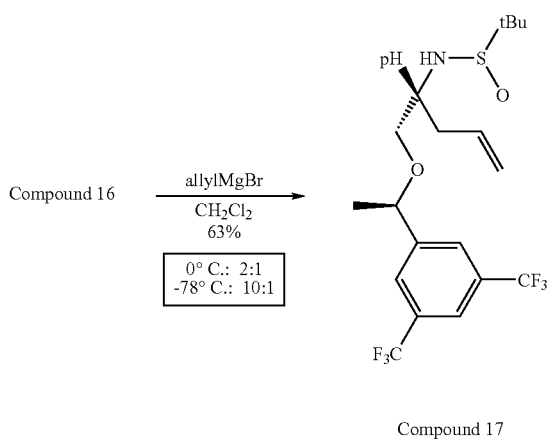

Compound 16 →(allylMgBr, CH₂Cl₂, 63%)→ Compound 17

[0° C.: 2:1; −78° C.: 10:1]

To a solution of sulfinimine Compound 16 (2.44 g, 5.1 mmol, 1 equiv) in CH₂Cl₂ at −78° C., was added dropwise allylmagnesium bromide (6.1 ml, 6.1 mmol, 1.2 equiv, 1 M in Et₂O) through a syringe. After stirring for 3 h at −78° C., the reaction mixture was quenched with a saturated aqueous NH₄Cl and allowed to warm to 23° C. The layers were separated, and the aqueous layer was extracted with EtOAc. The combined organic layers were dried and concentrated. Flash column chromatography gave Compound 17 (1.672 g, 63%).

Step 4:

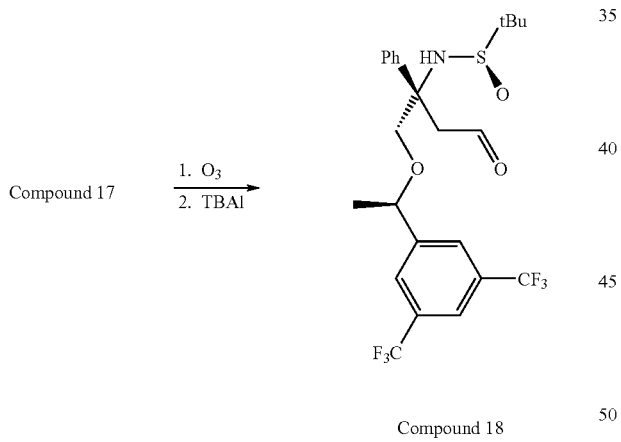

Compound 17 →(1. O₃; 2. TBAI)→ Compound 18

A 15 ml RBF was charged with Compound 17 (245 mg, 0.47 mmol, 1.0 equiv) and CH₂Cl₂ (2 ml). This pale orange solution was cooled to −78° C., and then O₃ was bubbled in at 1.0 ml/min. After the solution turned pale blue, the reaction solution was stirred at −78° C. for 10 min. Then it was flushed with N₂ to get rid of O₃. Tetrabutylammonium iodide (177 mg, 0.47 mmol, 1.0 equiv) was added to break the complex. Then it was quenched with saturated Na₂S₂O₃, and extracted with CH₂Cl₂. The combined organic layers were dried, filtered, and concentrated, then re-taken up with Et₂O and filtered. The residue on the filter was dissolved in water and extracted with Et₂O. The combined Et₂O layer was dried, filtered and concentrated to give Compound 18 (243.5 mg, 99%). Electrospray MS [M+1]⁺ 524.1.

Step 5:

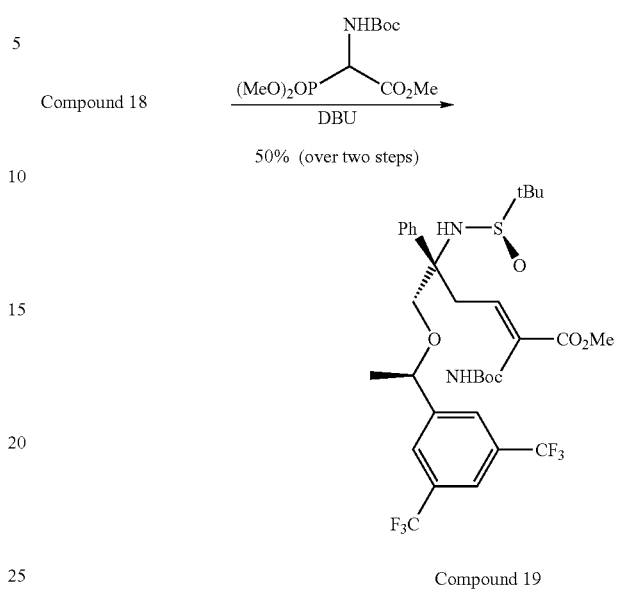

Compound 18 →((MeO)₂OP–C(NHBoc)–CO₂Me, DBU, 50% (over two steps))→ Compound 19

To a solution of Compound 18 (1.2 g, 2.29 mmol, 1.0 equiv) Boc-Phosphonate (818 mg, 2.75 mmol, 1.2 equiv) in DMF (20 ml) was added Cs₂CO₃ (2.24 g, 6.87 mmol, 3.0 equiv). After stirring at RT for 3 h, the mixture was diluted with Et₂O, and washed with water (100 ml 2×), and brine. The combined aqueous layer was further extracted with Et₂O. The combined organic layer was dried, filtered and concentrated to give crude brownish oil, which was purified by column to give Compound 19 (830 mg, 55%). Electrospray MS [M+1]⁺ 695.2.

Step 6:

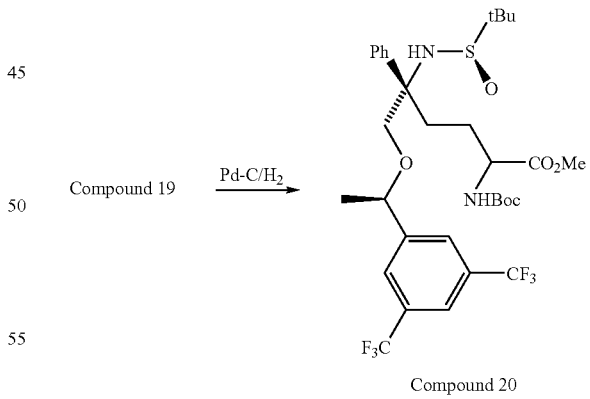

Compound 19 →(Pd-C/H₂)→ Compound 20

A solution of Compound 19 (830 mg, 1.19 mmol, 1.0 equiv) in EtOH (20 ml) was flushed with N₂. After the addition of Palladium on carbon (10%, 1.27 g, 1.19 mmol, 1.0 equiv), a H₂ balloon was attached to the reaction flask. The reaction mixture was stirred for almost 24 h until TLC showed completion of the reaction. The mixture was filtered and concentrated to give Compound 20 as white solid (790 mg, 95%). Electrospray MS [M+1]⁺ 697.2.

Step 7:

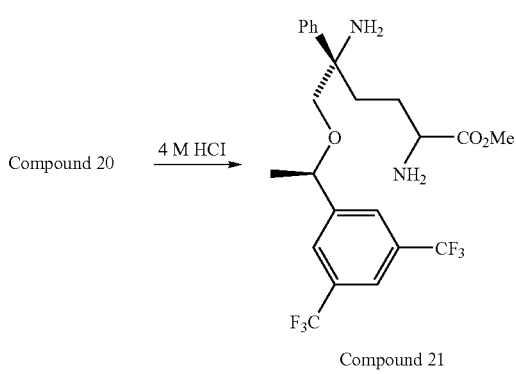

A solution of Compound 20 (400 mg, 0.57 mmmol, 1.0 equiv) in anhydrous MeOH (4 ml) was cooled to 0° C., then treated with 4 M solution of HCl in 1,4-dioxane (16 ml). After 30 min at 0° C., it was stirred at RT for another 3 h. The solvent was evaporated under vacuum to give Compound 21 as pale brown solid. Electrospray MS [M+1]$^+$ 493.1.

Step 8:

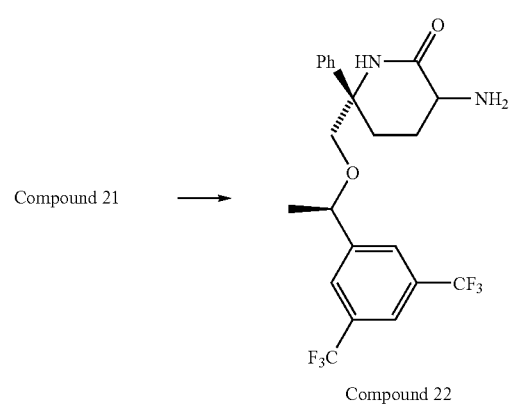

To a solution of Compound 21 in MeOH (50 ml) was added $K_2CO_3$ (4.5 g). The mixture was stirred for 30 min, then filtered and concentrated to give Compound 22 (199 mg, 76%). Electrospray MS [M+1]$^+$ 461.1.

Step 9:

A flame-dried 500 ml RBF was charged with $ALCl_3$ (37.4 mg, 0.28 mmol, 1.5 equiv). The reaction flask was cooled to 0° C. and anhydrous THF (1 ml) was syringed in. After stirred for 5 min, 1 M solution of LAH in $Et_2O$ (0.84m1, 0.84 mmol, 4.5 equiv) was cannulated in. The ice-bath was removed and the solution was stirred at RT for 30 min. Then the reaction mixture was cooled to −78° C. and a solution of Compound 22 (50 mg, 0.187 mmol, 1.0 equiv) in dry THF (1 ml) was slowly added. The reaction mixture was stirred at −78° C., and allowed to warm up to RT overnight. After TLC (MeOH/ $CH_2Cl_2$=1/9) indicated the reaction was completed, the reaction was then cooled to 0° C. and diluted with EtOAc and quenched carefully with saturated aqueous sodium potassium tartarate solution. It was stirred at RT for over 30 min to get separation of the two layers. The aqueous layer was further extracted with EtOAc. The combined organic layer was dried over $Na_2SO_4$, filtered and concentrated to give Example 11 (34 mg, 41%). Electrospray MS [M+1]$^+$ 447.1.

Example 12a and Example 12b

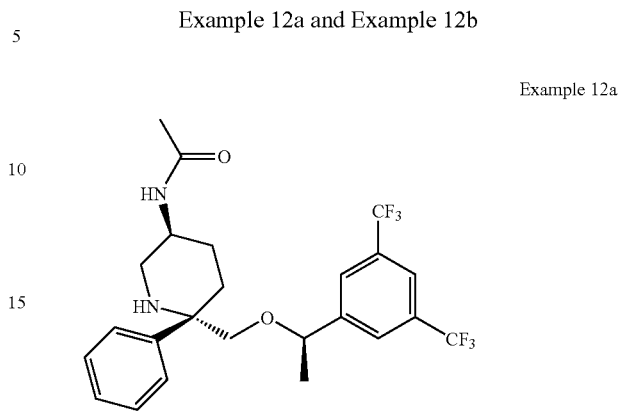

Example 12a

Example 12b

Step 1:

To a solution of Example 11 (30 mg, 0.067 mmol, 1.0 equiv) in $CH_2Cl_2$ (10 ml) at 0° C. was added DIEA(17.5 µl, 0.10 mmol, 1.5 equiv) and $Ac_2O$ (6.3 µl, 0.067 mmol, 1.0 equiv). The mixture was stirred at 0° C. for 30 min. It was quenched with saturated aqueous $NaHCO_3$ solution (4 ml) and extracted with $CH_2Cl_2$. The combined organic layers were dried, filtered and concentrated to give the crude product (39 mg). Purification of the mixture by HPLC using Chiral-Pak AD column (2:98, IPA:hexane) gave more polar isomer Example 12a, Electrospray MS [M+1]$^+$ 489.1, and less polar isomer Example 12b, Electrospray MS [M+1]$^+$ 489.1.

Example 13

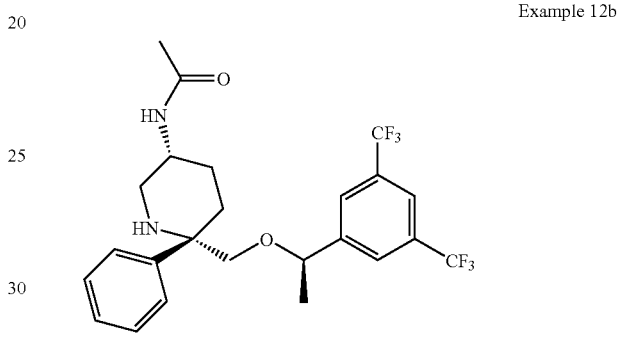

Step 1:

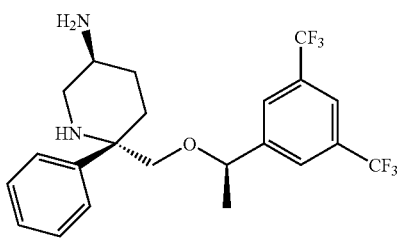

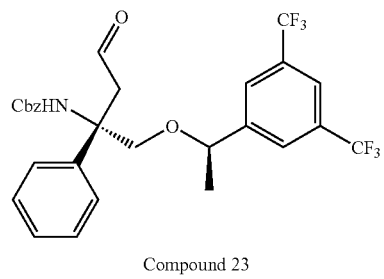

Compound 23

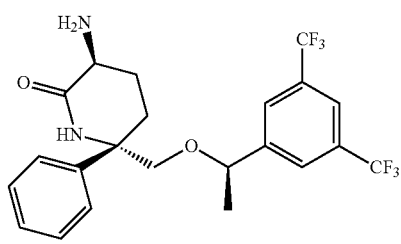

Compound 25

Step 3:

Compound 25 was prepared using a procedure similar to that for Compound 9 using Compound 24 instead of Compound 7. Electrospray MS [M+1]$^+$ 461.1.

Step 4:

Example 13 (6.84 g, 73%) was prepared using similar procedure to Compound 6 using Compound 25 instead of Compound 5.

Electrospray MS [M+1]$^+$ 447.1.

Example 14

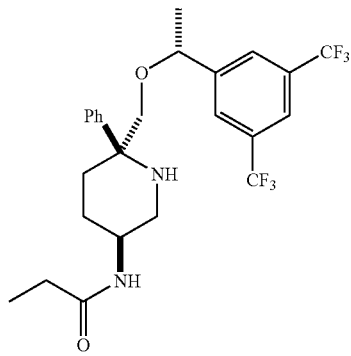

To a solution of Example 13 (275 mg, 0.60 mmol, 1.0 equiv) in anhydrous CH$_2$Cl$_2$ (10 ml) at −78° C. was added propionyl chloride (52 μl, 0.60 mmol, 1.0 equiv). The reaction was completed within 30 min. Reaction mixture was quenched with 7N ammonia in MeOH (0.5 ml), then loaded directly onto silica column and purified to give Example 14. (241.3 mg, 80%). Electrospray MS [M+1]$^+$ 503.1.

Example 15

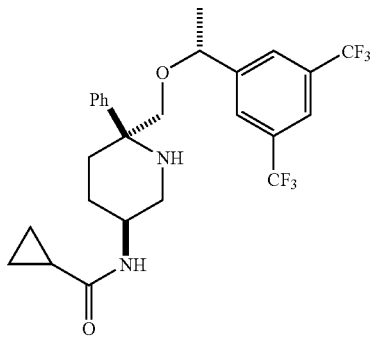

To a suspension of (methoxymethyl)triphenylphosphonium chloride (21.3 g, 0.062 mmol, 2.95 equiv) in toluene (300 ml) at 0° C. under N$_2$, a solution of potassium bis(trimethylsilyl)amide (125 ml, 0.062 mmol, 2.95 equiv) was added. After being stirred at 0° C. for 1 h, a solution of Compound 3 (13.4 g, 0.021 mmol, 1 equiv) in toluene (100 ml) was added. The mixture was allowed to stir from 0° C. to 23° C. in 1 h and then was quenched with saturated NH$_4$Cl solution. Et$_2$O was added and layers were separated. The separated aqueous layer was extracted with Et$_2$O (400 ml×2). The combined organic layers were dried (MgSO$_4$) and filtered. Solvents were removed in vacuum to give crude enol ether as yellow oil.

The crude enol ether was dissolved in THF (100 ml) at 23° C. and aqueous HCl (100 ml, 10% in water) was added. The mixture was stirred overnight and was quenched with saturated KHCO$_3$ solution. Et$_2$O was added and layers were separated. The separated aqueous layer was extracted with Et$_2$O (300 ml×2). The combined organic layers were dried (MgSO$_4$) and filtered. Removal of solvents in vacuum followed by chromatographic purification [hexane:EtOAc, 4:1 (v/v)] gave Compound 23 (6.97 g, 61 %) as yellow oil.

Step 2:

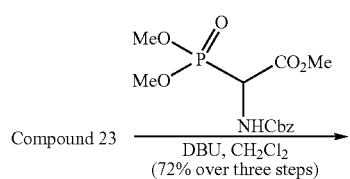

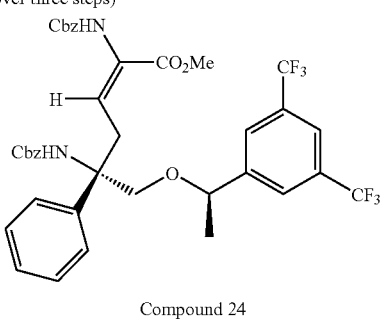

Compound 24

Compound 24 was prepared from Compound 23 using a procedure similar to the preparation of Compound 4 from Compound 3 and using PO(OEt)$_2$CH(NHCbz)CO$_2$Me in place of PO(OMe)$_2$CH(NHBoc)CO$_2$Me.

Example 15 (yield 89%) was prepared using similar procedure as for Example 14 using cyclopropanecarbonyl chloride in place of propionyl chloride.
Electrospray MS [M+1]+ 515.1.

Example 16

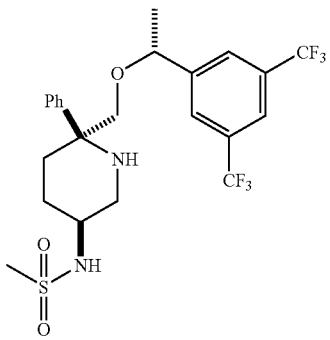

Example 16 (yield 89%) was prepared using similar procedure as for Example 14 using Example 13 and CH$_3$SO$_2$Cl in place of propionyl chloride.
Electrospray MS [M+1]+ 52.1.

Example 17

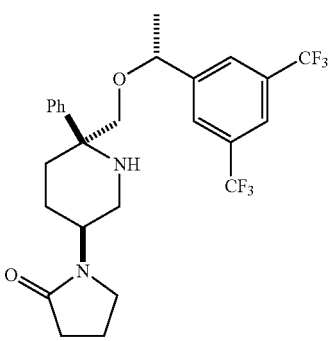

Example 17 (overall yield 23%) was prepared using similar procedure as for Example 3 using Example 13 in place of Compound 10.
Electrospray MS [M+1]+ 515.1.

Example 18

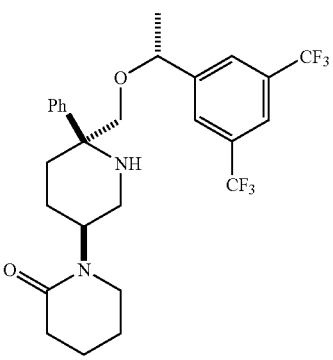

Example 18 (overall yield 42%) was prepared using similar procedure as for Example 4 using Example 13 in place of Compound 10.
Electrospray MS [M+1]+ 529.1.

Preparation of Compounds 26, 27, 28 and 29:

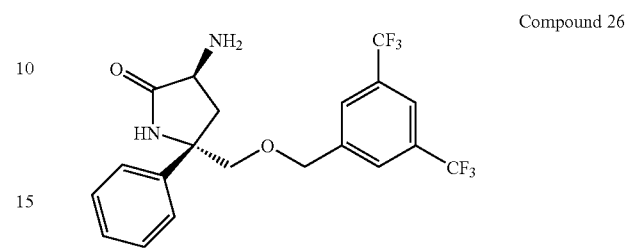

Compound 26

Compound 26 was prepared from Compound 1 using similar procedure as for Compound 9.

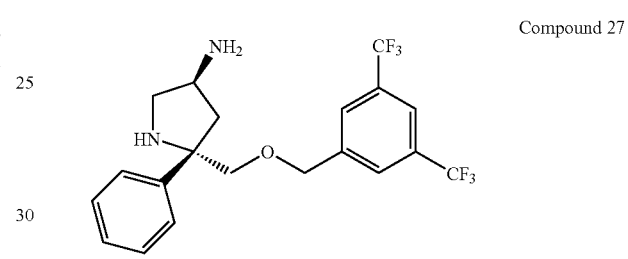

Compound 27

Compound 27 was prepared using similar procedure as for Compound 10.

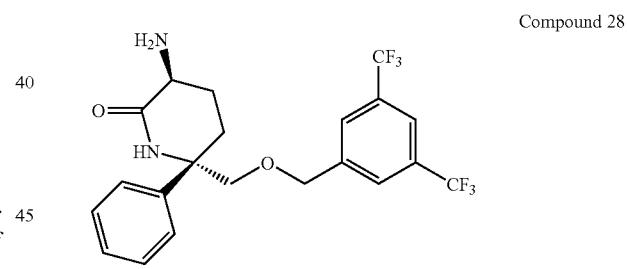

Compound 28

Compound 28 (90% yield) was prepared using the similar procedure for Compound 25. Electrospray MS [M+1]+ 447.1.

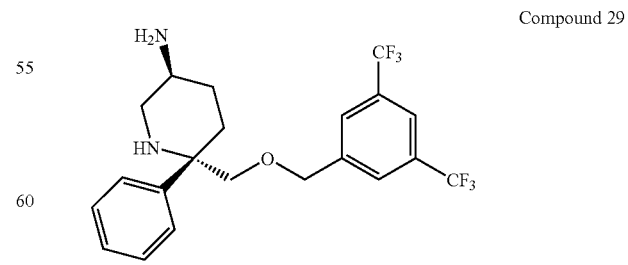

Compound 29

Compound 29 was prepared using similar procedure as for Example 13.
Electrospray MS [M+1]+ 433.1.

Example 19

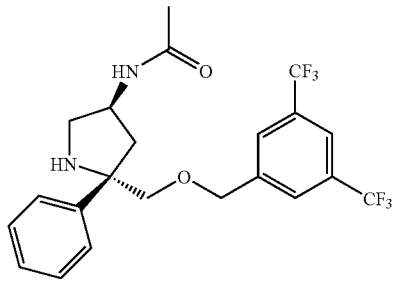

Example 19 (40 mg, 70% yield) was prepared using a procedure similar to Example 1a using Compound 27 instead of Compound 6.

Electrospray MS [M+1]$^+$ 461.1.

Example 20

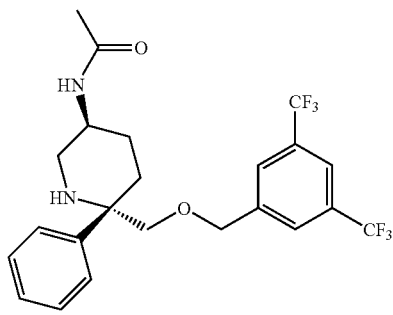

Example 20 (99 mg, 72%) was prepared using similar procedure as for Example 1a using Compound 29 instead of Compound 6.

Electrospray MS [M+1]$^+$ 475.1.

Example 21

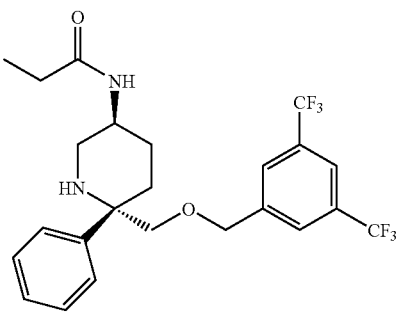

Example 21 (74 mg, 66%) was prepared from Compound 29 using similar procedure as for Example 2 from Compound 10 using propionic anhydride in place of cyclopropanecarbonyl chloride. Electrospray MS [M+1]$^+$ 489.1.

Example 22

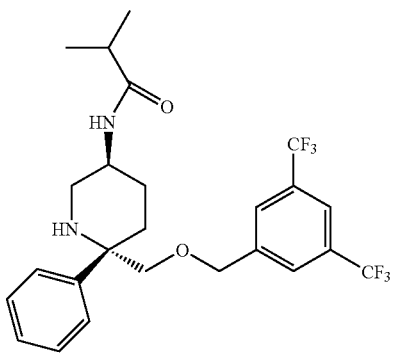

Example 22 (75 mg, 78%) was prepared from Compound 29 using similar procedure as for Example 2 from Compound 10 using isobutyryl chloride in place of cyclopropanecarbonyl chloride. Electrospray MS [M+1]$^+$ 503.1.

Example 23

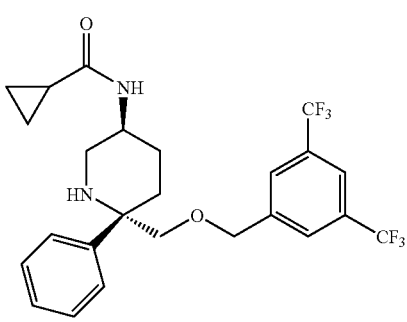

Example 23 (9 mg, 35%) was prepared from Compound 29 using similar procedure as for Example 2 from Compound 10. Electrospray MS [M+1]$^+$ 501.1.

Example 24

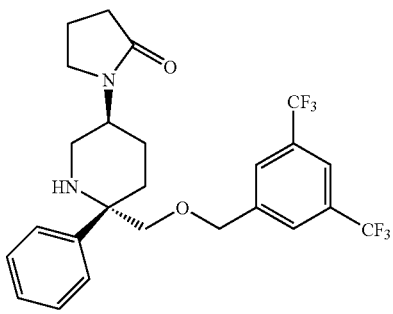

Example 24 (31 mg, 71 %) was prepared from Compound 29 using similar procedure as for Example 3 from Compound 10. Electrospray MS [M+1]+ 501.1.

Example 25

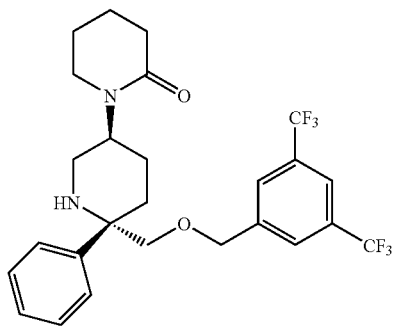

Example 25 (68 mg, 68%) was prepared from Compound 29 using similar procedure as for Example 4 from Compound 10. Electrospray MS [M+1]+ 515.1.

Example 26

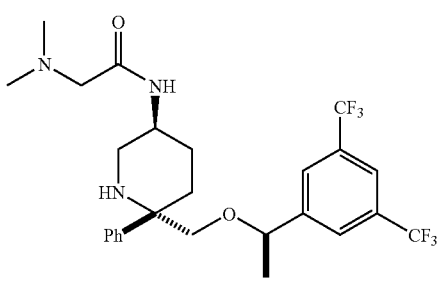

To a solution of Example 13 (0.14 g, 0.314 mmol, 1 equiv) in anhydrous DMF (1.6 ml) at 23° C. was added N,N-dimethyl glycine (33.95 mg, 0.329 mmol, 1.05 equiv) followed by EDC.HCl (66.13 mg, 0.345 mmol, 1.1 equiv) and the reaction mixture was stirred at 23° C. for 18 h. The reaction mixture was diluted with DMF (2.4 ml) and purified using Gilson to give Example 26 (66 mg, 40%). Electrospray MS [M+1]+ 532.1.

Example 27

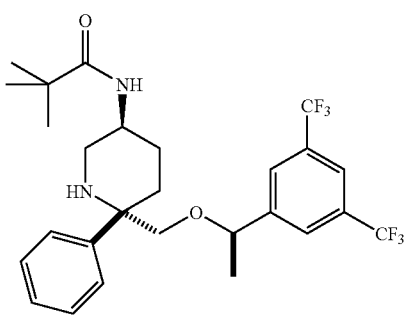

Example 27 (yield 62%) was prepared using similar procedure as for Example 14 using trimethylacetyl chloride in place of propionyl chloride.
Electrospray MS [M+1]+ 531.1

Example 28

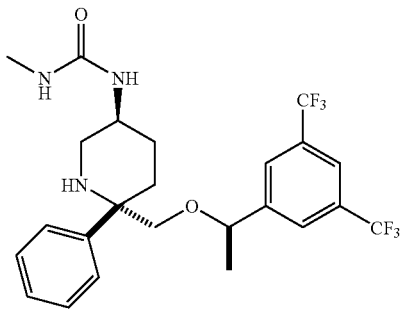

Example 28 (105 mg, 74%) was prepared using similar procedure as for Example 14 using methyl isocyanate in place of propionyl chloride.
Electrospray MS [M+1]+ 504.1

Example 29

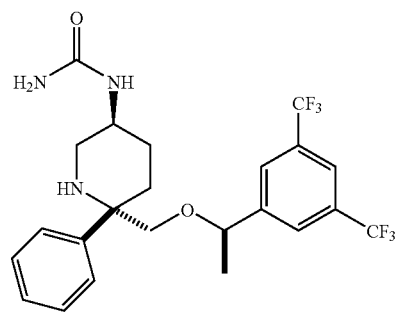

Example 29 (146 mg, 754%) was prepared using similar procedure as for Example 14 using trimethylsilyl isocyanate in place of propionyl chloride.
Electrospray MS [M+1]+ 490.1

Example 30

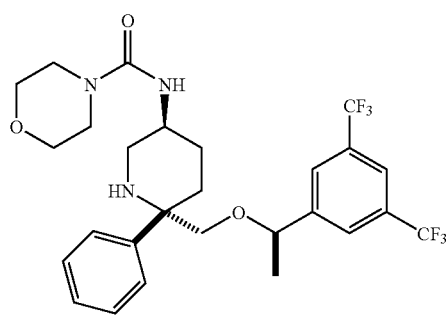

To a solution of Example 13 (100 mg, 0.224 mmol, 1 equiv) in anhydrous CH$_2$Cl$_2$ (2 ml) was added 4-morpholinylcarbonyl chloride (28.7 µl, 0.246 mmol, 1.1 equiv) and DIEA (39 µl, 0.223 mmol, 1 equiv). The reaction mixture was stirred at RT overnight. Aqueous work-up and purification by using silica column to afford Example 30 (53 mg, 42%). Electrospray MS [M+1]+ 560.1

Example 31

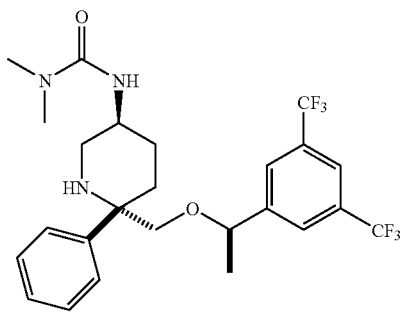

Example 31 (40% yield) was prepared using similar procedure as for Example 30 using dimethylcarbamyl chloride in place of 4-morpholinylcarbonyl chloride. Electrospray MS [M+1]+ 518.1

Example 32

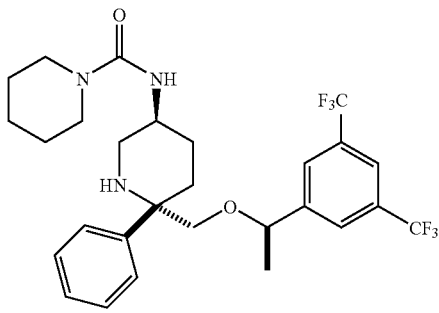

Example 32 (42% yield) was prepared using similar procedure as for Example 30 using 1-piperidinecarbonyl chloride in place of 4-morpholinylcarbonyl chloride. Electrospray MS [M+1]+ 558.1

Example 33

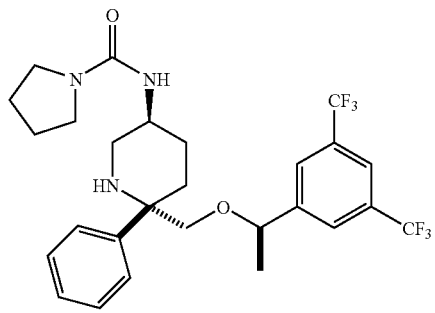

Example 33 (40% yield) was prepared using similar procedure as for Example 30 using 1-pyrrolidinecarbonyl chloride in place of 4-morpholinylcarbonyl chloride. Electrospray MS [M+1]+ 544.1

Example 34

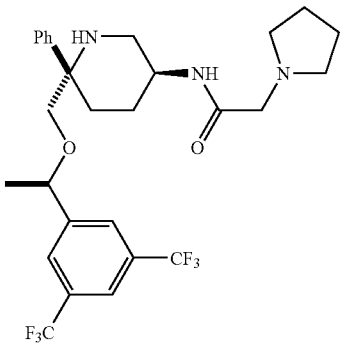

Step 1:

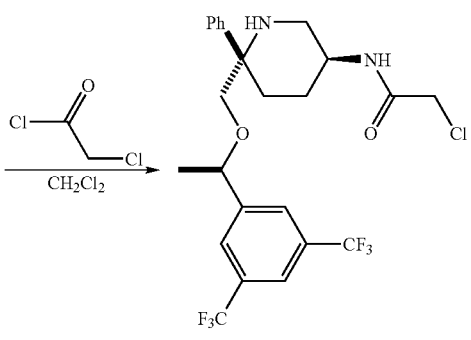

Compound 30

Compound 30 (43% yield) was prepared using similar procedure as for Example 10 using chloroacetyl chloride in place of propionyl chloride.

Step 2:

To a solution of Compound 30 (90 mg, 0.17 mmol, 1 equiv) in anhydrous $CH_2Cl_2$ (0.5 ml) was added pyrrolidine (17.2 μl, 0.206 mmol, 1.2 equiv) and DIEA (30 μl, 0.17 mmol, 1 equiv). The reaction mixture was stirred at RT overnight. Aqueous work-up and purification by using silica column to afford Example 34 (45 mg, 47%).

Electrospray MS [M+1]+ 558.1.

Example 35   Example 36

Example 35

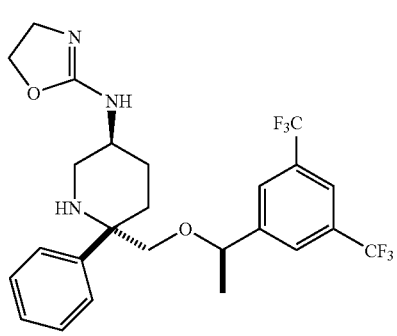

-continued

Example 36

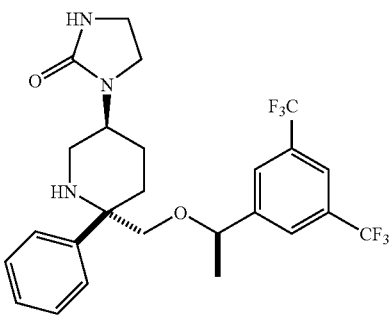

Step 1:

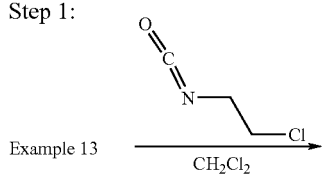

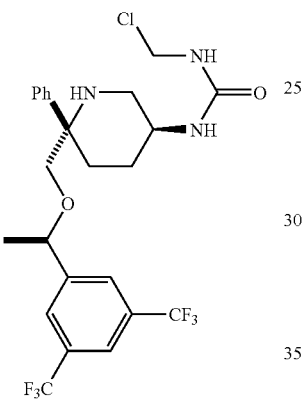

Compound 31

Compound 31 was prepared using similar procedure as for Example 14 using 2-chloroethyl isocyanate in place of propionyl chloride.

Step 2:

To a solution of Compound 31 in anhydrous THF (7 ml), was added NaH (25 mg, 0.625 mmol, 1.7 equiv, 60% dispersion in mineral oil) at 0° C. The resulting cloudy solution was heated at 60° C. for 2 h. Aqueous work-up to give the crude product which was purified by silica gel column to give the less polar title compound Example 35 (10 mg, 5.4%), Electrospray MS [M+1]⁺ 516.1; and the more polar title compound Example 36 (122 mg, 66%), Electrospray MS [M+1]⁺ 516.1

Example 37

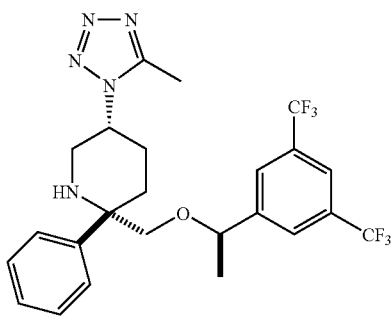

To a solution of Example 12b (200 mg, 0.41 mmol, 1 equiv) in anhydrous $CH_2Cl_2$ (1 ml) at 0° C., was added trifluoromethanesulfonic anhydride (69 µl, 0.41 mmol, 1 equiv). The reaction mixture was stirred for 40 min before $NaN_3$ (26.6 mg, 0.41 mmol, 1 equiv) was added. The mixture was warmed up to RT for 2 h. The solvent was removed in vacuum. The residue was purified with prep-TLC (silica) to obtain Example 37 (4.5 mg, 2%). Electrospray MS [M+1]⁺ 514.1

Example 38

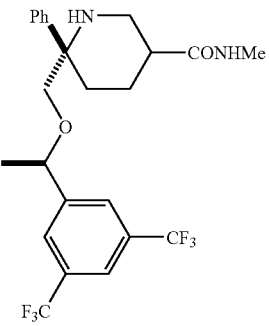

Step 1:

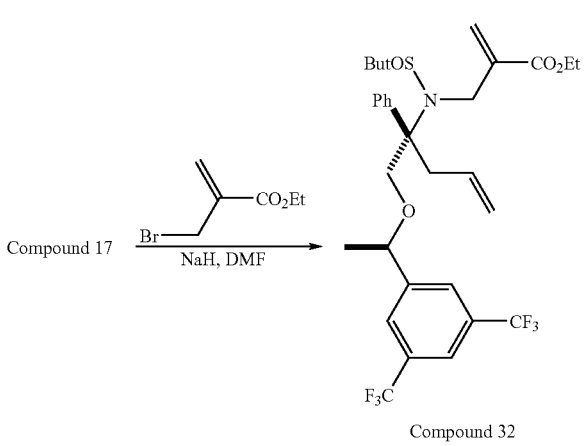

Compound 32

To Compound 17 (0.3 g, 0.575 mmol, 1 equiv) under $N_2$ in anhydrous DMF (3 ml) at 0° C. was added NaH (27.6 mg, 0.69 mmol, 1.2 equiv, 60% in mineral oil) and the reaction mixture was stirred for 1 h. To the resulting suspension under vigorous stirring was dropwise added ethyl-2-bromomethylacrylate (0.088 ml, 0.629 mmol, 1.1 equiv). The reaction mixture was allowed to warm to 23° C. and stirred for 18 h. The reaction was quenched with saturated aqueous $NH_4Cl$ solution and extracted with $Et_2O$. The combined organic layers were washed with water, brine, dried over $Na_2SO_4$ and concentrated. The crude product was purified using flash silica gel column to give titled Compound 32 (0.199 g, 55%).

Step 2:

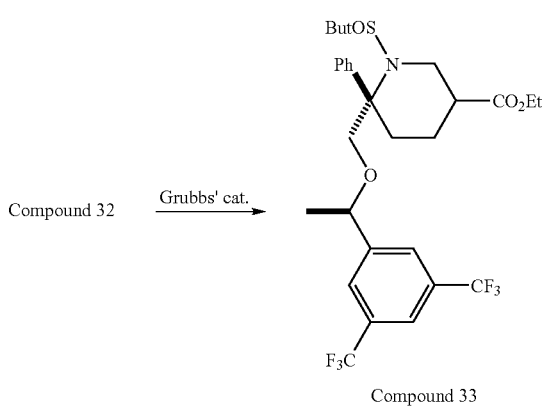

Compound 32 —Grubbs' cat.→ Compound 33

To a solution of Compound 32 (50 mg, 0.078 mmol, 1 equiv) in anhydrous CH₂Cl₂ (0.8 ml) under N₂ was added Grubbs' catalyst tricyclohexylphosphine [1,3-bis(2,4,6-trimethyl-phenyl)-4,5-dihydro-imidazol-2-ylidene][benzylidine]ruthenium(IV) dichloride (6.7 mg, 0.0079 mmol, 0.1 equiv). The resulting brown solution was heated at 40-45° C. for 2 h. The solvent was then removed and the residue was purified on a silica gel column to afford the titled Compound 33-(60 mg, 63%). Electrospray MS [M+1]$^+$ 502.1.

Step 3:

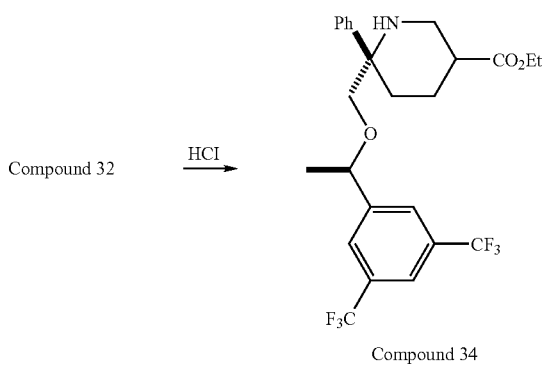

Compound 32 —HCl→ Compound 34

To a solution of Compound 33 (30 mg, 0.05 mmol, 1 equiv) in absolute MeOH (0.5 ml) at 0° C. was added a solution of 4N HCl in dioxane (0.5 ml). The resulting solution was stirred at 0° C. for 4 h. The solvent was then removed and the residue was dissolved in CH₂Cl₂ and passed through a short K₂CO₃ column. The residue of Compound 34 was taken directly to the next step without further purification.

Step 4:

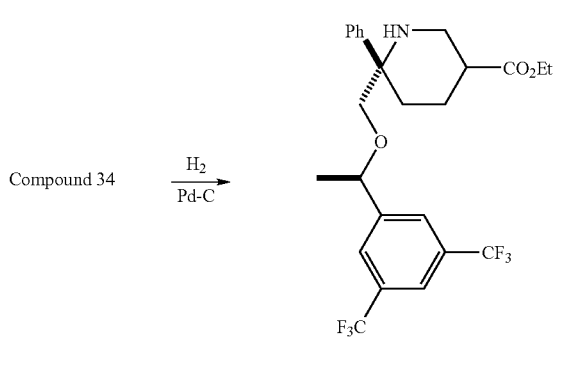

Compound 34 —H₂/Pd-C→ Compound 35

A solution of Compound 34 (30 mg, 0.06 mmol) in EtOH (5 ml) was treated with 10% Pd—C (32 mg, 0.03 mmol) and was hydrogenated at 60 psig for 18 h. The catalyst was filtered and washed with EtOAc. The filtrate was concentrated and the resulting residue of Compound 35 was taken directly to the next step without further purification.

Step 5:

To a mixture of methylamine HCl salt (52 mg, 0.77 mmol, 12.8 equiv) in toluene (0.2 ml) was added Me₃Al (2M in toluene, 0.36 ml, 0.72 mmol) and the resulting mixture stirred for 30 min. A solution of Compound 35 (30 mg, 0.06 mmol) in toluene (0.5 ml) was added to the reaction mixture via syringe. The resulting solution was heated at 100° C. for 18 h. The reaction mixture was then poured into saturated aq. Na/K tartarate solution (10 ml), stirred for 10 min and extracted with EtOAc (4×10 ml). The combined organic layers were-washed with brine and concentrated. The residue was subjected to prep TLC to afford the less polar isomer, Example 38a, Electrospray MS [M+1]$^+$ 489.1 and the more polar isomer, Example 38b, Electrospray MS [M+1]$^+$ 489.1.

Example 39

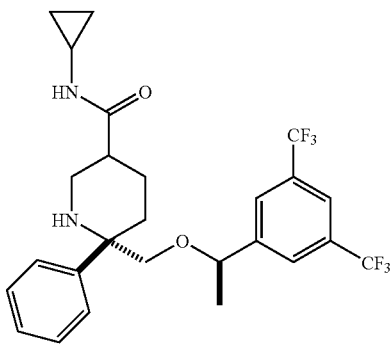

Step 1:

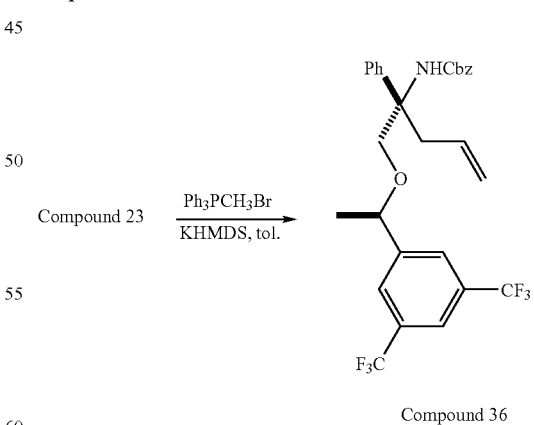

Compound 23 —Ph₃PCH₃Br / KHMDS, tol.→ Compound 36

Compound 36 (yield 63%) was prepared from Compound 23 using the procedure similar to the preparation of Compound 23 from Compound 3 and using methyltriphenyl-phosphonium bromide in place of (methoxymethyl)triphenylphosphonium chloride.

Step 2:

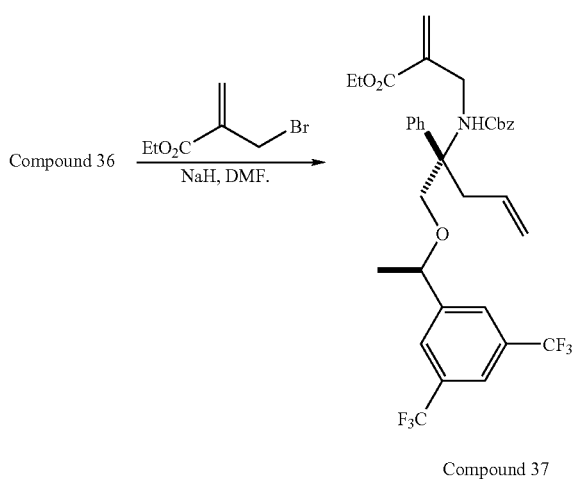

Compound 37

Compound 37 (50% yield) was prepared using similar procedure as for Compound 32 using Compound 36 in place-of Compound 17.

Step 3:

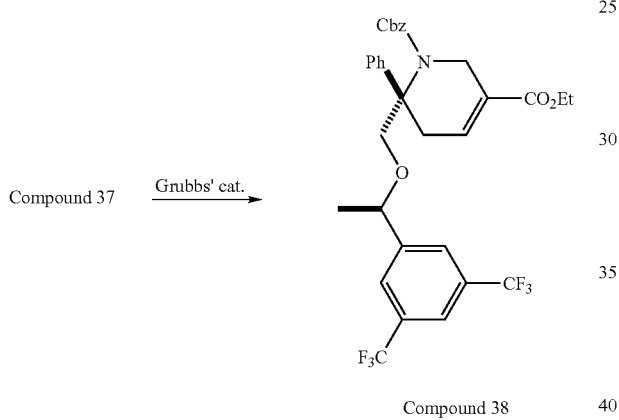

Compound 38

To a solution of Compound 37 (2.46 g, 3.71 mmol, 1 equiv) in anhydrous $CH_2Cl_2$ (50 ml) under $N_2$ was added Grubbs' catalyst (327 mg, 0.385 mmol, 0.1 equiv). The resulting brown solution was heated at 40-45° C. overnight. The solvent was then removed and the residue was purified on a silica gel column to afford Compound 38 (2.1 g, 89%).

Step 4:

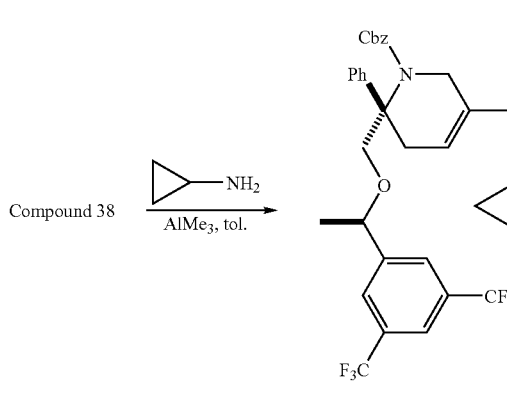

Compound 39

To a mixture of cyclopropylamine (0.24 ml, 3.45 mmol, 4.2 equiv) in toluene (1.0 ml) was added Me3Al (2M in toluene, 1.71 ml, 3.41 mmol, 4.2 equiv) and the resulting mixture stirred for 30 min. A solution of Compound 38 (516 mg, 0.82 mmol, 1 equiv) in toluene (2.5 ml) was added to the reaction mixture via syringe. The resulting solution was heated at 60° C. for 18 h. The reaction mixture was then poured into saturated aq. Na,K tartarate solution, stirred for 10 min and extracted with EtOAc (10 ml×4). The combined organic layers were washed with brine and concentrated. The residue was purified on silica column to afford Compound 39 (360 mg, 68%).

Step 5:

A solution of Compound 39 (360 mg, 0.556 mmol, 1 equiv) in EtOH (25 ml) was treated with 10% Pd—C (641 mg, 0.613 mmol, 1.1 equiv) and was hydrogenated at 50 psi for 6 h. The catalyst was filtered and washed with EtOAc. The residue was purified by silica gel column to afford the less polar isomer, Example 39a (54 mg, 19%) Electrospray MS $[M+1]^+$ 515.1, and the more polar isomer, Example 39b (22 mg, 8%) Electrospray MS $[M+1]^+$ 515.1

Example 40a and Example 40b

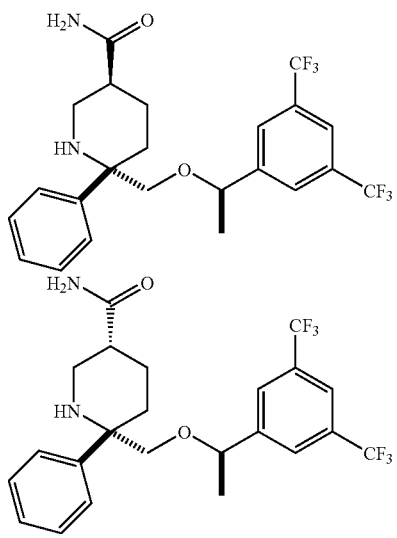

Step 1:

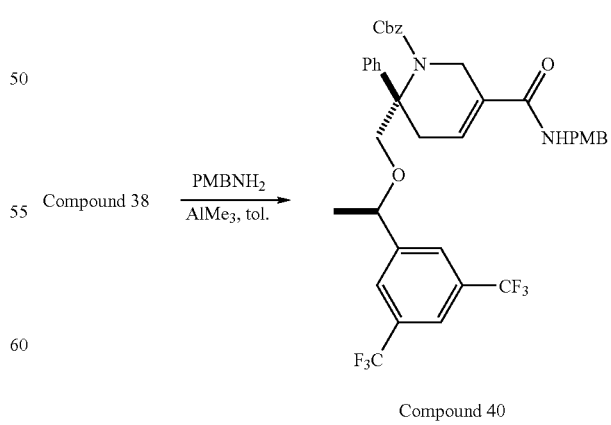

Compound 40

Compound 40 (yield 55%) was prepared using similar procedure as for Compound 39 using para-methoxylbenzylamine in place of cyclopropylamine.

Step 2:

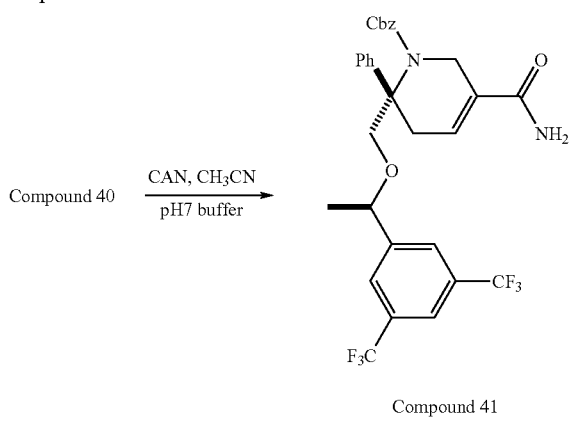

Compound 41

A solution of Compound 40 (1 g, 1.38 mmol, 1 equiv) in CH₃CN (10 ml) and pH7 buffer (3 ml) was treated with ammonium cerium(IV) nitrate (2.17 g, 3.96 mmol, 2.9 equiv) at RT for 2 h. Aqueous work-up gave the crude product which was purified by silica gel column to give Compound 41 (760 mg, 91%).

Step 3:

Example 40a and Example 40b were prepared using a similar procedure as for Example 39a and Example 39b using Compound 41 instead of Compound 39.

Electrospray MS [M+1]⁺ 475.1 for the Example 40a (less polar isomer);

Electrospray MS [M+1]⁺ 475.1 for the Example 40b (more polar isomer).

Example 41

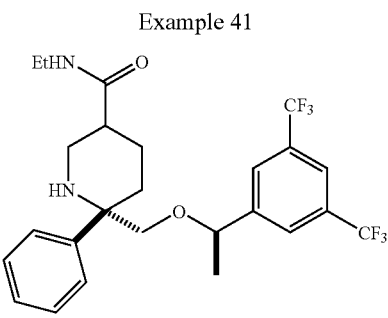

Example 41a and Example 41b were prepared using a similar procedure as for Example 38a and Example 38b using ethylamine instead of methylamine.

Electrospray MS [M+1]⁺ 503.1 for the Example 41a (less polar isomer);

Electrospray MS [M+1]⁺ 503.1 for the Example 41b (more polar isomer).

Example 42

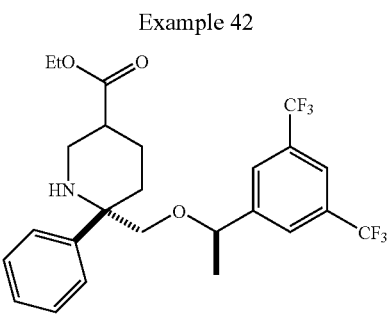

The mixture of two isomers of Compound 35 was separated by column chromatography to give pure Example 42a and Example 42b Electrospray MS [M+1]⁺ 504.1 for the Example 42a (less polar isomer);

Electrospray MS [M+1]⁺ 504.1 for the Example 42b (more polar isomer).

Example 43a Example 43b

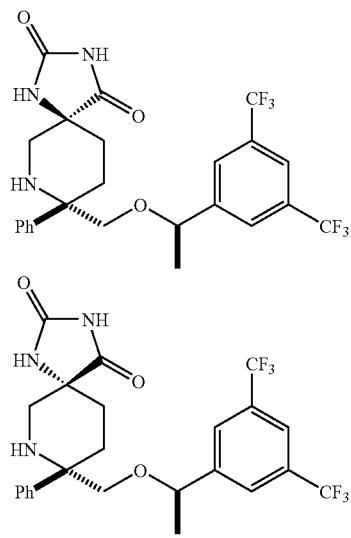

Step 1:

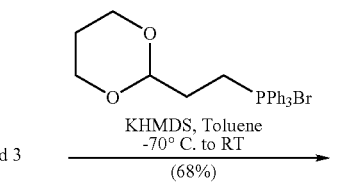

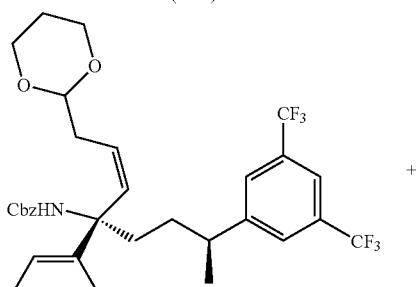

Compound 42

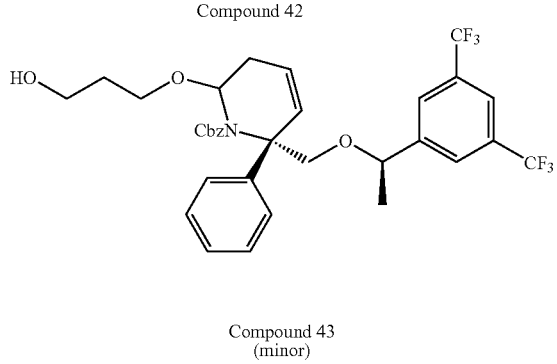

Compound 43
(minor)

To a suspension of lactol Compound 3 (60 g, 93.0 mmol, 1 equiv.) and Wittig Reagent (93.5 g, 200.0 mmol, 2.15 equiv.)

in toluene (800 ml) stirred at −78° C. under N₂, a solution of KHMDS (0.5M in toluene, 558 ml, 280.0 mmol, 3 equiv.) was added dropwise at −78° C. The cooling bath was removed and the yellow mixture was warmed to RT to form a red solution. The mixture was allowed to stir at 23° C. for further 1 h before being quenched with saturated NH₄Cl solution. EtOAc was added and layers were separated. The separated aqueous layer was extracted with EtOAc (2×500 ml). The combined organic layers were dried (MgSO₄) and filtered. Removal of solvents in vacuum followed by Biotage column chromatography [5% EtOAc-hexane to 10% EtOAc-hexane] gave alkene Compound 42 as white solid (40.5 g, 68%), Electrospray MS [M+1]⁺ 638.1. Continuous elution gave an impure cyclized product Compound 43.

Step 2:

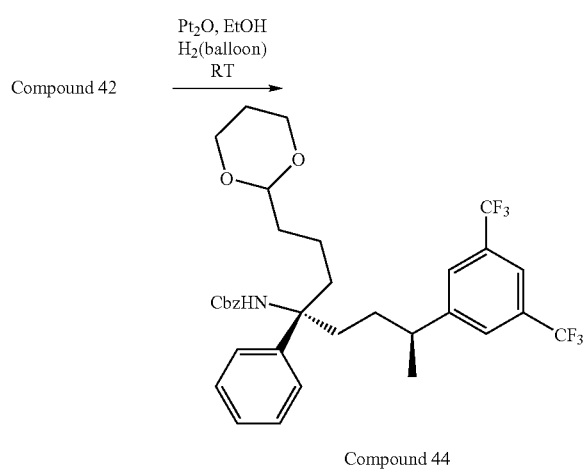

Compound 44

A suspension of alkene Compound 42 (40.5 g, 64 mmol, 1 equiv.) and PtO₂ (1.44 g, 6.4 mmol, 0.1 equiv.) in EtOH (400 ml) were stirred under a H₂ balloon at 23° C. for 24 h. Another batch of PtO₂ (1.44 g, 6.4 mmol, 0.1 equiv) was added and the mixture was stirred for another 24 h at 23° C. The catalyst was filtered via a pad of Celite. This solution of alkane Compound 44 was used in the next step without further purification.

Step 3:

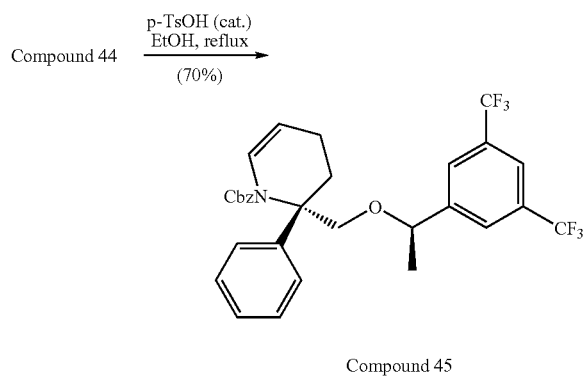

Compound 45 p-TsOH.H₂O (2.42 g, 13.0 mmol) was added to the ethanolic solution of alkane Compound 44 from above and the solution was heated to reflux for 4 h. The solution was cooled to RT and neutralized with Et₃N. Solvents were removed in vacuum and EtOAc was added. Saturated NaHCO₃ solution was added and layers were separated. The separated aqueous layer was extracted with EtOAc (300 ml×2). The combined organic layers were dried (MgSO₄) and filtered. Removal of solvents in vacuum followed by Biotage column chromatography [10% ether-hexane] gave enamide Compound 45 (first batch) as yellow oil. Some intermediate and starting material were recovered as yellow oil by continuous elution with [50% EtOAc-hexane]. The yellow oil was dissolved in toluene and 10 mol % p-TsOH was added. The mixture was heated to reflux for 2 h and cooled to RT. Work up was as above and the combined enamide Compound 45 (25 g, 70%), Electrospray MS [M+1]⁺ 564.1, was obtained as yellow oil.

Step 4:

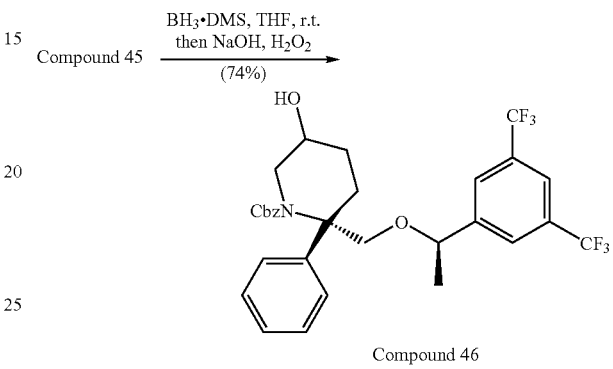

Compound 46

BH₃.Me₂S (13.6 ml, 133 mmo, 3.02 equiv) was added to a solution of enamide Compound 45 (25 g, 44.0 mmol, 1 equiv.) in THF at 23° C. under N₂. The mixture was stirred at 23° C. for 18 h and then cooled over an ice-water bath. A solution of NaOH (500 ml, 2N) was added slowly followed by a solution of H₂O₂ (500 ml, 30% aqueous). The mixture was allowed to stir from 0° C. to 23° C. for 18 h. Layers were separated and the separated aqueous layer was extracted with Et₂O (500 ml×2). The combined organic layers were dried (MgSO₄) and filtered. Removal of solvents in vacuum followed by Biotage column chromatography [hexane-EtOAc, 3:1 (v/v)] gave alcohol Compound 46 as colorless oil (19 g, 74%), Electrospray MS [M+1]⁺ 582.1.

Step 5:

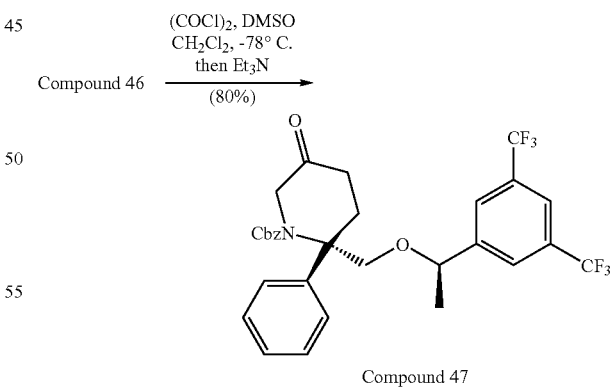

Compound 47

Oxalyl chloride (5.7 ml, 65.3 mmol, 2 equiv.) was added to a solution of DMSO (9.3 ml, 131.0 mmol, 4 equiv.) in CH₂Cl₂ (300 ml) at −78° C. under N₂. The mixture was stirred at −78° C. for 15 min before a solution of alcohol Compound 46 (19 g, 32.7 mmol. 1 equiv.) in CH₂Cl₂ (50 ml) was added. The mixture was stirred at −78° C. for a further 1 h and Et₃N (32 ml, 228.9 mmol, 7 equiv.) was added. The cooling bath was removed and the mixture was warmed to RT before it was quenched with saturated NaHCO₃ solution. Layers were separated and the aqueous was extracted with CH₂Cl₂ (300 ml×2). The combined organic layers were dried (MgSO₄) and filtered. Removal of solvents in vacuum followed by Biotage column chromatography [hexane-ether, 4:1 (v/v)] gave ketone Compound 47 as colorless oil (15 g, 80%), Electrospray MS [M+1]⁺ 580.1.

Step 6:

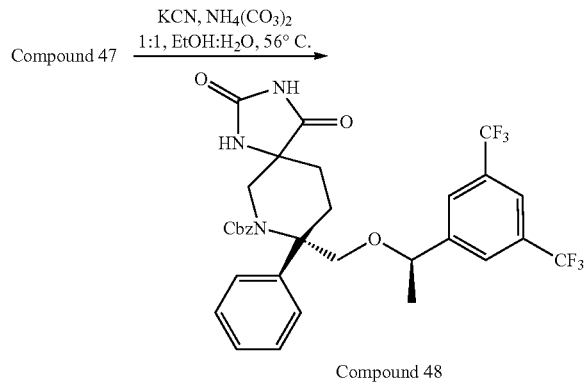

Compound 48

EtOH (150 ml) was added to Cbz-ketone Compound 47 (15 g, 25.88 mmol, 1 equiv.), followed by NH₄(CO₃)₂ (9.95 g, 103.5 mmol, 4 equiv.) and a solution of KCN (3.4 g, 51.77 mmol, 2 equiv.). The resulting mixture was heated at 58° C. under N₂ for 72 h. TLC (1:1 EtOAc:hexane) revealed complete consumption of the starting material. The reaction mixture was cooled to RT and poured into sat. aq. NaHCO₃ (200 ml) and extracted with EtOAc (3×200 ml). The combined organic layers were dried over MgSO₄ and concentrated in vacuo to afford crude Cbz-hydantoin Compound 48 (16.5 g, 98%), Electrospray MS [M+1]⁺650.1. The crude material was used in the next reaction without further purification.

Step 7:

The crude Cbz-hydantoin Compound 48 (16.5 g, 25.4 mmol, 1 equiv.) was dissolved in MeOH (220 ml) and 20% Pd(OH)₂—C (3.6 g) was added. The reaction mixture was shaken in a parr shaker under H₂ atmosphere at 40 psi for 18 h. TLC (1:1 EtOAc:hexane) revealed complete consumption of the starting material. The reaction mixture was filtered through a pad of celite and the celite was washed with MeOH. The resulting solution was concentrated in vacuo. The crude product was purified by column chromatography on a Biotage (3:2, EtOAc:hex). Two major spots were collected. The less-polar spot corresponds to the isomer Example 43a (3 g, overall 20% over two steps), Electrospray MS [M+1]⁺ 516.1. The more polar spot corresponds to the isomer Example 43b (4.5 g, overall 30% over two steps), Electrospray MS [M+1]⁺ 516.1.

Examples 44a and 44b

Example 44a

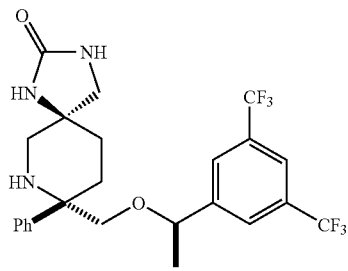

Example 44b

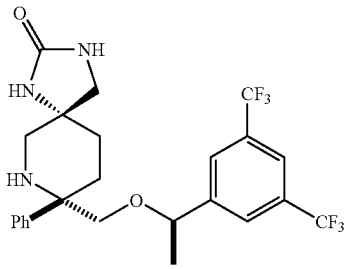

A flame-dried 25 ml RBF was charged with AlCl₃ (0.01 g, 0.776 mmol, 4 equiv). The reaction flask was cooled to 0° C. and 1 M solution of LAH in Et₂O (0.58 ml, 0.58 mmol, 3 equiv) was added. The mixture was stirred at 0° C. for 10 min and then a solution of Example 43b (0.1 g, 0.194 mmol, 1 equiv.) in dry THF (3 ml) was slowly added via cannula. The reaction mixture was stirred at 0° C. for 1 h and then allowed to warm up to RT stirred for 18 h. The reaction was then cooled to 0° C. and quenched carefully with saturated aqueous sodium potassium tartarate solution. It was then stirred at 0° C. for over 30 min. The mixture was extracted with EtOAc (2×200 ml). The combined organic layer was dried over Na₂SO₄, filtered and concentrated. The crude product was purified by column chromatography on a Biotage (1:9, MeOH:EtOAc) to afford Example 44b (0.066 g, 68%), Electrospray MS [M+1]⁺ 502.1.

Example 44a was prepared from Example 43a using the procedure described for the preparation of Example 44b from Example 43b.

Electrospray MS [M+1]⁺ 502.1 for the Example 44a.

Example 45

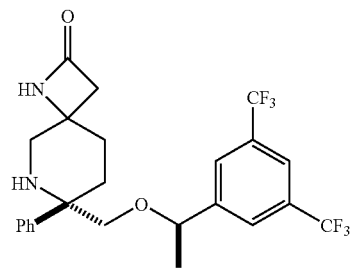

Step 1:

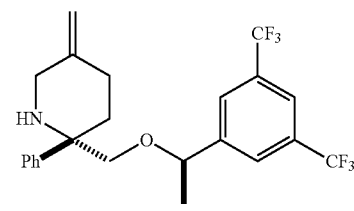

Compound 49

To a suspension of (methyl)triphenylphosphonium bromide (0.37 g, 1.04 mmol, 3 equiv) in toluene (5 ml) at 0° C.

under N₂, a solution of KHMDS (1.73 ml, 0.863 mmol, 2.5 equiv) was added. After being stirred at 0° C. for 1 h, a solution of Compound 47 (0.2 g, 0.35 mmol, 1 equiv) in toluene (7 ml) was added. The mixture was stirred at 0° C. for 1.5 h and then quenched with saturated NaHCO₃ (150 ml). The mixture was extracted with EtOAc (100 ml×3). The combined organic layers were dried (MgSO₄), filtered and concentrated. The crude product was purified by column chromatography on a Biotage (4:1, hexane:EtOAc) to afford Compound 49 (0.196 g, 98%).

Step 2:

To a solution of Compound 49 (0.196 g, 0.34 mmol, 1 equiv) in dry Et₂O (3 ml) at 0° C. was added chlorosulfonylisocyanate (0.045 ml, 0.51 mmol, 1.5 equiv). The reaction mixture was stirred at 0° C. for 1 h and then warmed to 23° C. Another equivalent of chlorosulfonylisocyanate was added and the mixture was stirred 23° C. for 18 h. The reaction mixture was diluted with Et₂O (12 ml), 10% aqueous Na₂SO₃ solution was added and pH of the reaction mixture was adjusted to 8 using 2M aqueous KOH solution. The mixture was stirred for 1.5 h and then washed with brine. The organic layer was dried (MgSO₄), filtered and concentrated. The crude product was purified by column chromatography on a Biotage (2:1, hexane:EtOAc) to afford the crude NCbz-lactam product (20 mg) which was converted to mixture of desired products Example 45a and 45b using a procedure similar to the preparation of Example 43a and Example 43b from Compound 48. The mixture of two products was separated on prep. plate (6:95, MeOH;EtOAc) to afford the less polar isomer, Example 45a (0.006 g, 3.5% over four steps), Electrospray MS [M+1]⁺ 487.1 and the more polar isomer, Example 45b (0.003 g, 1.79% over four steps), Electrospray MS [M+1]⁺ 487.1.

Examples 46

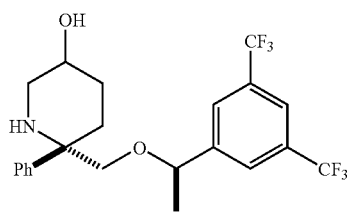

Example 46a and Example 46b were prepared from Compound 46 using a procedure similar to the preparation of Example 43a and Example 43b from Compound 48.

Electrospray MS [M+1]⁺ 448.1 for the Example 46a (less polar isomer);

Electrospray MS [M+1]⁺ 448.1 for the Example 46b (more polar isomer).

Example 47

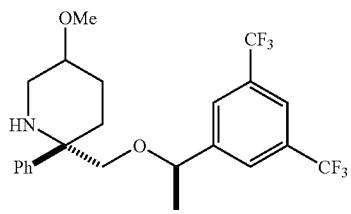

To a solution of NCbz-alcohol Compound 46 (0.125 g, 0.215 mmol, 1 equiv) in dry DMF (3 ml) at 0° C. was added NaH (60% in mineral oil, 0.017 g, 0.43 mmol, 2 equiv). The reaction mixture was stirred at 0° C. for 20 min and then CH₃I (0.04 ml, 0.645 mmol, 3 equiv) added and the mixture was stirred at 23° C. for 18 h. The crude was poured into CH₂Cl₂ (100 ml) and washed with brine (100 ml×2). The organic layer was dried (MgSO₄), filtered and concentrated. The crude product was purified by column chromatography over Biotage (4:1, hexane:EtOAc) to afford the crude NCbz-methylether product (69 mg) which was hydrogenated to the mixture of desired products Example 47a and 47b using a procedure similar to the preparation of Example 43a and Example 43b from Compound 48. The mixture of two products was purified by column chromatography over Biotage (1:4, hexane:EtOAc) to afford the less polar isomer, Example 47a, Electrospray MS [M+1]⁺ 462.1 and the more polar isomer, Example 47b, Electrospray MS [M+1]⁺ 462.1.

Example 48

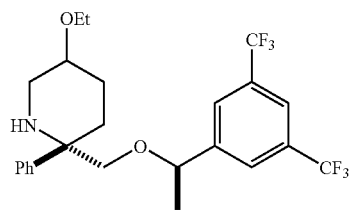

Example 48a and Example 48b were prepared from Compound 46 using the procedure similar to the preparation of Example 47a and Example 47b and using ethyl iodide in place of methyl iodide.

Electrospray MS [M+1]⁺ 476.1 for the Example 48a (less polar isomer);

Electrospray MS [M+1]⁺ 476.1 for the Example 48b (more polar isomer)

Example 49

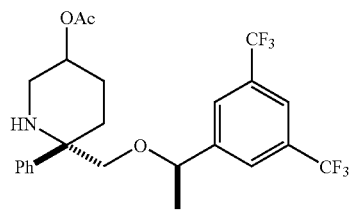

To a solution of NCbz-alcohol Compound 46 (0.118 g, 0.20 mmol, 1 equiv) in dry CH₂Cl₂ (3 ml) at 0° C. was added dry pyridine (0.026 ml, 0.325 mmol, 1.6 equiv), followed by acetyl chloride (0.023 ml, 0.325 mmol, 1.6 equiv). The reaction mixture was warmed to 23° C. for and stirred for 18 h. The mixture was then concentrated and purified by column chromatography on a Biotage (4:1, hexane:EtOAc) to afford the crude NCbz-acetate product (108 mg) which was hydrogenated to the crude desired product using a procedure similar to the preparation of Example 23a and Example 23b from Compound 48. The crude product was purified by column chromatography on a Biotage (5:95 MeOH:EtOAc) to afford Example 49 (0.079 g, 79% over two steps), Electrospray MS [M+1]⁺ 490.1.

Examples 50a and 50b

Example 50a

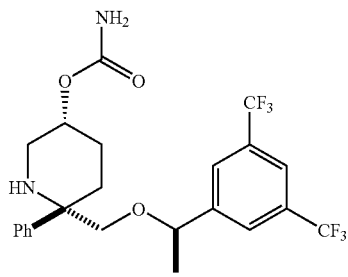

Example 50b

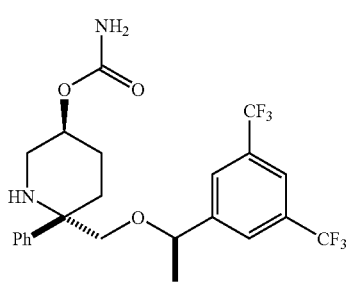

To a solution of NCbz-alcohol Compound 46 (0.223 g, 0.385 mmol, 1 equiv) in CH$_2$Cl$_2$ (8 ml) at 0° C. was added trichloroacetyl isocyanate (0.055 ml, 0.46 mmol, 1.2 equiv). The reaction mixture was stirred at 0° C. for 15 min and then concentrated in vacuo. The residue was dissolved in CH$_3$OH (7 ml) and water (5 ml) was added. The mixture was cooled to 0° C. and K$_2$CO$_3$ (0.16 g, 1.16 mmol, 3 equiv) was added. The reaction mixture was stirred at 0° C. for 1 h and then warmed to 23° C. and stirred for 18 h. The reaction mixture was then concentrated in vacuo and water (100 ml) was added to the residue and the mixture was extracted with CH$_2$Cl$_2$ (1 00 ml×2). The combined organic layers were dried (Na$_2$SO$_4$), filtered and concentrated to afford the crude NCbz-carbamate product (232 mg) which was hydrogenated to the mixture of desired products Example 50a and 50b using a procedure similar to the preparation of Example 43a and Example 43b from Compound 48. The mixture of two products was purified by column chromatography over Biotage (1:4, hexane:EtOAc) to afford pure Example 50a and pure Example 50b.

Electrospray MS [M+1]$^+$ 491.1 for the Example 50a (less polar isomer);
Electrospray MS [M+1]$^+$ 491.1 for the Example 50b (more polar isomer)

Example 51

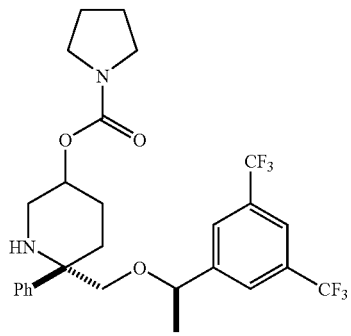

A mixture of NCbz-alcohol Compound 46 (0.2 g, 0.344 mmol, 1 equiv.), 1,4-dioxane (3 ml), 1-pyrrolidine carbonyl chloride (0.076 ml, 0.69 mmol, 2 equiv.) and dry pyridine (0.084 ml, 1.03 mmol, 3 equiv.) was heated in a sealed tube at 100° C. for 18 h. The reaction mixture was cooled to 23° C. and diluted with EtOAc (150 ml). The mixture was washed with water (1 00 ml) and the organic layer was dried (Na$_2$SO$_4$), filtered and concentrated to afford the crude NCbz-carbamate product (232 mg) which was hydrogenated to the mixture of desired products Example 51a and 51b using a procedure similar to the preparation of Example 43a and Example 43b from Compound 48. The mixture of two products was purified by column chromatography over Biotage (2:3, hexane:EtOAc) to afford the less polar isomer, Example 51a and the more polar isomer, Example 51b.

Electrospray MS [M+1]$^+$ 545.1 for the Example 51a;
Electrospray MS [M+1]$^+$ 545.1 for the Example 51b.

Example 52

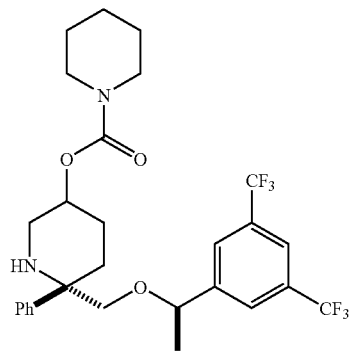

Example 52a and Example 52b were prepared from Compound 46 using the procedure similar to that used for the preparation of Example 51a and Example 51b and using 1-piperidine carbonyl chloride in place of 1-pyrrolidine carbonyl chloride.

Electrospray MS [M+1]$^+$ 559.1 for the Example 52a (less polar isomer);
Electrospray MS [M+1]$^+$ 559.1 for the Example 52b (more polar isomer).

Example 53

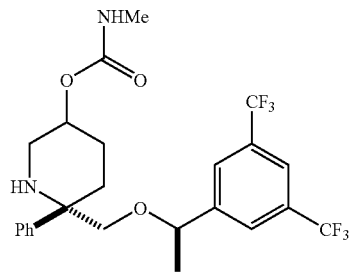

Example 53a and Example 53b were prepared from Compound 46 using the procedure similar to that used for the preparation of Example 51a and Example 51 b and using methylisocyanate in place of 1-pyrrolidine carbonyl chloride.

Electrospray MS [M+1]+ 505.1 for the Example 53a (less polar isomer);
Electrospray MS [M+1]+ 505.1 for the Example 53b (more polar isomer).

Example 54

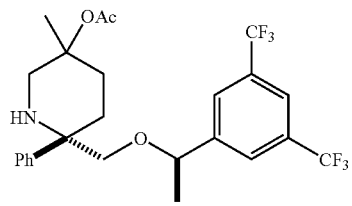

Compound 47 →
1. CeCl₃•7H₂O
2. MeMgL

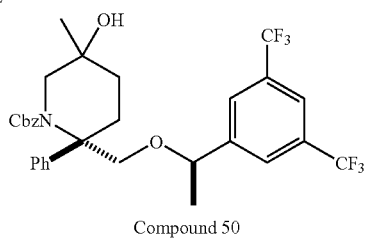

Compound 50

CeCl₃ (0.186 g, 0.5 mmol, 2.1 equiv) was added to a 25 ml RBF and heated in vacuo at 140° C. for two h. The flask was cooled to 23° C. under N₂, dry THF (2 ml) was added and the resulting suspension was stirred at 23° C. for 18 h. The mixture was then cooled to 140° C. and CH₃MgI (0.159 ml, 0.476 mmol, 2 equiv.) was added and stirred at 0° C. for 1 h. A solution of Compound 47 (0.138 g, 0.238 mmol, 1 equiv) in dry THF (2.5 ml) was added dropwise and the reaction mixture was stirred under N₂ at 0° C. for 0.5 h. The mixture was quenched with saturated aq. NH₄Cl solution (50 ml) and extracted with EtOAc (100 ml×2). The combined organic layers were dried (MgSO₄), filtered and concentrated. The mixture was purified by column chromatography over Biotage (4:1, hexane:Et₂O) to afford the NCbz-alcohol Compound 50 (0.115 g, 80%).

The NCbz-alcohol Compound 50 was converted to the desired product Example 54 (63% yield over two steps) using a procedure similar to the preparation of Example 49 from Compound 46.

Electrospray MS [M+1]+ 504.1 for the Example 54.

Example 55

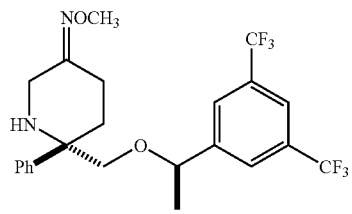

To a solution of Compound 47 (0.1 g, 0.173 mmol, 1 equiv) in dry pyridine (1 ml) was added methoxylamine hydrochloride (0.058 g, 0.69 mmol, 4 equiv) and the reaction mixture was stirred 23° C. for 18 h. The mixture was quenched with water (50 ml) and extracted with CH₂Cl₂ (100 ml×2). The combined organic layers were dried (Na₂SO₄), filtered and concentrated to give NCbz-oxime (0.102 g, 97%) which was hydrogenated to afford the crude product Example 55 using a procedure similar to the preparation of Example 43a and Example 43b from Compound 48, except that the reaction was carried out in a H₂ balloon atmosphere at RT instead of a parr shaker at 40 psi. The crude product was purified by column chromatography over Biotage (4:1, EtOAc:hexane) to afford Example 55 (0.063 g, 79%), Electrospray MS [M+1]+ 475.1.

Examples 56a and 56b

Example 56a

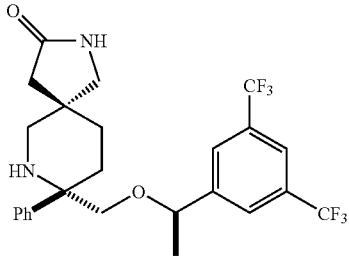

Example 56b

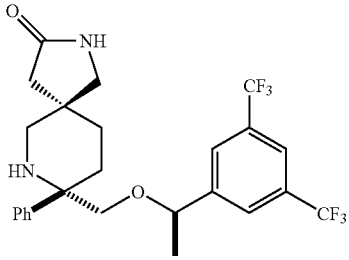

Step 1:

Compound 47 →
(EtO)₂P(O)CH₂CO₂Me
NaH, THF
(98%)

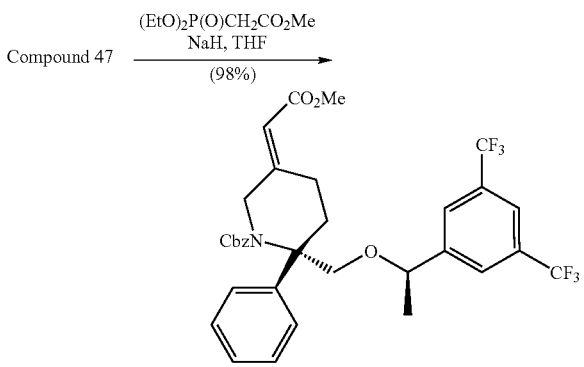

Compound 51

To a suspension of NaH (1.8 g, 44.5 mmol, 60% in oil) in THF (200 ml) at 0° C. under N₂, methyl diethylphosphonoacetate (8.2 ml, 44.5 mmol) was added. The mixture was stirred at 0° C. for 15 min and a solution of ketone Compound 47 (8.6 g, 14.8 mol) in THF (50 ml) was added. The mixture was allowed to warm to RT and stirred for 1 h before it was quenched with saturated NH₄Cl solution. Water and EtOAc were added to the mixture. Layers were separated and the aqueous layer was extracted with EtOAc (200 ml×2). The combined organic layers were dried (MgSO₄) and filtered. Solvents were removed in vacuum and purification by column chromatography [hexane-EtOAc, 4:1 (v/v)] gave unsaturated ester Compound 51 (9.2 g, 98%) as colorless oil. Electrospray MS [M+1]⁺=636.1.

Step 2:

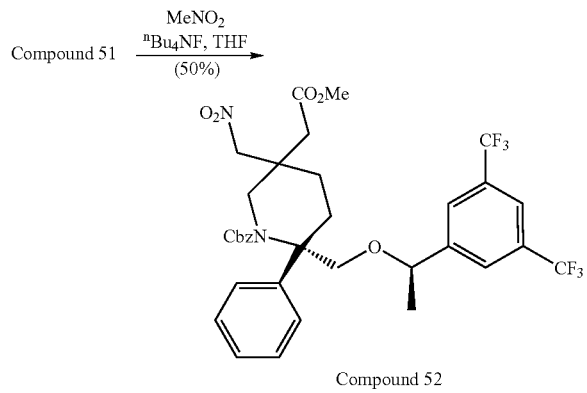

Compound 52

A mixture of unsaturated ester Compound 51 (9.2 g, 14.5 mmol) and tetrabutylammonium fluoride (145 ml, 1.0 M in THF) in $CH_3NO_2$ were heated to reflux for 2 h. The mixture was cooled to RT and quenched with saturated $NH_4Cl$ solution. Water and EtOAc were added to the mixture. Layers were separated and the aqueous layer was extracted with EtOAc (X2). The combined organic layers were dried ($MgSO_4$) and filtered. Solvents were removed in vacuum and purification by column chromatography [hexane-acetone, 9:1 (v/v)] gave the less polar alkene (4.1 g, 45%) as colorless oil. Continuous elution with the same solvent system gave the more polar nitroester Compound 52 (5.1 g, 50%) as colorless oil. Electrospray MS [M+1]⁺=670.1.

Step 3:

A mixture of Compound 52 (5.1 g, 7.32 mmol), a catalytic amount of $Pd(OH)_2$ (20% on carbon) and a catalytic amount of Raney Ni (50% slurry in water) were shaken in a Parr hydrogenator at 50 psi overnight. The mixture was filtered through a pad of Celite and solvents were removed in vacuum to give a mixture of Example 56a and 56b as colorless oil (3.5 g, 95%). Separation by HPLC using Chiralcel OD [hexane-isopropanol, 9:1 (v/v)] gave less polar isomer Example 56a as white foam. Electrospray MS [M+1]⁺=501.1. Continuous elution with the same solvent system gave the more polar isomer Example 56b as colorless oil. Electrospray MS [M+1]⁺=501.1.

Example 57

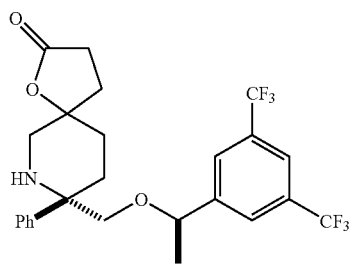

To a solution of ethyl propiolate (0.27 ml, 2.69 mmol) in THF (10 ml) at −78° C. under $N_2$, t-butyllithium (1.6 ml, 2.69 mmol, 1.7M in pentane) was added. The mixture was stirred at −78° C. for 10 min and a solution of Compound 47 (519 mg, 0.90 mmol) in THF (5 ml) was added. The mixture was stirred at −78° C. for 1 h, then quenched with HOAc at −78° C. Water and EtOAc were added to the mixture. Layers were separated and the aqueous layer was extracted with EtOAc (200 ml×2). The combined organic layers were dried ($MgSO_4$) and filtered. Solvents were removed in vacuum and purification by column chromatography [hexane-EtOAc, 4:1 (v/v)] gave a colorless oil. The oil was dissolved in EtOH and a catalytic amount of palladium (10% on carbon) was added. The mixture was shaken in a Parr hydrogenator at 45 psi overnight. The mixture was filtered through a pad of Celite and solvents were removed in vacuum to give a colorless oil. The oil was dissolved in toluene and catalytic amount of p-TsOH was added. The mixture was heat to reflux overnight. After being cooled to RT, the mixture was quenched with saturated $NaHCO_3$ solution. Water and EtOAc were added to the mixture. Layers were separated and the aqueous layer was extracted with EtOAc (250 ml×2). The combined organic layers were dried ($MgSO_4$) and filtered. Solvents were removed in vacuum to give a mixture of Example 57a and 57b as colorless oil. Separation by column chromatography [hexane-ether, 1:2(v/v)] gave the less polar minor isomer Example 57a (67 mg, 15%) as white foam. Electrospray MS [M+1]⁺=502.1. Continuous elution with the same solvent system gave the more polar major isomer Example 57b (134 mg, 30%) as white solid. Electrospray MS [M+1]⁺=502.1.

Example 58

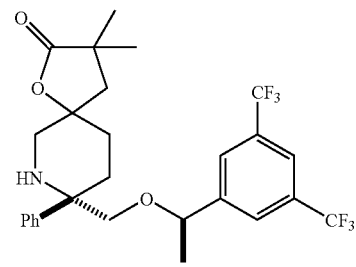

To a solution of Example 57a (1 12 mg, 0.22 mmol) in THF (5 ml) at −78° C. under $N_2$, lithium bis(trimethylsilyl)amide (1.1 ml, 1.12 mmol, 1.0 M in THF) was added. The mixture was stirred at −78° C. for 1 h and $CH_3I$ (70 µl, 1.12 mmol) was added. The mixture was stirred at −78° C. for 1 h before quenched with saturated $NH_4Cl$ solution. Water and EtOAc were added to the mixture. Layers were separated and the aqueous layer was extracted with EtOAc (100 ml×2). The combined organic layers were dried ($MgSO_4$) and filtered. Solvents were removed in vacuum and purification by column chromatography [hexane-ether, 3:1 (v/v)] gave Example 58 (92 mg, 78%) as colorless oil. Electrospray MS [M+1]⁺=530.1.

Example 59

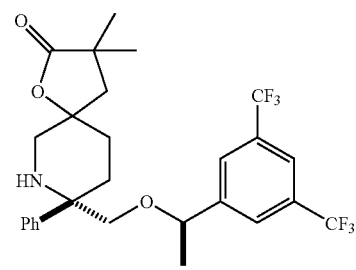

Example 59 (75%) was prepared from Example 57b in a manner similar to that used to prepare Example 58 from Example 57a. Electrospray MS [M+1]$^+$=530.1.

Examples 60a and 60b

Example 60a

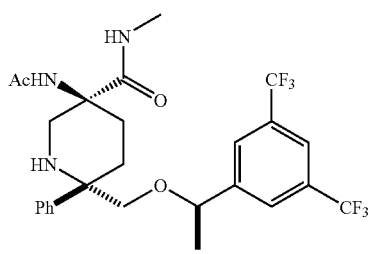

Example 60b

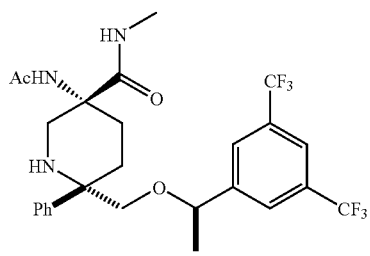

Step 1:

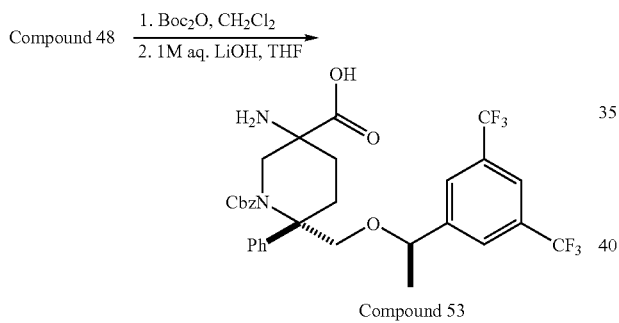

Compound 53

To a solution of Compound 48 (0.5 g, 0.77 mmol, 1 equiv) in CH$_2$Cl$_2$ (30 ml) was added di tert-butyl dicarbonate (0.37 g, 1.69 mmol, 2.2 equiv) followed by DMAP (0.035 g, 0.286 mmol, 0.37 equiv) and the reaction mixture was stirred at 23° C. for 18 h. The reaction mixture was then filtered through a short pad of silica using (1:1 hexane:EtOAc) and concentrated in vacuo to afford diBoc-hydantoin (0.59 g, 90%). The diBoc-hydantoin (0.59 g, 0.7 mmol, 1 equiv) was dissolved in THF (30 ml) and 1 M aq. LiOH solution (5.56 ml, 5.56 mmol, 8 equiv) was added. The reaction mixture was stirred at 23° C. for 18 h. Saturated aq. NaHCO$_3$ was added to the reaction mixture and extracted with EtOAc (100 ml×3). The combined organic layers were dried (Na$_2$SO$_4$), filtered and concentrated to give crude Compound 53 (0.52 g) which was used in the next reaction without further purification.

Step 2:

To a mixture of crude Compound 53 (0.52 g) in pyridine (3 ml) and THF (2 ml) at 0° C. was added acetyl chloride (0.072 ml, 1 mmol, 1.2 equiv) and the reaction mixture was warmed to 23° C. and stirred for 18 h. The reaction mixture was then concentrated and purified by column chromatography over Biotage (5:95, MeOH:EtOAc) to afford a yellow oil of N-acetylated product (0.31 g, 0.456 mmol, 1 equiv.) which was dissolved in THF (10 ml). A 2M solution of CH$_3$NH$_2$ in THF (2.3 ml, 4.6 mmol, 10 equiv) was added and the reaction mixture was stirred at 23° C. for 18 h. The mixture was diluted with EtOAc (100 ml) and washed with saturated aq. NaHCO$_3$ (100 ml). The organic layer was were dried (Na$_2$SO$_4$), filtered and concentrated to give crude NCbz-amide which was hydrogenated to afford the mixture of two isomers Example 60a and 60b using a procedure similar to the preparation of Example 43a and Example 43b from Compound 48. The mixture of two products was separated on HPLC "ChiralPak AD column" using (1:9, IPA:hexane) to afford the more polar isomer pure Example 60a, Electrospray MS [M+1]$^+$=546.1 and less polar isomer pure Example 60b, Electrospray MS [M+1]$^+$=546.1.

Example 61

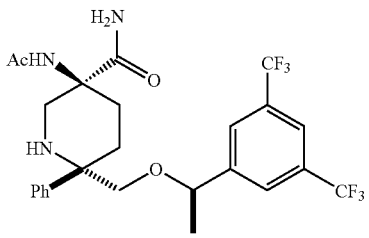

Example 61 was prepared from Example 43a using the procedure similar to the preparation of Examples 60a and 60b from Compound 48, but using a solution of ammonia (0.5M in 1,4-dioxane) in place of CH$_3$NH$_2$ solution (2M in THF). Electrospray MS [M+1]$^+$=532.1.

Example 62

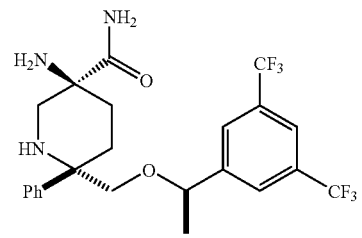

Step, 1:

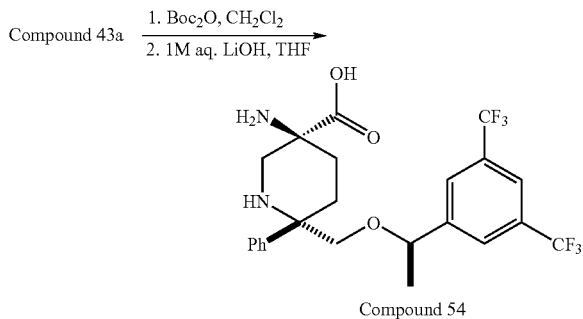

Compound 54

Compound 54 was prepared from Example 43a using the procedure similar to the preparation of Compound 53 from Compound 48. Compound 54 was used in the next reaction without further purification.

Step 2:

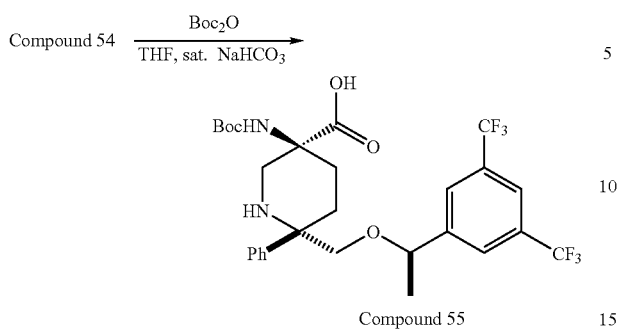

To a mixture of Compound 54 (0.5 g, 1.02 mmol, 1 equiv) in THF (30 ml) was added sat. aq. NaHCO₃ followed by di tert-butyl dicarbonate (0.58 g, 2.65 mmol, 2.6 equiv). The reaction mixture was stirred at 23° C. for 18 h. The mixture was cooled to 0° C. and 10% aq. citric acid (20 ml) was added and the resulting mixture was extracted with EtOAc (100 ml×3). The combined organic layers were dried (Na₂SO₄), filtered and concentrated to give crude Compound 55 (0.93 g) which was used in the next reaction without further purification.

Step 3:

To a solution of Compound 55 (0.93 g, 1.57 mmol, 1 equiv) in CH₂Cl₂ (15 ml) was added DIEA (0.83 ml, 4.72 mmol, 3 equiv) followed by PyBOP (1.23 g, 2.4 mmol, 1.3 equiv). After 15 min, 0.5M solution of ammonia in 1,4-dioxane (31.5 ml, 15.75 mmol, 10 equiv) was added to the reaction mixture and stirred at for 23° C. for 18 h. The reaction mixture was quenched with water (100 ml) and extracted with EtOAc (100 ml×3). The combined organic layers were dried (Na₂SO₄), filtered and concentrated. The crude product was purified by column chromatography over Biotage (1:10:89, Et₃N: MeOH:EtOAc) to afford NBoc-amide which was dissolved in CH₂Cl₂ (10 ml) and cooled to 0° C. TFA (6 ml) was added and the reaction mixture was warmed to 23° C. and stirred for 2 h. The reaction was quenched carefully with sat. aq. NaHCO₃ (100 ml) and diluted with CH₂Cl₂ (100 ml). The organic layer was separated, dried (Na₂SO₄), filtered and concentrated. The crude product was purified by column chromatography over Biotage (10:90, MeOH:EtOAc) to afford the desired product Example 62 (0.18 g, 35% over three steps), Electrospray MS [M+1]⁺=490.1.

Example 63

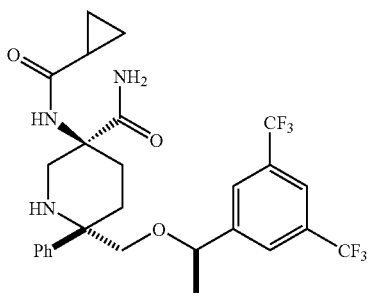

Example 63 was prepared from Example 62 using the procedure similar to the preparation of Example 14 from Example 13 and using cyclopropyl acid chloride in place of propionyl chloride and also using DIEA (1.3 equiv).

Electrospray MS [M+1]⁺=558.1.

Example 64

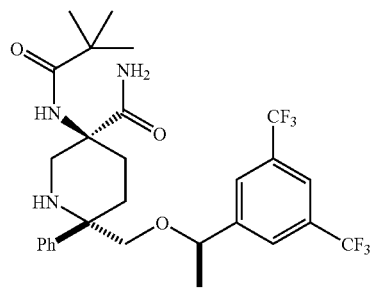

Example 64 was prepared from Example 62 using the procedure similar to the preparation of Example 14 from Example 13 and using t-butyl chloride in place of propionyl chloride.

Electrospray MS [M+1]⁺=574.1.

Example 65

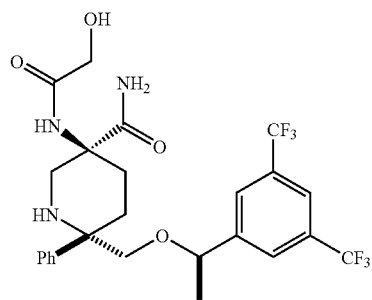

Step 1:

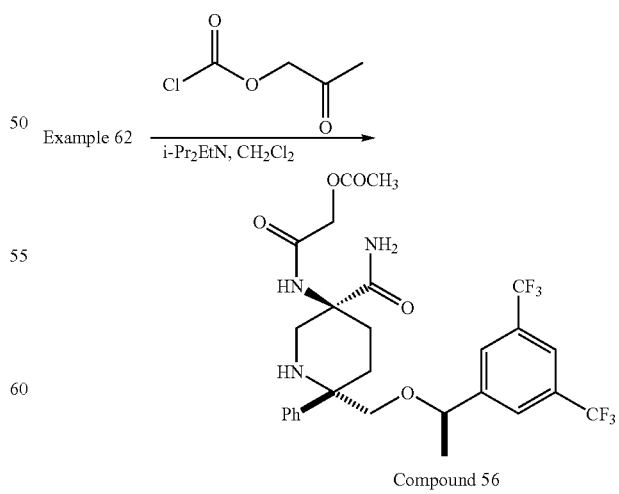

Compound 56 was prepared from Example 62 using the procedure similar to the preparation of Example 14 from Example 13 but using acetoxyacetyl chloride in place of propionyl chloride. The crude Compound 56 was used in the next reaction without further purification.

Step 2:

The crude Compound 56 was dissolved in MeOH (5 ml), KHCO$_3$ (3 equiv) was added and the reaction mixture was stirred at 23° C. for 18 h. The reaction mixture was concentrated and purified by column chromatography over Biotage (10:90, MeOH:EtOAc) to afford the desired product Example 65, Electrospray MS [M+1]$^+$=548.1.

Example 66

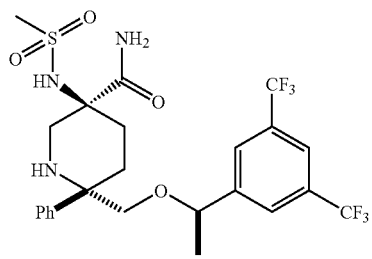

Example 66 was prepared from Example 62 using the procedure similar to the preparation of Example 14 from Example 13 and using CH$_3$SO$_2$Cl in place of propionyl chloride.

Electrospray MS [M+1]$^+$=568.1 for the Example 66.

Example 67

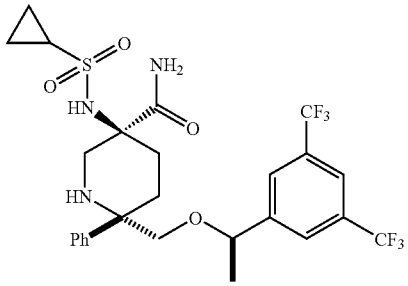

Example 67 was prepared from Example 62 using the procedure similar to the preparation of Example 14 from Example 13 but using cyclopropylsulfonyl chloride in place of propionyl chloride. Electrospray MS [M+1]$^+$=594.1.

Example 68

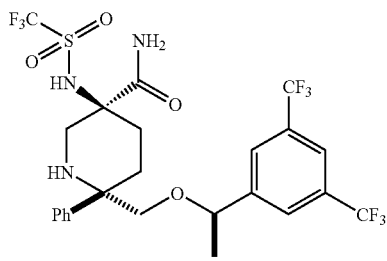

Example 68 was prepared from Example 62 using the procedure similar to the preparation of Example 14 from Example 13 but using trifluoromethanesulfonic anhydride in place of propionyl chloride.

Electrospray MS [M+1]$^+$=622.1 for the Example 68.

Example 69

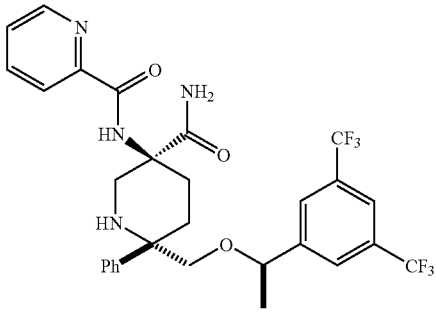

Example 69 was prepared from Example 62 using the procedure similar to the preparation of Example 14 from Example 13 and using nicotinoyl chloride in place of propionyl chloride.

Electrospray MS [M+1]$^+$=595.1 for the Example 69.

Examples 70a and 70b

Example 70a

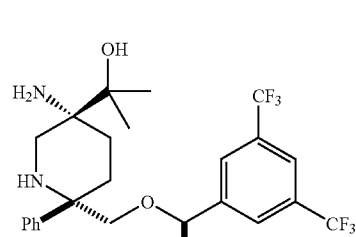

Example 70b

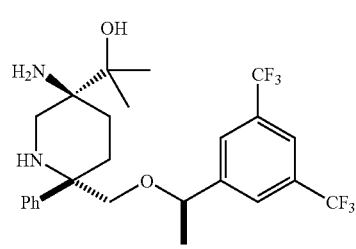

Step 1:

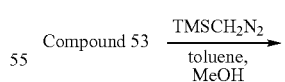

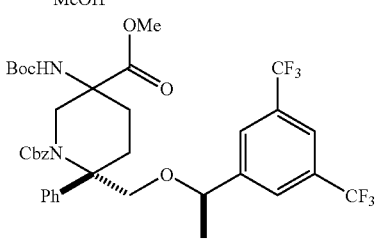

Compound 57

To a mixture of Compound 53 (4 g, 5.52 mmol, 1 equiv), toluene (46 ml) and MeOH (18 ml) at 0° C. was added TMSCH$_2$N$_2$ (2M solution in hexane, 13.8 ml, 27.6 mmol, 5 equiv) and the resulting solution was stirred at 0° C. for 30 min. The reaction mixture was then concentrated and purified by column chromatography over Biotage (2:1, hexane:EtOAc) to give Compound 57 (1.8 g, 44%).

Step 2:

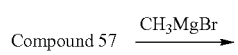

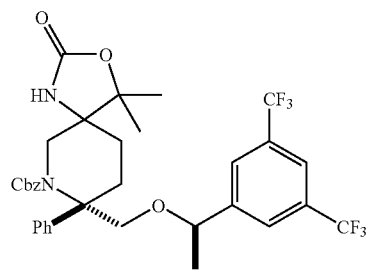

Compound 58

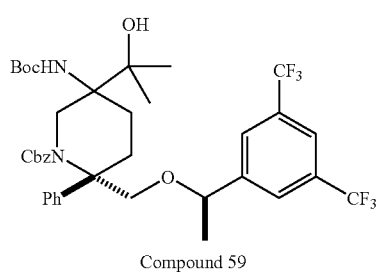

Compound 59

To a mixture of Compound 57 (1 g, 1.35 mmol, 1 equiv) in dry THF (18 ml) at 0° C. was added CH$_3$MgBr (1 M solution in n-butylether, 3.24 ml, 3.24 mmol, 2.4 equiv.) and the resulting solution was stirred at 0° C. for 30 min. The reaction mixture was then warmed to 23° C. and stirred for 18 h. The reaction was quenched with saturated aq. NaHCO$_3$ (100 ml) and extracted with EtOAc (200 ml). The organic layer was separated, dried (Na$_2$SO$_4$), filtered and concentrated. The mixture was purified by column chromatography over Biotage (2:1, hexane:EtOAc) to give more polar Compound 58 (0.52 g, 56%) and less polar Compound 59 (0.31 g, 34%).

Step 3:

Compound 59 was deprotected with TFA using the procedure described in the preparation of Example 62. The resulting NCbz-aminoalcohol compound was hydrogenated to afford the mixture of two isomers Example 70a and 70b using a procedure similar to the preparation of Examples 43a and 43b from Compound 48. The mixture of two products was separated on HPLC "ChiralCel OD column" using (1:9, IPA:hexane) to afford-less polar isomer Example 70a, Electrospray MS [M+1]$^+$ 505.1, and more polar isomer Example 70b, Electrospray MS [M+1]$^+$ 505.1.

Example 71

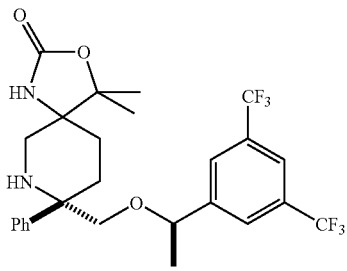

Compound 58 was hydrogenated to a mixture of desired products Example 71a and 71b using a procedure similar to the preparation of Examples 43a and 43b from Compound 48. The mixture of two products was purified by column chromatography over Biotage (1:1, hexane:EtOAc) to afford pure less polar isomer Example 71a, Electrospray MS [M+1]$^+$ 531.1 and pure more polar isomer Example 71b, Electrospray MS [M+1]$^+$ 531.1.

Examples 72a and 72b

Example 72a

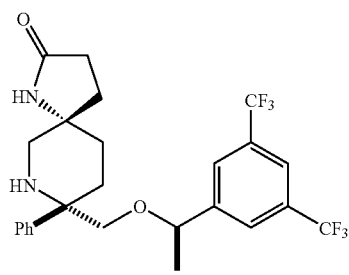

Example 72b

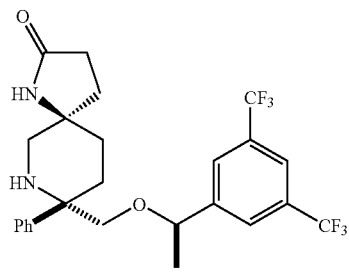

Step 1:

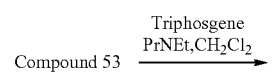

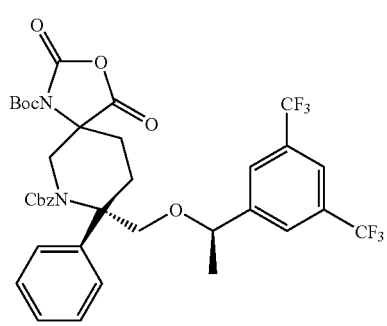

Compound 60

To a solution of crude Compound 53 (19 g) in CH₂Cl₂ (300 ml) at RT, DIEA (15 ml, 0.087 mol)was added, followed by triphosgene (4.34 g, 0.015 mol). The mixture was stirred at RT for 18 h and was filtered through a pad of silica. Solvents were removed in vacuum to give crude Compound 60 as yellow oil which was used in the next reaction without further purifications.

Step 2:

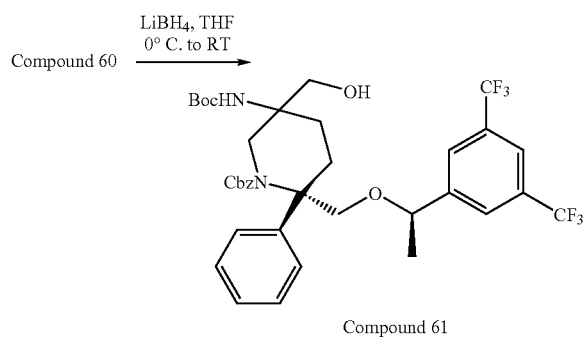

Compound 61

To the crude Compound 60 in THF (200 ml) at 0° C., LiBH₄ (1.26 g, 0.058 mol) was added in small portions. The mixture was stirred at RT for 18 h before quenching with saturated NH₄Cl solution. Water and EtOAc were added to the mixture. Layers were separated and the aqueous layer was extracted with EtOAc (100×2). The combined organic layers were dried (MgSO₄) and filtered. Solvents were removed in vacuum and purification by column chromatography [hexane-EtOAc, 4:1 (v/v)] gave Compound 61 (12.9 g, 62% overall) as white foam.

Step 3:

Oxalyl chloride (4.2 ml, 0.048 mol) was added to a solution of DMSO (6.8 ml, 0.096) in CH₂Cl₂ (300 ml) at −78° C. under N₂. The mixture was stirred at −78° C. for 15 min before a solution of Compound 61 (8.5 g, 0.012 mol) in CH₂Cl₂ (100 ml) was added. The mixture was stirred at −78° C. for a further 1 h and Et₃N (23.5 ml) was added. The cooling bath was removed and the mixture was warmed to RT before it was quenched with saturated NaHCO₃ solution. Layers were separated and the aqueous was extracted with CH₂Cl₂ (150 ml×2). The combined organic layers were dried (MgSO₄) and filtered. Removal of solvents in vacuum gave an aldehyde as yellow oil. To a mixture of NaH (1.44 g, 0.036 mol) in THF at 0° C., methyl diethylphosphonoacetate (6.6 ml, 0.036 mol) was added. The mixture was stirred at 0° C. for 15 min and a solution of aldehyde in THF (100 ml) was added. The cooling bath was removed and the mixture was stirred at RT for 1 h. The reaction was quenched with saturated NH₄Cl solution. Water and EtOAc were added to the mixture. Layers were separated and the aqueous layer was extracted with EtOAc (200 ml×2). The combined organic layers were dried (MgSO₄) and filtered. Solvents were removed in vacuum and purification by column chromatography [hexane-EtOAc, 4:1 (v/v)] gave an ester as white foam. The ester was dissolved in EtOH (100 ml) and a catalytic amount of palladium (1.28 g, 10% on carbon) was added. The mixture was shaken under H₂ (50 psi) for 2 days. Catalytic amount of Pd(OH)₂ (20% on carbon) was then added to the mixture and the mixture was again shaken under H₂ (50 psi) for 5 h. The mixture was filtered through a pad of Celite and solvents were removed in vacuum to give a white foam. The foam was then dissolved in CH₂Cl₂ (200 ml) and TFA (8.9 ml, 0.12 mol) was added. The mixture was stirred at RT for 18 h and was cooled at 0° C. before it was neutralized with saturated NaHCO₃ solution. Water and EtOAc were added to the mixture. Layers were separated and the aqueous layer was extracted with EtOAc (200 ml×2). The combined organic layers were dried (MgSO₄) and filtered. Solvents were removed in vacuum to give a yellow oil. The oil was dissolved in CH₃OH (50 ml) and a catalytic amount of K₂CO₃ (166 mg, 0.0012 mol) was added. The mixture was heated at 60° C. for 2 h. After being cooled to RT, the mixture was filtered through a pad of silica and solvents were removed in vacuum. Purification by column chromatography (EtOAc) gave the mixture of two isomers Example 72a and 72b (2.3 g, 38% overall) as white foam. Separation by HPLC using Chiralcel OD [hexane-isopropanol, 95:5 (v/v)] gave the less polar major isomer Example 72a as white foam. Electrospray MS [M+1]⁺=501.1. Continuous elution with the same solvent system gave the more polar minor isomer Example 72b as colorless oil.

Electrospray MS [M+1]⁺=501.1.

Examples 73a and 73b

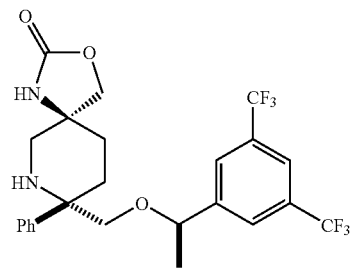

Example 73a

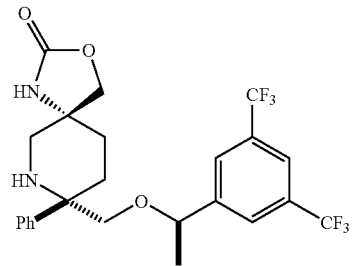

Example 73b

To a solution of Compound 61 (3 g, 4.22 mmol, 1 equiv) in DMF (60 ml) at 0° C. was added NaH (60% in mineral oil, 0.122 g, 5.07 mmol, 1.2 equiv) and the mixture was allowed to warm to 23° C. and stirred for 45 min. The reaction was quenched with water (100 ml) and extracted with EtOAc (100 ml×3). The combined organic layers were dried (MgSO₄), filtered and concentrated. The crude product purified by column chromatography over Biotage (2:1, hexane:EtOAc).to afford the desired product which was hydrogenated to afford the mixture of two isomers Example 73a and 73b using a procedure similar to the preparation of Examples 43a and 43b from Compound 48. The mixture of two products was separated on HPLC "ChiralPak AD column" using (5:95, IPA:hexane) to afford pure less polar isomer Example 73a and more polar isomer Example 73b.

Electrospray MS [M+1]⁺=503.1 for Example 73a.

Electrospray MS [M+1]⁺=503.1 for Example 73b.

Example 74

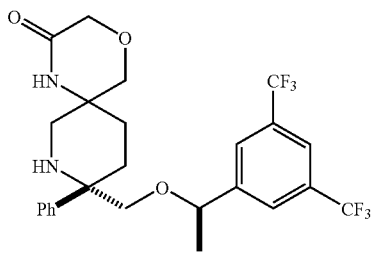

Compound 61 (1.68 g, 2.36 mmol, 1 equiv) was dissolved in CH$_2$Cl$_2$ (50 ml), TFA (5.46 ml, 70.9 mmol, 30 equiv) was added and the reaction mixture was stirred at 23° C. for 2.5 h. The reaction was quenched carefully with sat. aq. NaHCO$_3$ (150 ml) and diluted with CH$_2$Cl$_2$ (100 ml). The organic layer was separated, dried (Na$_2$SO$_4$), filtered and concentrated to give crude amino-alcohol product (1.4 g, 97%). The product (0.32 g, 0.524 mmol, 1 equiv) was dissolved in dry THF (10 ml) and NaH (60% in mineral oil, 0.025 g, 0.63 mmol, 1.2 equiv.) was added. The reaction mixture was stirred at 23° C. for 5 min and then ethyl chloroacetate (0.062 ml, 0.576 mmol, 1.1 equiv) was added and the reaction mixture was stirred for 2.5 h. The reaction was quenched carefully with sat. aq. NaHCO$_3$ (100 ml) and diluted with EtOAc (200 ml). The organic layer was separated, dried (Na$_2$SO$_4$), filtered and concentrated. The crude product was purified by column chromatography over Biotage (2:3, hexane:EtOAc) to give the product (0.1 g, 32%) which was hydrogenated to afford the mixture of two isomers Example 74a and 74b using a procedure similar to the preparation of Examples 43a and 43b from Compound 48. The mixture of two products was separated on HPLC "ChiralCel OD column" using (1:9, IPA:hexane) to afford pure Example 74a, Electrospray MS [M+1]$^+$ 517.1, and pure Example 74b, Electrospray MS [M+1]$^+$ 517.1.

Example 75

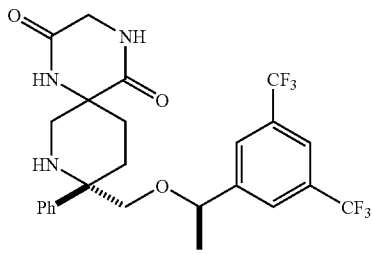

Step 1:

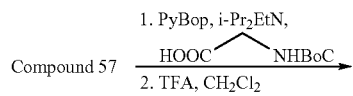

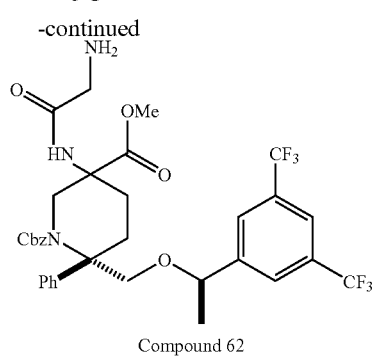

Compound 62

Compound 57 was converted to Compound 62 (72% yield over two steps) using the PyBOP coupling followed by TFA deprotection procedures as described in the preparation of Example 62 from Compound 55 but using Compound 57 (1 equiv.) in place of ammonia and NH-Boc-glycine (2 equiv.) in place of Compound 55.

Step 2:

Compound 62 (0.5 g, 0.72 mmol, 1 equiv) was dissolved in MeOH (10 ml) and Et$_3$N (1 ml, 7.2 mmol, 10 equiv) was added. The resulting mixture was heated at 23° C. for 18 h. The reaction mixture was then concentrated and purified by column chromatography over Biotage (EtOAc) to give NCbz-diketopiperazine (0.33 g) which was hydrogenated to afford the mixture of two isomers Example 75a and 75b using a procedure similar to the preparation of Examples 43a and 43b from Compound 48. The mixture of two products was separated on HPLC "ChiralPak AD column" using (5:95, IPA:hexane) to afford pure less polar isomer Example 75a (0.03 g, 8% over two steps), Electrospray MS [M+1]$^+$ 530.1, and more polar isomer Example 75b, (0.04 g, 11% over two steps), Electrospray MS [M+1]$^+$ 530.1.

Examples 76a and 76b

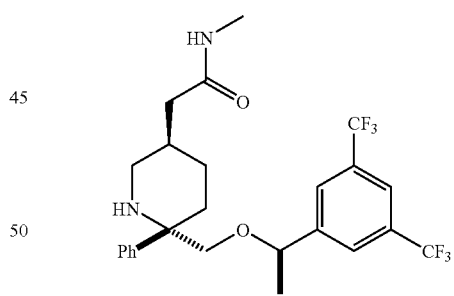

Example 76a

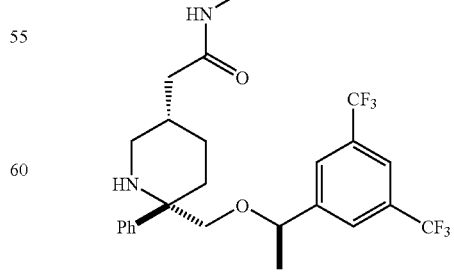

Example 76b

Compound 51 (3.66 g, 5.76 mmol, 1 equiv.) was hydrogenated using a procedure similar to the preparation of Examples 43a and 43b from Compound 48 and the hydrogenated product (2.85 g) was treated with CH₃NH₂ (2M solution in CH₃OH, 200 ml) and stirred at 23° C. for 18 h. The reaction mixture was then concentrated and purified by column chromatography over Biotage (1:9, MeOH:EtOAc) to give the mixture of two isomers Example 76a and 76b. The mixture of two isomers was separated on HPLC "ChiralPak AD column" using (5:95, IPA:hexane) to afford less polar isomer Example 76b, Electrospray MS [M+1]⁺ 503.1, and more polar isomer Example 76a, Electrospray MS [M+1]⁺ 503.1.

Example 77

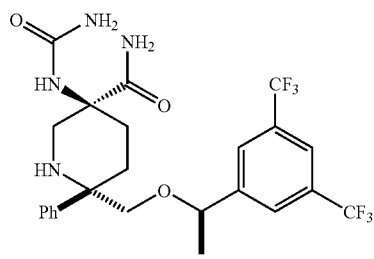

Example 62 (0.07 g, 0.133 mmol, 1 equiv) was dissolved in CH₂Cl₂ (3 ml) and DIEA (0.03 ml, 0.147 mmol, 1.1 equiv) was added followed by 4-methoxyphenyl (pmb)-isocyanate (0.021 ml, 0.147 mmol, 1.1 equiv) and the reaction mixture was stirred at 23° C. for 18 h. The reaction mixture was then concentrated and treated with CH₃CN (3 ml) and water (1 ml) and the mixture was cooled to 0° C. Ammonium cerium nitrate (0.24 g, 0.44 mmol, 4 equiv) was added and the reaction mixture was stirred at 0° C. for 45 min. The reaction was quenched with saturated aq. NaHCO₃ (100 ml) and extracted with EtOAc (200 ml). The organic layer was separated, dried (Na₂SO₄), filtered and concentrated. The mixture was purified by column chromatography over Biotage (15:85, MeOH:EtOAc) to give Example 77 (0.03 g, 42%), Electrospray MS [M+1]⁺ 533.1.

Examples 78a and 76b

Example 78a

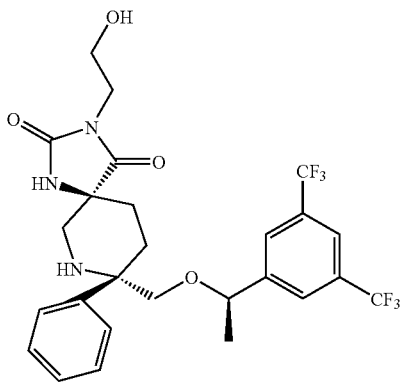

Example 78b

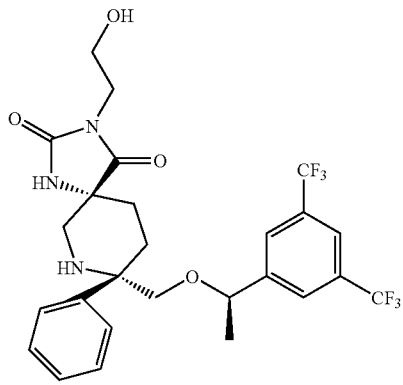

Step 1:

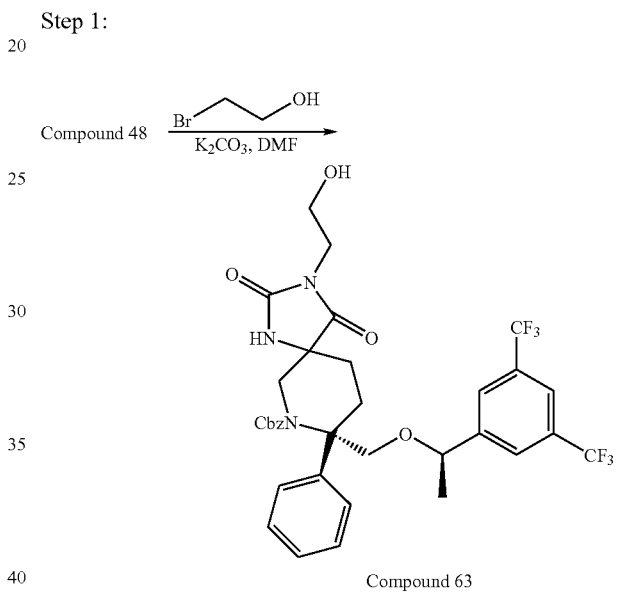

Compound 63

In a flame dry 15 ml RBF Compound 48 (0.25 g, 0.385 mmol, 1 equiv) in DMF (1 ml) was added to K₂CO₃ (0.106 g, 0.77 mmol, 2 equiv) followed by 2-bromoethanol (0.033 ml, 0.46 mmol, 1.2 equiv) and the mixture was stirred for 2 h at RT, then heated to 50° C. for 6 h. The reaction was monitored by TLC (60/40 EtOAc/Hexane). The reaction mixture was cooled to 0° C., quenched with H₂O, diluted with EtOAc and washed with brine. The organic layer was combined and dried over Na₂SO₄, filtered and concentrated. The reaction mixture was purified using Biotage using 2:3 EtOAc/Hexane to 3:2 EtOAc/Hexane to elute Compound 63 as a mixture of two isomers (0.258 g, 97%), Electrospray MS [M+1]⁺ 694.1.

Step 2:

To a solution of Compound 63 (0.25 g, 0.36 mmol, 1 equiv) in anhydrous MeOH was added (5.5 ml) 20% Pd(OH)₂/C (0.08 g). The reaction mixture was purged with N₂ followed by H₂ and stirred for 18 h under H₂. The reaction was monitored by TLC (60/40 EtOAc/Hexane). The catalyst was filtered through a plug of celite and the solution was concentrated to give crude product. The material was subjected to flash chromatography using a Biotage (80:20 EtOAc/Hexane). The isomers were separated to give Example 78a and Example 78b (0.13 g, 63%).

Electrospray MS [M+1]⁺ 560.1 for Example 78a (less polar isomer);

Electrospray MS [M+1]⁺ 560.1 for Example 78b (more polar isomer).

Examples 79a and 79b

Example 79a

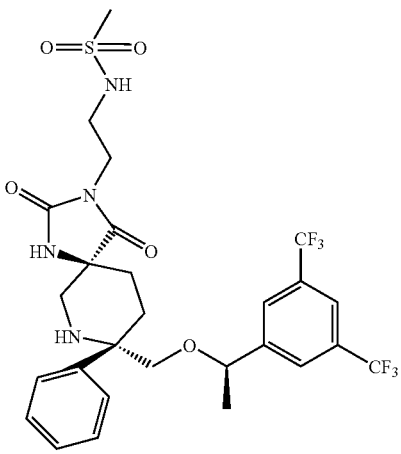

Example 79b

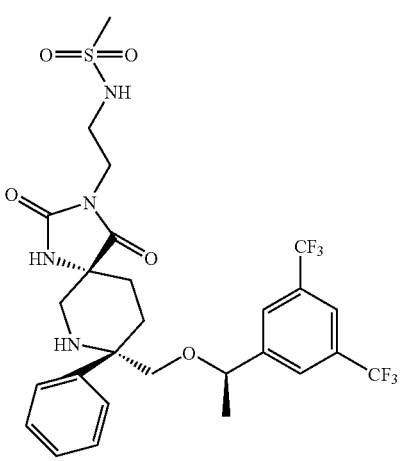

Step 1:

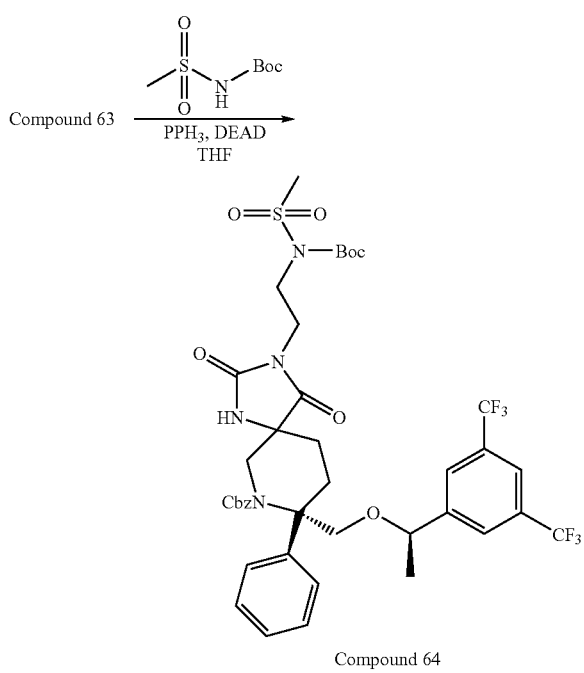

N-(Boc)-methanesulfonamide (0.041 g, 0.43 mmol, 1.5 equiv) was dissolved in dry THF (1 ml) and triphenyl phosphine (0.228 g, 0.43 mmol, 3 equiv) was added. The resulting solution was stirred under $N_2$ and a solution of Compound 63 (0.2 g, 0.29 mmol, 1 equiv) in THF followed by diethyl azodicarboxylate (DEAD) (0.12 ml, 0.26 mmol, 2.5 equiv) were added. The reaction monitored by TLC (60/40 EtOAc/Hexane). Upon completion, the reaction mixture was concentrated to give a yellow oil which was subjected to flash chromatography using a Biotage (1:1 EtOAc/Hexane) to elute the product, Compound 64, as a mixture of two isomers (0.24 g, 95%), Electrospray MS $[M+1]^+$ 871.1.

Step: 2

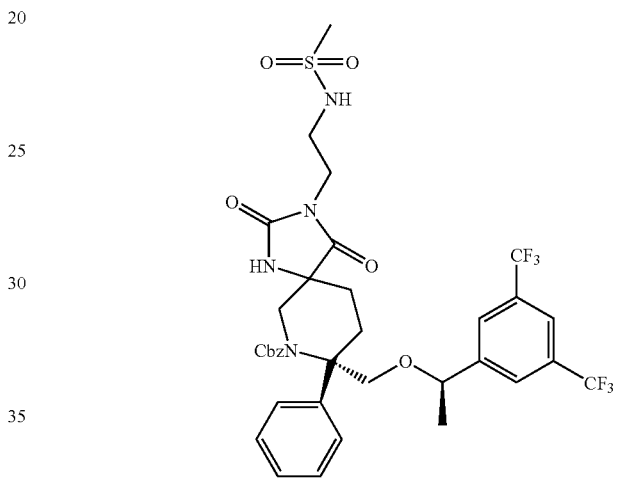

Compound 65

To a solution of Compound 64 (0.25 g, 0.29 mmol, 1 equiv) in dry $CH_2Cl_2$ (10 ml) at 0° C. was added 4M HCl in dioxane (0.755 ml, 2.9 mmol, 10 equiv). The reaction was warmed to RT and monitored by TLC (60/40 EtOAc/Hexane). Upon completion the reaction was quenched with water, diluted with $CH_2Cl_2$, washed with saturated $NaHCO_3$, and dried over $Na_2SO_4$ to give crude Compound 65 as a mixture of two isomers (0.2 g, 89%). The crude material was carried forward without any purification.

Electrospray MS $[M+1]^+$ 771.1 for Compound 65.

Step: 3

To a solution of Compound 65 (0.2 g, 0.26 mmol, 1 equiv) in MeOH (5 ml) was added 10% Pd/C followed by ammonium formate (0.082 g, 1.3 mmol, 5 equiv). The reaction was refluxed under $N_2$ for 3 h, then cooled to RT, filtered through celite, and concentrated. The residue was dissolved in EtOAc, washed with $NaHCO_3$ and dried over $Na_2SO_4$. The crude material was subjected to prep plate chromatography. Both of the isomers were isolated to give pure Example 79a and Example 79b (0.06 g, 36% total for both isomers).

Electrospray MS $[M+1]^+$ 637.1 for Example 79a (less polar isomer);

Electrospray MS $[M+1]^+$ 637.1 for Example 79b (more polar isomer).

Example 80

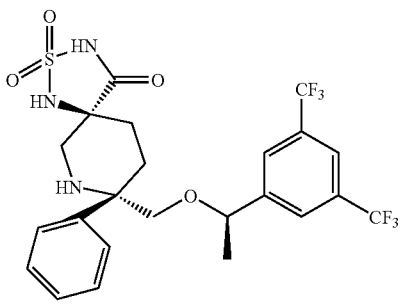

To a solution of Example 62 (0.079 g, 0.127 mmol, 1 equiv) in dry CH$_2$Cl$_2$ (1 ml) was added Et$_3$N (0.108 ml, 0.76 mmol, 6 equiv). The reaction mixture was cooled to 0° C. and stirred for 15 min. SO$_2$Cl$_2$ (0.011 ml, 0.133 mmol, 1.05 equiv) was added very slowly to the reaction over 5 min. The reaction stirred for 10 h and was monitored by TLC (9:1 EtOAc/CH$_3$OH). The reaction mixture was diluted with EtOAc, washed with NaHCO$_3$, and dried over Na$_2$SO$_4$. The crude product was subjected to prep plate chromatography to isolate Example 80 (0.015 g, 20%), Electrospray MS [M+1]$^+$ 552.1.

Example 81

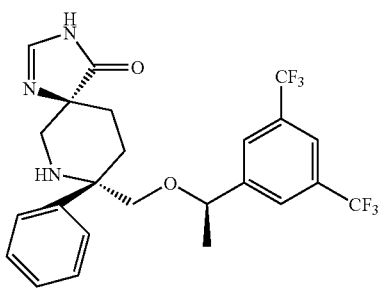

Step 1:

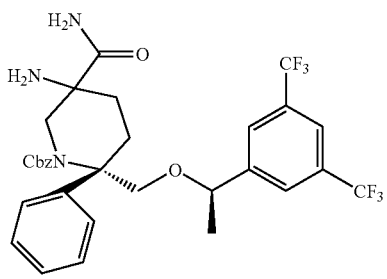

Compound 66a and 66b

Compounds 66a and 66b were prepared from Compound 48 using a procedure similar to the preparation of Example 62 from Example 43a.

Step 2:

Compound 66a $\xrightarrow[\text{Toluene}]{\text{Triethyl orthoformate, Acetic Acid}}$ Reflux

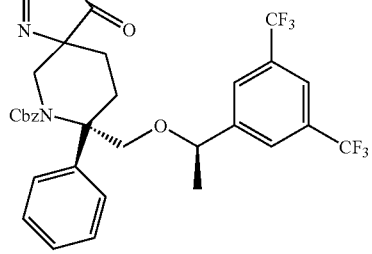

Compound 67a

To a solution of Compound 66a (0.34 g, 0.545 mmol, 1 equiv) in dry toluene (14 ml) was added HOAc (0.17 ml) followed by triethyl orthoformate (0.363 ml, 2.18 mmol, 4 equiv). The solution was refluxed for 12 h and monitored by TLC (9:1 EtOAc/CH$_3$OH). The reaction was cooled to 0° C., quenched with H$_2$O, diluted with EtOAc, washed with NaHCO$_3$, and dried over Na$_2$SO$_4$. The crude was subjected to flash chromatography using a Biotage (60:40 EtOAc/Hexane) to elute Compound 67a (0.272 g, 79%), Electrospray MS [M+1]$^+$ 634.1.

Step3:
Example 81 was prepared from Compound 67a using a similar procedure as for Examples 79a and 79b from Compound 65.

Electrospray MS [M+1]$^+$ 500.1 for Example 81.

Example 82

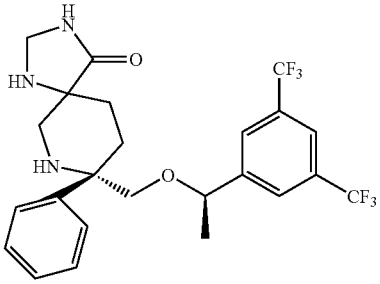

Step 1:

Compound 67a and 67b $\xrightarrow[\text{MeOH}]{\text{NaBH}_4}$

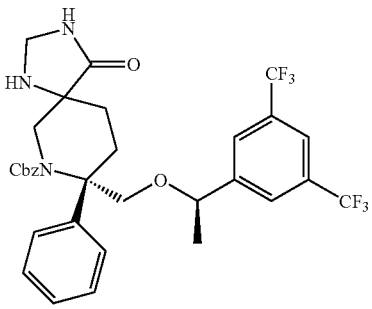

Compound 68

To a solution of a mixture of the two isomers of Compound 67 (0.27 g, 0.426 mmol, 1 equiv) in dry CH₃OH (3 ml) was added NaBH₄ (0.048 g, 1.28 mmol, 3 equiv). The reaction mixture bubbled upon the addition of the reagent, and was stirred for 5 h under N₂. The reaction was monitored by TLC (60/40 EtOAc/Hexane), and upon completion was quenched with HOAc, concentrated, diluted with EtOAc, washed with NaHCO₃ and dried over Na₂SO₄. The crude product was a mixture of two isomers, Compound 68, (0.25 g, 92%) and was carried forward without any purification.

Electrospray MS [M+1]⁺ 636.1 for the Compound 68.

Step2:

Example 82a (less polar isomer) and Example 82b (more polar isomer) (0.12 g, 61%) were prepared from Compound 68 using a similar procedure as for preparing Examples 79a and 79b from Compound 65.

Electrospray MS [M+1]⁺ 502.1 for Example 82a,
Electrospray MS [M+1]⁺ 502.1 for Example 82b.

Example 83

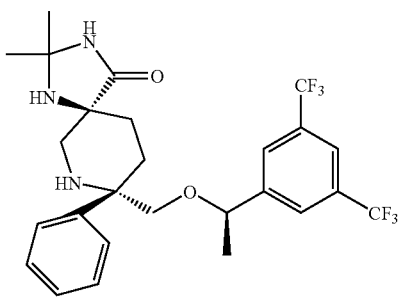

Step 1:

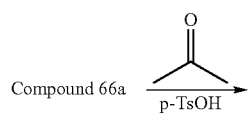

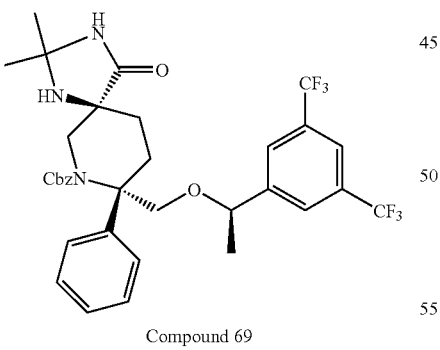

Compound 69

To a solution of Compound 66a (0.1 g, 0.16 mmol, 1 equiv) in a 25 ml RBF in MeOH (0.5 ml) was added acetone (0.352 ml, 0.48 mmol, 3 equiv) and p-TsOH (0.06 g, 0.32 mmol, 2 equiv). The reaction mixture was refluxed for 12 h and was monitored by mass spectrum analysis. Reaction upon completion was concentrated, diluted with EtOAc, washed with NaHCO₃, and dried over Na₂SO₄ to give Compound 69 (0.1 g, 94%). The crude product was carried forward without any purification.

Step 2:

Example 83 (0.026 g, 33%) was prepared from Compound 69 using a similar procedure as for preparing Examples 79a and 79b from Compound 65.

Electrospray MS [M+1]⁺ 530.1 for Example 83.

Examples 84a and Example 84b

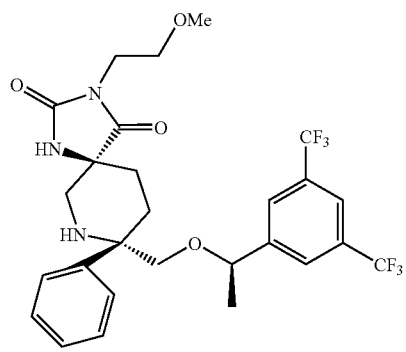

Example 84a

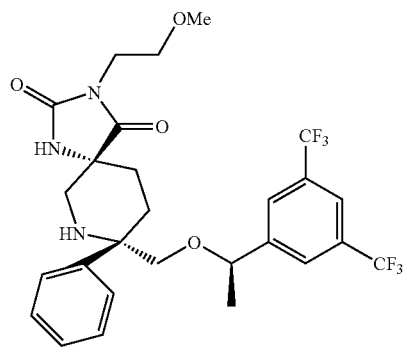

Example 84b

Examples 84a and Example 84b were prepared using a similar procedure as for Examples 78a and 78b, but using 2-bromoethyl methyl ether instead of 2-bromoethanol.

Electrospray MS [M+1]⁺ 574.1 for Example 84a,
Electrospray MS [M+1]⁺ 574.1 for Example 84b.

Example 85

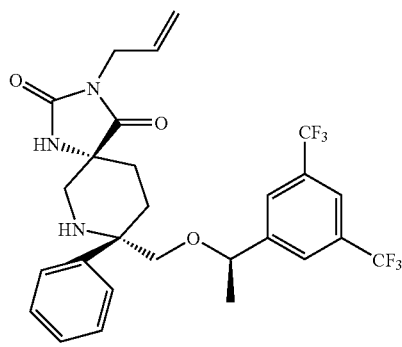

Example 85 (46 mg, 88%) was prepared from Example 43b using a similar procedure as for Compound 63, but using allyl bromide instead of 2-bromoethanol.

Electrospray MS [M+1]⁺ 556.1.

Examples 86a and Example 86b

Example 86a

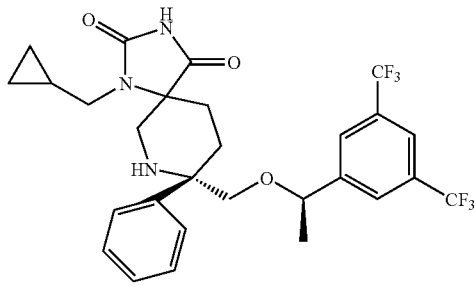

Example 86b

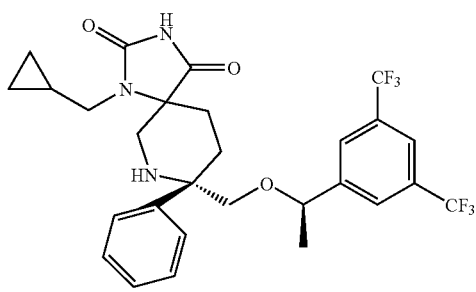

Step 1:

Compound 70

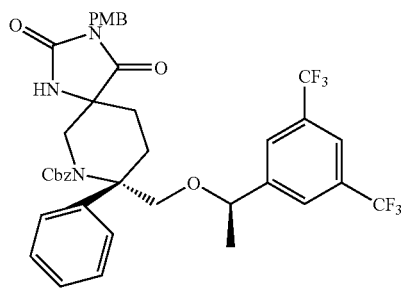

Compound 70 (1.14, 99%) was prepared from Compound 48 using a similar procedure as for Compound 63 but using para-methoxybenzyl chloride instead of 2-bromoethanol. Electrospray MS [M+1]+ 770.2.

Step 2:

Compound 70 →(NaH, DMF)→

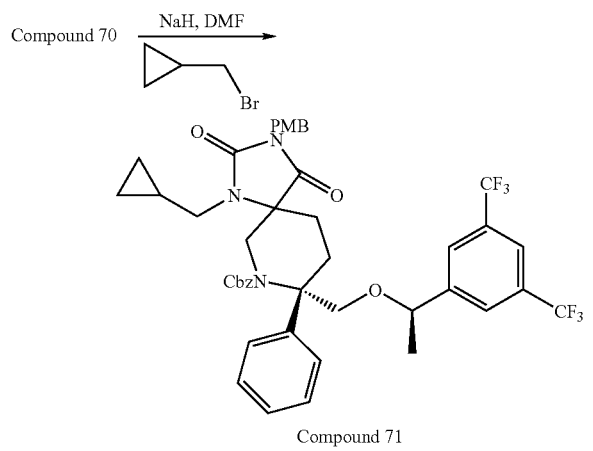

Compound 71

To a solution of Compound 70 (0.19 g, 0.25 mmol, 1 equiv) in 1.0 ml of anhydrous DMF at 0° C. was added NaH (60% dispersion in mineral oil, 0.012 g, 0.30 mmol, 1.2 equiv). After 5 min, the ice bath was removed and the reaction mixture was allowed to stir for 30 min before the addition of bromomethyl cyclopropane (0.029 ml, 0.30 mmol, 1.2 equiv). After 20 h, the reaction mixture was quenched with saturated NH$_4$Cl solution and diluted with EtOAc. The layers were separated and the organic layer was washed once with brine, dried over Na$_2$SO$_4$, filtered and concentrated to give Compound 71 (0.11 g, 99%) Electrospray MS [M+1]+ 824.2.

Step 3:

Compound 72

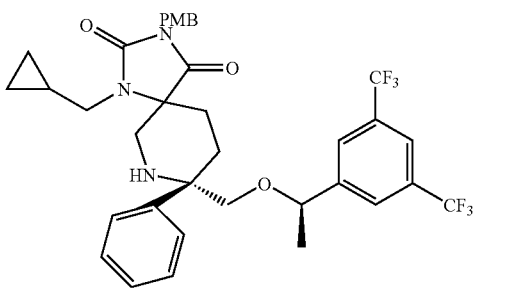

Compound 72 (0.24 g, 90%) was prepared from Compound 71 using a similar procedure as for Examples 78a and 78b from Compounds 63. Electrospray MS [M+1]+ 690.1.

Step 4:

To a solution of Compound 72 (0.24 g, 0.34 mmol, 1 equiv) in 5.0 ml of CH$_3$CN and 1.7 ml of water at 0° C. was added ammonium cerium nitrate (0.79 g, 1.4 mmol, 4 equiv). After 5 min the ice bath was removed and the reaction mixture was allowed to stir at RT for 17 h. The reaction mixture was quenched with water and diluted with EtOAc. The layers were separated and the organic layer was washed with water (100 ml×2), dried over Na$_2$SO$_4$, filtered and concentrated to give a yellow oil. Purification by chromatography on a Biotage eluting with the solvent gradient 20% EtOAc/hexane to 30% EtOAc/hexane to 50% EtOAc/hexane gave a diastereomeric mixture of Examples 86a and 86b (15 mg, 8%), isomerically pureless polar Example 86a (14 mg, 7%) Electrospray MS [M+1]+ 570.1, and isomerically pure more polar Example 86b (16 mg, 9%) Electrospray MS [M+1]+ 570.1.

Example 87

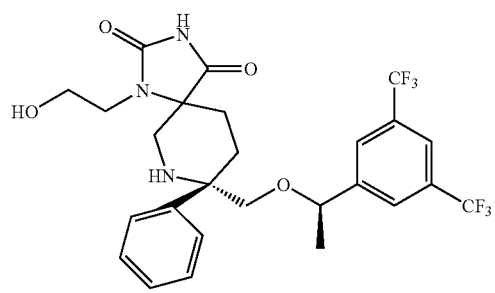

Step 1:

Compound 73

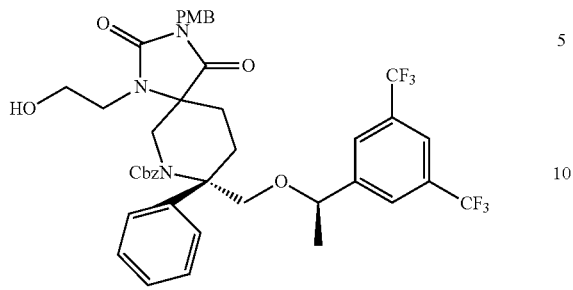

Compound 73 (0.20, 64%) was prepared from Compound 48 using a similar procedure as for Compound 63. Electrospray MS [M+1]$^+$ 814.19.

Step 2:

Compound 74

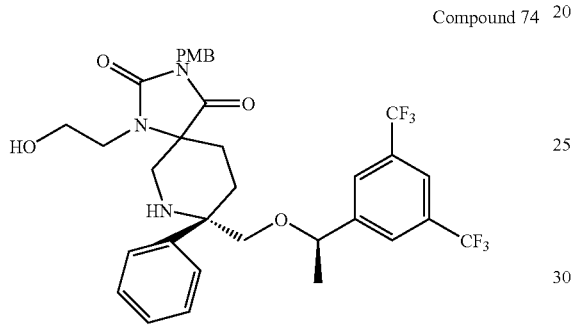

Compound 74 (0.16 g, 96%) was prepared from Compound 73 using a similar procedure as for Examples 78a and 78b from Compound 63. Electrospray MS [M+1]$^+$ 680.1.

Step 3:

Examples 87a and 87b were prepared from Compound 74 using a similar procedure as for Example 86a and 86b from Compound 72, but purification using a Gilson with water/CH$_3$CN was used instead of chromatography on a Biotage to isolate a diastereomeric mixture of Examples 87a and 87b (92 mg, 71%). HPLC separation on 50 mg of the mixture on a ChiralCel OD column using a (90/10) hexane/IPA as the eluent gave a diastereomeric mixture of Example 87a and 87b (11 mg), isomerically pure first-eluted product Example 87a (10 mg) Electrospray MS [M+1]$^+$ 560.1, and isomerically pure second-eluted product Example 87b (11 mg) Electrospray MS [M+1]$^+$ 570.1.

Example 88

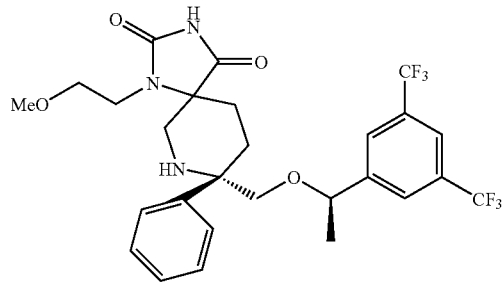

A diastereomeric mixture of Example 88a and 88b (22% overall yield in three steps from Compound 70) was prepared using a similar procedure as for Example 86a and 86b, but using 2-bromoethyl methyl ether instead of bromomethyl cyclopropane. HPLC separation on 50 mg of the diastereomeric mixture on a ChiralCel OD column using a (90/10) hexane/IPA as the eluent gave isomerically pure first-eluted product Example 88a (16 mg) Electrospray MS [M+1]$^+$ 574.3, and isomerically pure second-eluted product Example 88b (29 mg) Electrospray MS [M+1]$^+$ 574.3.

Example 89

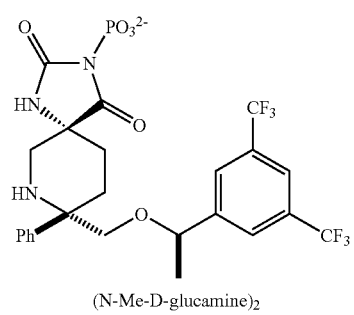

(N-Me-D-glucamine)$_2$

To a solution of Example 43b (0.68 g, 1.32 mmol, 1 equiv) in DMF (7 ml) at 0° C. was added NaH (60% in mineral oil, 0.105 g, 2.64 mmol, 2 equiv) and the mixture was stirred at 0° C. for 15 min. Tetravbenzyl pyrophosphate (1.42 g, 2.64 mmol, 2 equiv) was added and the reaction mixture stirred at 0° C. for 15 min, then warmed to 23° C. and stirred for 1 h. The reaction was quenched with saturated aq. NaHCO$_3$ (100 ml) and extracted with EtOAc (100 ml×3). The combined organic layers were dried (Na$_2$SO$_4$), filtered and concentrated. The crude product purified by column chromatography over Biotage (2:1, hexane:EtOAc) to afford the N-phosphorated hydantoin product (0.24 g) which was dissolved in MeOH (10 ml); N-Me-D-glucamine (0.119, 0.619 mmol, 2 equiv) was added, followed by 10% Pd—C (0.021 g). The resulting mixture was shaken in a parr shaker under H$_2$ atmosphere at 40 psi for 18 h. The reaction mixture was filtered through a pad of celite and the celite was washed with MeOH. The resulting solution was concentrated in vacuo. The residue was dissolved in EtOAc (100 ml) and extracted with water (100 ml) and the aqueous layer was lyophilized to give the desired product Example 89 as N-Me-D-glucamine salt (0.22 g, 21% over two steps).

Example 90

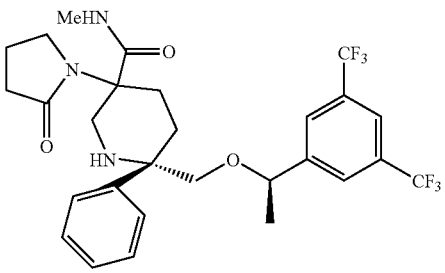

Step 1:

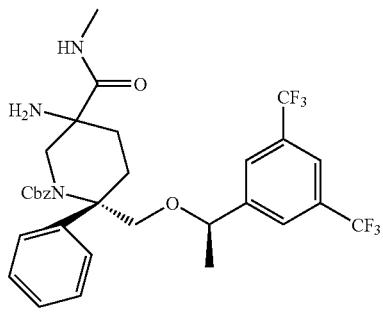

Compound 75

Compound 75 was prepared from Compound 48 using a procedure similar to the preparation of Compound 66 from Compound 48.

Step 2:

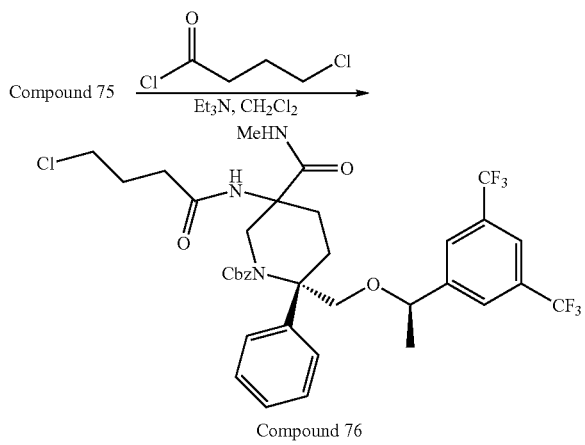

Compound 76

To a solution of the diastereomeric Compound 75 (0.10 g, 0.16 mmol, 1 equiv) in 2.0 ml of anhydrous CH$_2$Cl$_2$ at 0° C. was added Et$_3$N (0.033 ml, 0.24 mmol, 1.5 equiv) and 4-chlorobutyrylchloride (0.017 ml, 0.17 mmol, 1.1 equiv). After 6 h, the reaction mixture was quenched with saturated NH$_4$Cl solution and diluted with EtOAc. The layers were separated and the organic layer was washed once with brine, dried over Na$_2$SO$_4$, filtered and concentrated to give Compound 76 as a diastereomeric mixture (0.12 g, 100%) Electrospray MS [M+1]$^+$ 742.2.

Step 3:

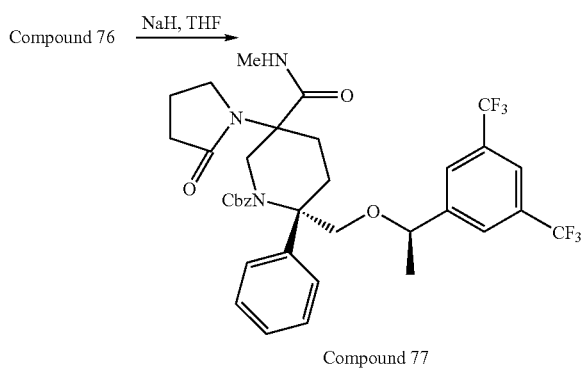

Compound 77

To a solution of Compound 76 (0.12 g, 0.16 mmol, 1 equiv).in 1.0 ml of anhydrous THF at RT was added NaH (60% dispersion in mineral oil, 0.010 g, 0.24 mmol, 1.5 equiv). After 3 h, the reaction mixture was quenched with saturated NH$_4$Cl solution and diluted with EtOAc. The layers were separated and the organic layer was washed once with brine, dried over Na$_2$SO$_4$, filtered and concentrated to give Compound 77 (0.10 g, 88%) Electrospray MS [M+1]$^+$ 706.2.

Step 4:

Examples 90a and 90b were prepared from Compound 77 using a similar procedure as for preparing Example 83 from Compound 69, but purification used chromatography on a Biotage instead of a Prep plate. A diastereomeric mixture of Examples 90a and 90b (26 mg, 32%)was obtained: less polar product Example 90a (20 mg, 25%) Electrospray MS [M+1]$^+$ 572.1, more polar product Example 90b (14 mg, 17%) Electrospray MS [M+1]$^+$ 572.1.

Example 91

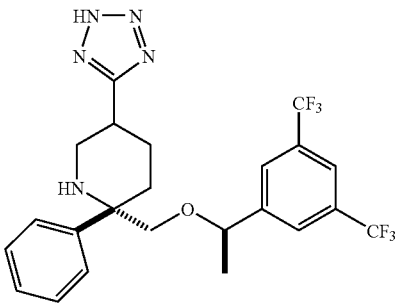

Step 1:

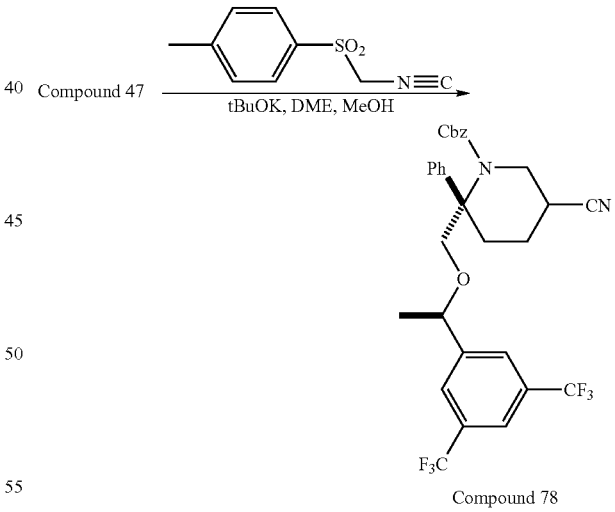

Compound 78

To a solution of Compound 47 (1 g, 1.73 mmol, 1 equiv) and tosylmethyl-isocyanide (374 mg, 1.9 mmol, 1.1 equiv) in anhydrous ethylene glycol dimethylether (11 ml) at −30° C., was added anhydrous MeOH (0.15 ml) followed by addition of potassium tert-butoxide (426 mg, 3.8 mmol, 2.2 equiv). After stirring at −30° C. to 10° C. for 7 h, the reaction mixture was passed through celite. The celite pad was thoroughly washed with Et$_2$O. The filtrate was concentrated and the residue was purified on silica gel column to afford the titled Compound 78 (470 mg, 46%).

Step 2:

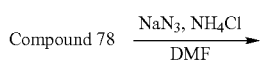

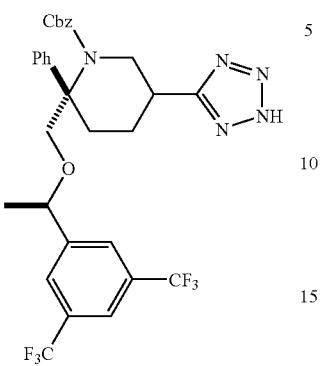

Compound 79

A solution of Compound 78 (125.7 mg, 0.21 mmol, 1 equiv) and NH₄Cl (68.3 mg, 1/28 mmol, 6 equiv) and NaN₃ (69.2 mg, 1.06 mmol, 5 equiv) in anhydrous DMF (1.2 ml) under N₂ was heated at 115° C. overnight. The mixture was concentrated, then acidified with HCl (6N, 10 ml) and extracted with EtOAc (15 ml×3). The combined organic solvent was dried over Na₂SO₄, filtered and evaporated in vacuum. The residue was purified on a silica gel column to afford Compound 79 (67 mg, 50%).

Step 3:

A solution of Compound 79 (65 mg, 0.103 mmol, 1 equiv) in EtOH (1.5 ml) was treated with 10% Pd—C (107 mg, 0.1 mmol, 1. equiv) and 1,4-cyclohexadiene (0.5 ml, 5.29 mmol, 50 equiv). The mixture was heated at 85° C. for 10 min, then passed through celite. The celite pad was washed with MeOH. The filtrate was concentrated in vacuum and the residue was purified by silica gel column to afford Example 91 (11 mg, 21%) Electrospray.MS [M+1]⁺ 500.1.

Example 92

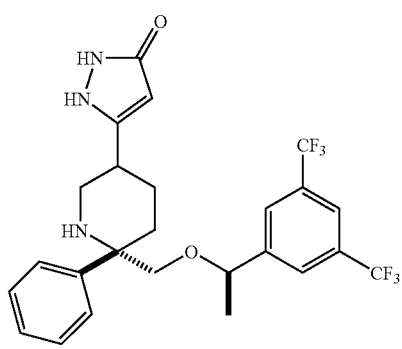

Step 1:

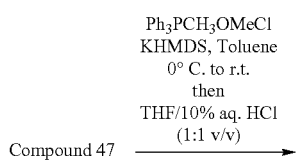

-continued

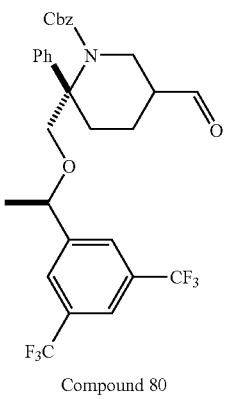

Compound 80

Compound 80 (72% yield) was prepared by similar procedure as for Compound 23 using Compound 47 in place of Compound 3.

Step 2:

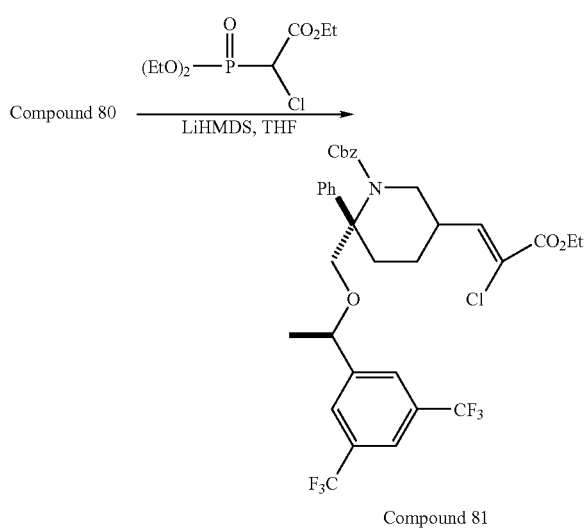

Compound 81

To a solution of triethyl 2-chloro-2-phophonoacetate (73 µl, 0.34 mmol, 1.05 equiv) in anhydrous THF (1.5 ml) at −78° C., was added dropwise of LiHMDS (0.35 ml, 0.35 mmol, 1.1 equiv, 1N solution in THF). The solution was stirred for 20 min before a solution of Compound 80 (192 mg, 0.32 mmol, 1 equiv) in dry THF (1 ml) was cannulated in. It was stirred at −78° C. for 2 h then quenched with saturated NH₄Cl aqueous solution, and extracted with Et₂O. The organic layer was dried over MgSO₄, filtered and concentrated to give the crude product which was purified by silica gel column to give Compound 81 (127 mg, 57%).

Step 3:

To a solution of Compound 81 (127 mg, 0.18 mmol, 1.0 equiv) in EtOH (1 ml) was added H₂NNH₂ (35 µl, 1.1 mmol, 6 equiv). It was stirred for 3 h and then concentrated in vacuum. The crude product was retaken up into EtOH (3 ml) and treated with 10% Pd/C (40 mg, 0.036 mmol, 0.2 equiv) and hydrogenated overnight. The catalyst was filtered off and washed with MeOH. The filtrate was concentrated to give the crude residue which was purified on silica gel column to afford less polar isomer Example 92a (14.2 mg, 15%), Electrospray MS [M+1]⁺ 514.1; and more polar isomer Example 92b (28.1 mg, 30%), Electrospray MS [M+1]⁺ 514.1

Example 93

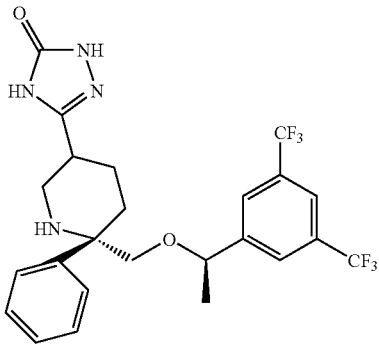

Step 1:

Compound 80 →(EDC, HOOBt / semicarbazide-HCl / DIEA, CH₂Cl₂)→

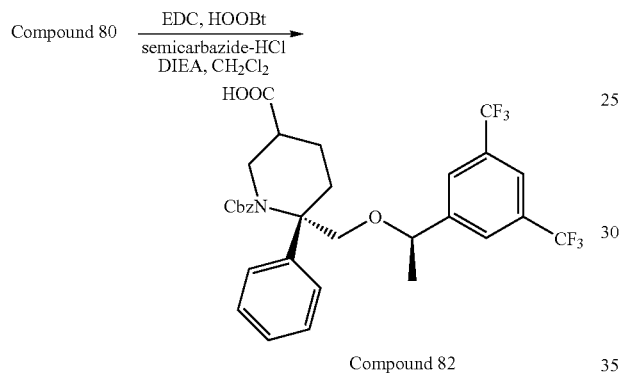

Compound 82

Compound 80 (0.74 g, 1.25 mmol, 1 equiv), was dissolved in t-BuOH (20 ml) and 2-methyl-2-butadiene (7 ml). To this solution was added a fresh solution of NaClO₂ (1.13 g, 12.5 mmol, 10 equiv.) in 20% (v/w) aq. NaH₂PO₄ solution. The reaction mixture was stirred at RT for 2 h. It was then diluted with EtOAc (200 ml) and the organic layer was separated, dried (Na₂SO₄), filtered and concentrated to give the crude Compound 82 which was used in the next reaction without further purification.

Step 2:

Compound 82 →(EDC, HOOBt / semicarbazide-HCl / DIEA, CH₂Cl₂)→

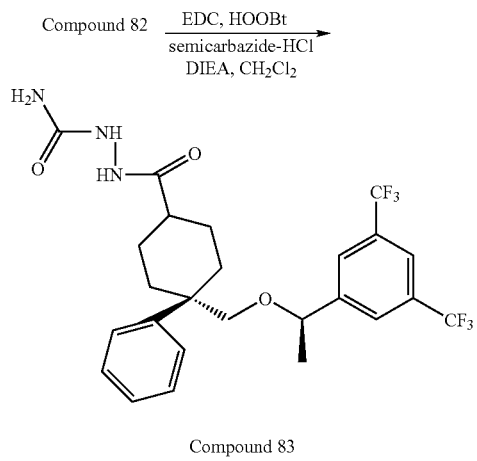

Compound 83

To a solution of the diastereomeric Compound 82 (0.33 g, 0.54 mmol, 1 equiv) in 2 ml of anhydrous CH₂Cl₂ at RT was sequentially added DIEA (0.11 ml, 0.65 mmol, 1.2 equiv), DEC (0.21 g, 1.1 mmol, 2 equiv), 3-hydroxy-1,2,3-benzotriazin4(3H)-one (0.18 g, 1.1 mmol, 2 equiv), and semicarbazide hydrochloride (0.072 g, 0.65 mmol, 1.2 equiv). After 3 h, the starting carboxylic acid was present by TLC [Hexane-EtOAc 1:1 (v/v)] and an additional amount of DIEA (0.11 mL, 0.65 mmol, 1.2 equiv) was added. After 2 days, the reaction mixture was quenched with saturated NaHCO₃ solution and diluted with EtOAc. The layers were separated and the organic layer was washed once with water and brine, dried over Na₂SO₄, filtered and concentrated to give an orange oil. Purification by chromatography on a Biotage eluting with the solvent gradient 50% EtOAc/hexane to 80% EtOAc/hexane to EtOAc to 5% MeOH/EtOAc gave Compound 83 as a.diastereomeric mixture (0.19 g, 54%) Electrospray MS [M+1]⁺ 667.07.

Step 3:

Compound 83 →(2M NaOH)→

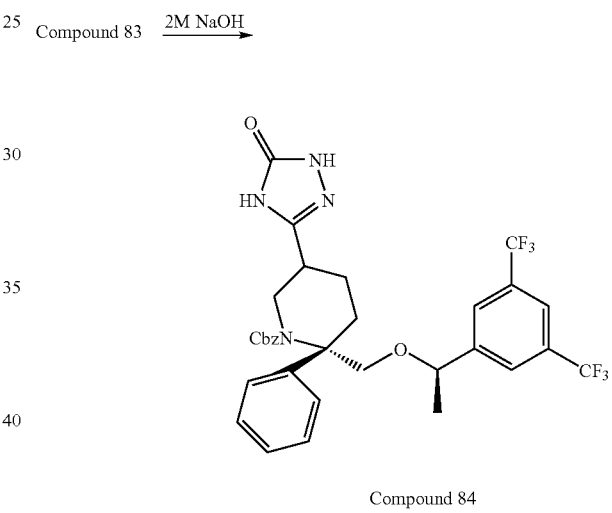

Compound 84

A solution of Compound 83 (0.17 g, 0.26 mmol, 1 equiv) in 8 ml of 2.0M NaOH solution was heated to reflux. After 15 h, the mixture was allowed to cool to RT and was neutralized with 1.0M HCl to pH6. The aqueous solution was diluted with EtOAc and the layers were separated. The organic layer was washed once with brine, dried over Na₂SO₄, filtered and concentrated to give a yellow oil (0.16 g). Purification by chromatography on a Biotage eluting with 3% MeOH/EtOAc gave Compound 84 as a diastereomeric mixture (0.12 g, 71%) Electrospray MS [M+1]⁺ 649.2.

Step 4:

Less polar product Example 93a and more polar product Example 93b (32 mg and 44 mg, total 88% for both isomers) were prepared from Compound 84 using a similar procedure as for preparing Examples 79a and 79b from Compound 65, but purification used chromatography on a Biotage instead of a Prep plate.

Electrospray MS [M+1]⁺ 515.3 for Example 93a.

Electrospray MS [M+1]⁺ 515.3 for Example 93b.

Example 94

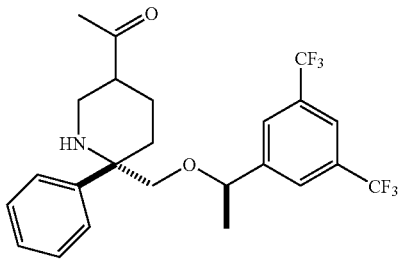

Step 1:

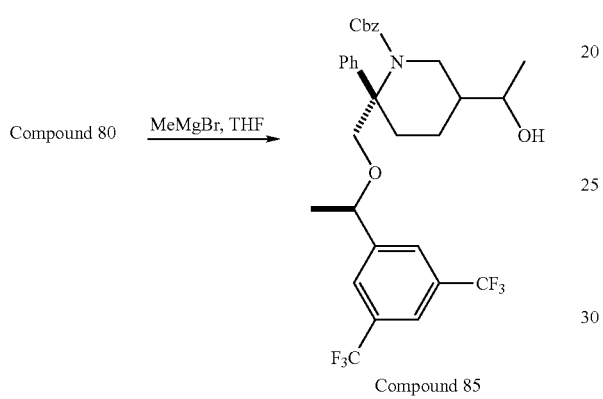

To a solution of Compound 80 (550 mg, 0.98 mmol, 1 equiv) in anhydrous THF (6 ml) at −10° C., was added dropwise CH₃MgBr (1.24 ml, 3.7 mmol, 4 equiv, 3.0M solution in Et₂O). The solution was stirred at −10° C. to 10° C. for 30 min. Aqueous work-up gave the crude product which was purified on silica gel column to afford Compound 85 (236 mg, 42%).

Step 2:

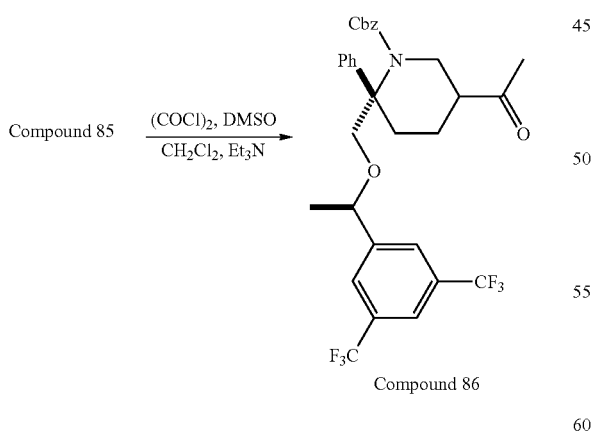

To a solution of DMSO (0.11 ml, 1.55 mmol, 4 equiv) in anhydrous CH₂Cl₂ (5 ml) at −78° C., was added dropwise oxalyl chloride (0.067 ml, 0.78 mmol, 2 equiv). The solution was stirred for 15 min before a solution of Compound 85 (236 mg, 0.387 mmol, 1 equiv) in dry CH₂Cl₂ (1 ml) was cannulated in. It was stirred at −78° C. for 1 h, then Et₃N (0.37 ml, 2.71 mmol, 7 equiv) was added dropwise. After stirring at −78° C. for 30 min, the cooling bath was removed and the reaction was warmed up to RT. It was quenched with saturated NH₄Cl aqueous solution, and extracted with CH₂Cl₂. The organic layer was dried over MgSO₄, filtered and concentrated to give the crude product, which was purified by silica gel column to give Compound 86 (140 mg, 60%).

Step 3:

To a solution of Compound 86 (1.0 equiv) in EtOH (3ml) was added 10% Pd/C (0.4 equiv) and the mixture hydrogenated overnight in a H₂ balloon atmosphere. The catalyst was filtered off and washed with MeOH. The filtrate was concentrated to give the crude residue which was purified on silica gel column to affordless polar isomer Example 94a (24 mg, 22%), Electrospray MS [M+1]⁺ 474.1; and more polar isomer Example 94b (32 mg, 29%), Electrospray MS [M+1]⁺ 474.1

Example 95

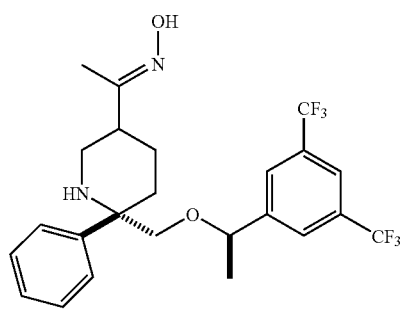

To a solution of Example 94a (16 mg, 0.033 mmol, 1 equiv) in anhydrous EtOH (1 ml) was added hydroxylamine hydrochloride salt (18 mg, 0.26 mmol, 7.7 equiv), and NaOAc (5 mg, 0.061 mmol, 1.8 equiv). The reaction mixture was stirred at RT overnight, then concentrated to dryness. The residue was retaken up with Et₂O, and washed with saturated NaHCO₃ aqueous solution. The organic layers were dried over MgSO4, filtered and concentrated in vacuum. The crude product was purified on silica gel column to afford Example 95 (12 mg, 74%), Electrospray MS [M+1]⁺ 489.1

Example 96

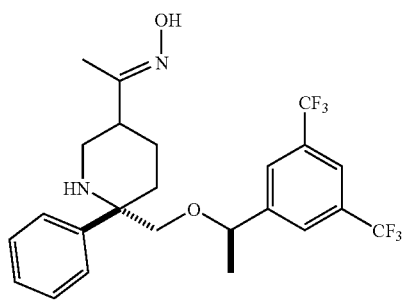

Example 96 (13 mg, 50%) was prepared by similar procedure as for Example 95 but using Example 94b in place of Example 94a. Electrospray MS [M+1]⁺ 489.1.

Example 97

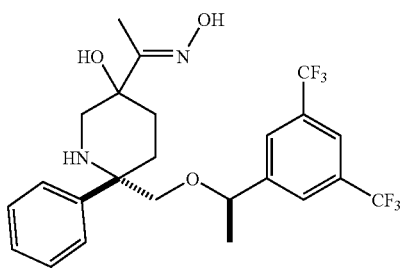

Step 1:

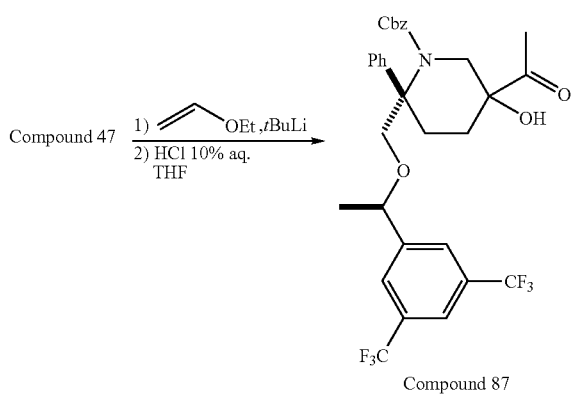

To a solution of ethyl vinylether (0.5 ml, 4.83 mmol, 12 equiv) in anhydrous THF (6 ml) at −78° C., was added dropwise tBuLi (0.73 ml, 1.24 mmol, 3 equiv, 1.7N solution in pentane). The solution was stirred at −10° C. bath until the orange color faded away. It was cooled to −78° C. again, and a solution of Compound 47 (240 mg, 0.41 mmol, 1 equiv) in dry THF (1 ml) was cannulated in. It was stirred at −78° C. for 1.5 h then was quenched with saturated $NH_4Cl$ aqueous solution and extracted with $Et_2O$. The organic layer was dried over $MgSO_4$, filtered and concentrated to give the crude product, which was retaken up into THF (6 ml) and treated with 10% HCl aqueous solution (0.8 ml). It was stirred at RT overnight. Alkaline aqueous work-up gave the crude product which was purified on silica gel column to afford Compound 87 (100 mg, 39%).

Step 2:

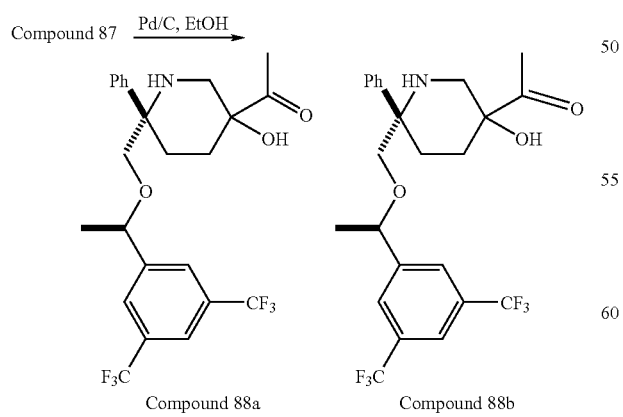

Compound 88a and Compound 88b were prepared using a similar procedure as for Examples 94a and 94b using Compound 87 instead of Compound 86. Separation by chiral HPLC column afforded Compound 88a (13 mg, 18%), and Compound 88b (10 mg, 14%).

Step 3:

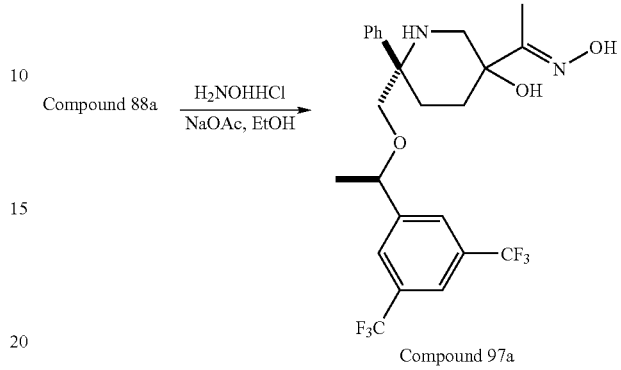

Example 97a (9.7 mg, 71%) was prepared using similar procedure as for Example 95 using Compound 88a in place of Example 94a. Electrospray MS $[M+1]^+$ 505.1

Step 4:

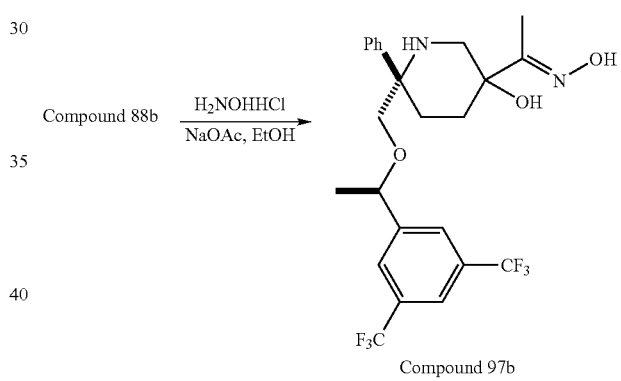

Example 97b (10.7 mg, 100%) was prepared using similar procedure as for Example 95 using Compound 88b in place of Example 94a. Electrospray MS $[M+1]^+$ 505.1

Example 98 and Example 99

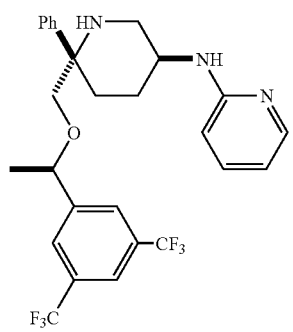

Example 98

Example 99

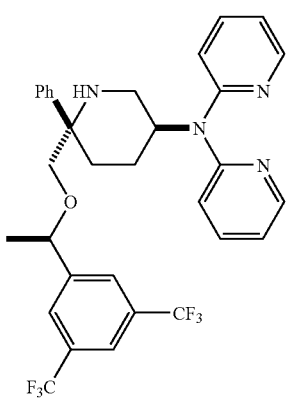

To Example 13 (340 mg, 0.76 mmol) in 1 ml toluene was added Pd$_2$(dba)$_3$ (27.8 mg, 0.03 mmol), BINAP (37.8 mg, 0.06 mmol), 2-bromopyridine (73 μl, 0.76 mmol) and NaOtBu (102 mg, 1.065 mmol). The mixture was concentrated in vacuo and the flask filled with N$_2$. The process was repeated once. The dark-brown solution was heated at 90° C. for 16 h. It was cooled to 23° C. and quenched with 2 ml pH7 buffer. The solution was extracted with EtOAc (10 ml×2). The organic layers were dried over Na$_2$SO$_4$ and concentrated. HPLC separation give Example 98, Electrospray MS M+1]$^+$ 524.1; and Example 99, Electrospray MS [M+1]$^+$ 601.1.

Example 100

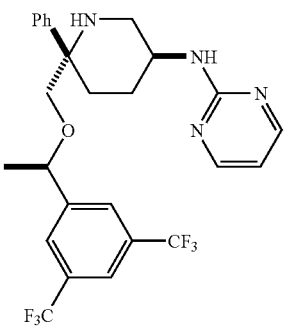

Example 100 was prepared using a similar procedure to Example 98, using 2-bromopyrimidine in place of 2-bromopyridine. Electrospray MS [M+1]$^+$ 525.1.

Example 101

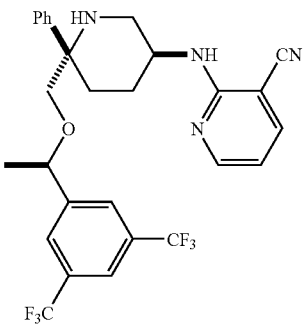

Example 101 was prepared using a similar procedure to Example 98, using 2-chloro-3-cyanopyridine in place of 2-bromopyridine. Electrospray MS [M+1]$^+$ 549.1.

Example 102

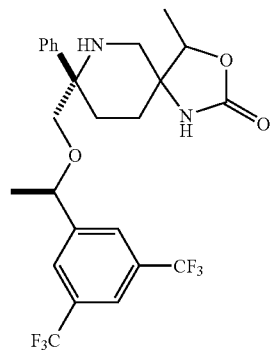

Step 1:

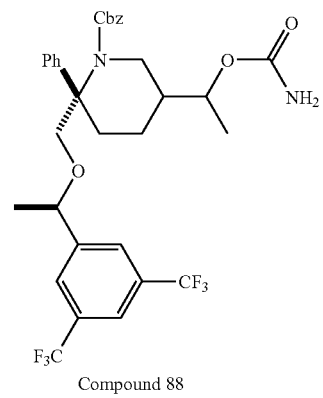

Compound 85 →(1) Cl$_3$CONCO; 2) K$_2$CO$_3$ MeOH)→ Compound 88

To Compound 85 (429 mg, 0.704 mmol) in CH$_2$Cl$_2$ (3.5 ml) at 0° C. was added Cl$_3$CONCO (100 ml, 0.844 mmol) dropwise. The solution was stirred at 0° C. for 2 h. The solvent was then removed and the residue was dissolved in MeOH (4 ml) and H$_2$O (1 ml). K$_2$CO$_3$(1.0 g) was added and the suspension was stirred for 14 h. The mixture was then diluted with 3 ml of water, concentrated to remove MeOH. The residue was extracted with EtOAc (10 ml×3). The combined organic layers were concentrated and passed through a short silica gel column to give product Compound 88 (420 mg, 91%).

Step 2:

Compound 88 →(PhI(OAc)2, Rh(OAc)2, MgO)→ 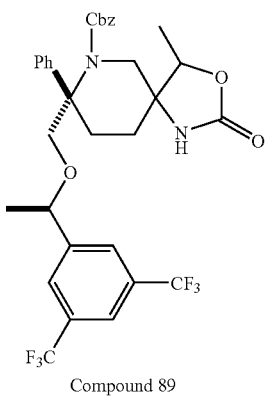

Compound 89

To Compound 88 (290 mg, 0.446 mmol) in CH$_2$Cl$_2$ (3 ml) was added PhI(OAc)$_2$ (131 mg, 0.625 mmol), Rh$_2$(OAc)$_4$ (12.9 mg, 0.022 mmol) and MgO (26.4 mg, 1.0 mmol). The suspension was heated at 40° C. for 16 h then cooled to 23° C. Celite (0.5 g) was added and the suspension was stirred for 5 min. The mixture was filtered and washed with EtOAC. The combined filtrate was concentrated and purified by chromatography on silica gel to give Compound 89 (60 mg, 31%).

Step 3:

Compound 89 transferred to a Parr shaker using 5 ml EtOH. 10% Pd—C (10%, 60 mg) was added and the suspension was hydrogenated at 40 psi overnight. The reaction mixture was filtered and concentrated. The residue was separated using HPLC on OD column eluted with 1:9 IPA/hexane to give two isomers, less polar isomer Example 102a, Electrospray MS [M+1]$^+$ 517.1 and more polar isomer Example 102b, Electrospray MS [M+1]$^+$ 517.1.

Example 103

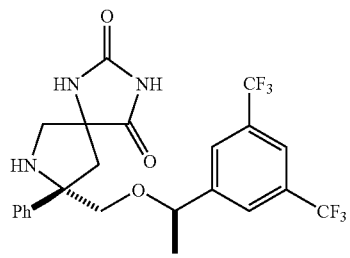

Step 1:

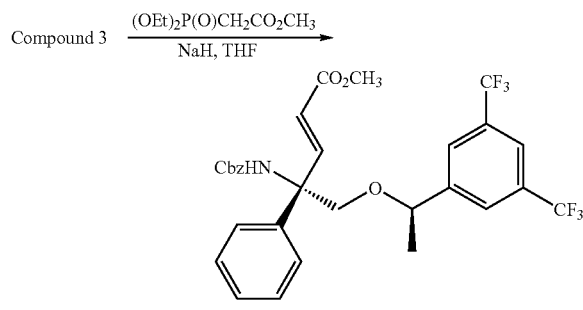

Compound 90

To a mixture of methyl diethylphosphonoacetate (9.5 ml, 51.77 mmol, 3 equiv) in dry THF (100 ml) at 0° C. under N$_2$ was added NaH (60% in mineral oil, 1.24 g, 51.77 ml, 3 equiv.). After being stirred at 0° C. for 15 min, a solution of Compound 3 (10 g, 17.26 mmol, 1 equiv) in THF (250 ml) was added. The mixture was warmed to 23° C. and stirred for 1 h and then quenched with saturated aq. NaHCO$_3$ solution (100 ml). The mixture was extracted with EtOAc (100 ml×3). The combined organic layers were dried (MgSO$_4$) and filtered. The crude product was purified by column chromatography over Biotage (4:1, hexane:EtOAc then 1:1, hexane:EtOAc) to afford the Compound 90 (8.88 g, 86%), Electrospray MS [M+1]$^+$ 596.1.

Step 2:

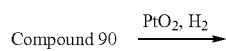

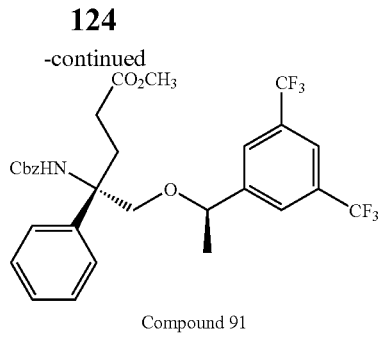

Compound 91

Compound 91 was prepared from Compound 90 using the procedure similar to the preparation of Compound 44 from Compound 42. The crude Compound 91 was used in the next reaction without further purification.

Step 3:

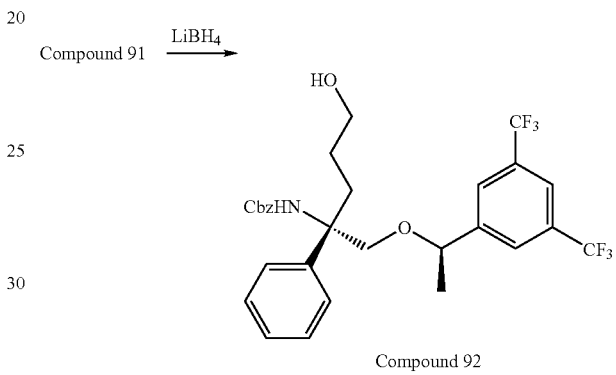

Compound 92

To a solution of Compound 91 (8.8 g, 14.73 mmol, 1 equiv.) in dry THF (150 ml) was added LiBH$_4$ (0.58 g, 26.51 mmol, 1.8 equiv.) and the reaction mixture was stirred at 0° C. for two h. The reaction mixture was cooled to 0° C. over an ice bath and quenched with saturated NaHCO$_3$ (50 ml). The reaction mixture was extracted with EtOAc (3×100 ml). The combined organic layers were dried (Na$_2$SO$_4$), filtered and concentrated to give crude Compound 92 (8.2 g), Electrospray MS [M+1]$^+$ 570.1, which was used in the next reaction without further purification.

Step 4:

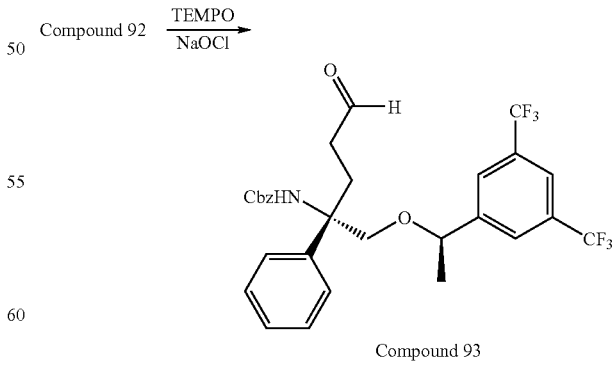

Compound 93

To a solution of Compound 92 (8.2 g, 14.4 mmol, 1.0 equiv.) in EtOAc (150 ml) at 0° C. was added saturated aq. NaHCO$_3$ (150 ml) and the reaction mixture was stirred for 10 min at 0° C. NaBr (1.5 g, 14.4 mmol, 0.01 equiv.) was added to the reaction mixture, followed by TEMPO (0.0225 g, 0.144 mmol, 0.1 equiv), and bleach (5.25% in H2O, 20.4 ml, 14.4 mmol, 1.0 equiv.). The reaction mixture was stirred for 15 min at 0° C. The reaction was monitored by TLC in 1:2 EtOAc/hexane which indicted presence of starting material. Additional NaOCl (2 ml) was added to the reaction mixture and was stirred for 15 min at 0° C. and then it was quenched with saturated Na₂S₂O₃ (20 ml). The reaction mixture was extracted with EtOAc (1 50 ml×3). The combined organic layers were dried over (MgSO₄), filtered and concentrated to give crude Compound 93 (8 g) which was used in the next reaction without further purification.

Step 4:

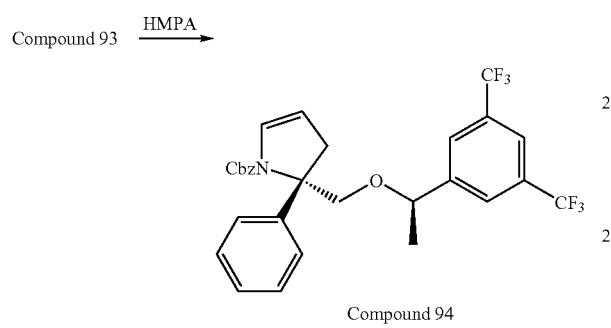

Compound 94

A mixture of Compound 93 (8 g, 14.1 mmol, 1.0 equiv.) and HMPA (50 ml) was heated at 170° C. for two h. The reaction mixture was cooled to 23° C. and quenched with water (50 ml). The reaction mixture was extracted with Et₂O (150 ml×3). The combined organic layers were dried over (MgSO₄), filtered and concentrated. The crude product purified by column chromatography over Biotage (7:3, hexane:EtOAc) to afford Compound 94 (3.8 g, 40% over three steps), Electrospray MS [M+1]⁺ 550.1.

Step 5:

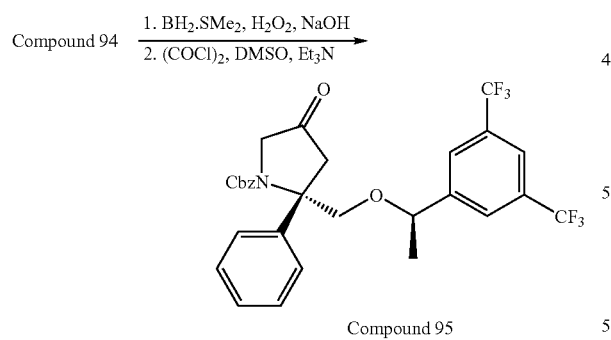

Compound 95

Compound 95 was prepared from Compound 94 using the procedure similar to the preparation of Compound 47 from Compound 45. Electrospray MS [M+1]⁺ 566.1.

Step 6:

Compound 95 was converted to less polar isomer Example 103a, Electrospray MS [M+1]⁺ 502.1, and more polar isomer Example 103b, Electrospray MS [M+1]⁺ 502.1, using the procedure similar to the preparation of Example 43a and Example 44b from Compound 47.

Example 104

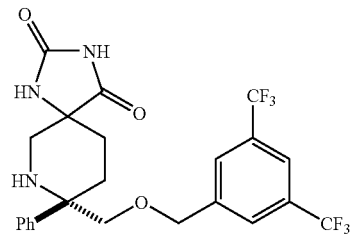

Step 1:

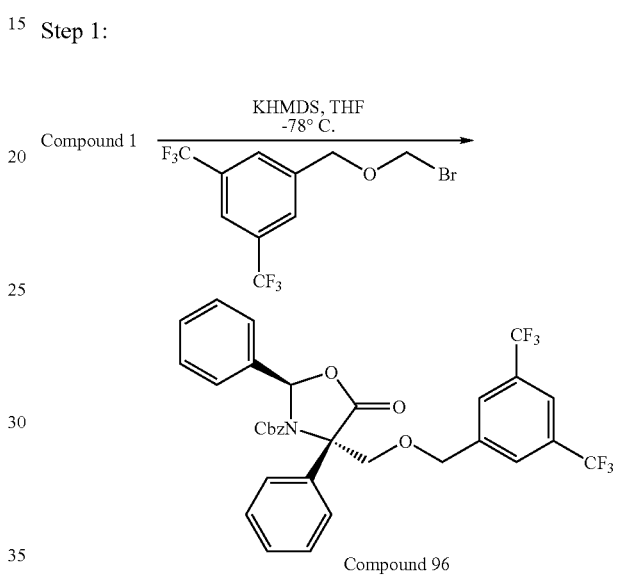

Compound 96

Compound 96 was prepared from Compound 1 using the procedure similar to the preparation of Compound 3 from Compound 1. Electrospray MS [M+1]⁺ 566.1 for the Compound 106.

Step 2:

Compound 96 was converted to a mixture of Example 104a and Example 104b using the procedure similar to the preparation of Examples 43a and 44b from Compound 2. The mixture of two isomers was separated on HPLC "ChiralPak AD column" using (5:95, IPA:hexane) to afford pure less polar isomer Example 104a, Electrospray MS [M+1]⁺ 502.1 and more polar isomer Example 104b, Electrospray MS [M+1]⁺ 502.1.

Example 105

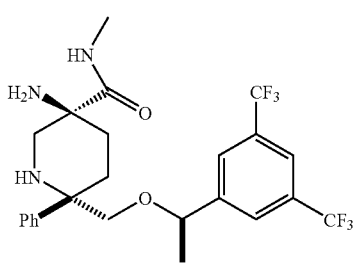

Example 105 was prepared from Compound 54 using the procedure similar to the preparation of Compound 62 from Compound 54, but using $CH_3NH_2$ (2M in THF) in place of ammonia (0.5M in 1,4-dioxane). Electrospray MS $[M+1]^+$ 504.1.

Example 106a and Example 106b

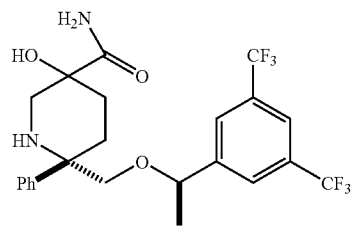

Example 106a

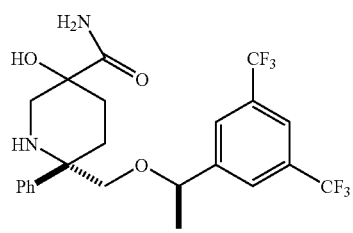

Example 106b

Step1:

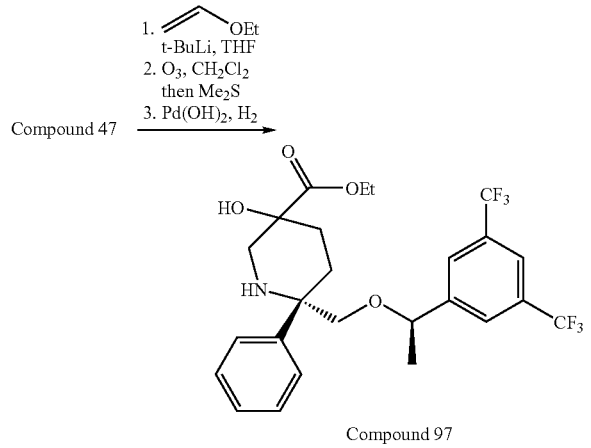

To a solution of ethyl vinyl ether (2.51 ml, 26.1 mmol) in THF (50 ml) at −78° C. under $N_2$, t-BuLi (6.6 ml, 11.2 mmol, 1.7M in pentane) was added. The mixture was warmed to 0° C. and stirred until the color of the solution turned pale yellow. The mixture was then re-cooled at −78° C. and a solution of Compound 47(2.16 g, 3.73 mmol) in THF (20 ml) was added. The mixture was stirred at −78° C. for 1 h before quenched with saturated $NaHCO_3$ solution. Water and $Et_2O$ were added to the mixture. Layers were separated and the aqueous layer was extracted with $Et_2O$ (200 ml×2). The combined organic layers were dried ($K_2CO_3$, $Na_2SO_4$) and filtered. Solvents were removed in vacuum to give an alcohol as yellow oil. The alcohol was dissolved in $CH_2Cl_2$ (20 ml) and ozone was bubbled through the solution at −78° C. until pale blue color persisted. $(CH_3)_2S$ (2.7 ml, 37.3 mmol) was added and the mixture was warmed to RT. Solvents were removed in vacuum and purification by column chromatography $[CH_2Cl_2]$ gave an ester as colorless oil. The ester was dissolved in EtOH (20 ml) and a catalytic amount of $Pd(OH)_2$ (20% on carbon) was added. The mixture was shaken in a Parr hydrogenator at 45 psi overnight. The mixture was filtered through a pad of Celite and solvents were removed in vacuum to give a colorless oil. Separation by column chromatography [hexane-EtOAc, 4:1(v/v)] gave Compound 97 as colorless oil.

Step 2:

Compound 97 was dissolved in $CH_3OH$ (10 ml) and ammonia was bubbled through the solution for 30 min. The mixture was stirred at RT overnight and solvents were removed in vacuum to give a yellow oil. Separation by HPLC using Chiralcel OD [hexane-isopropanol, 9:1 (v/v)] gave the less polar major isomer Example 106a (15% overall) as white foam. Electrospray MS $[M+1]^+$=491.1. Continuous elution with the same solvent system gave the more polar minor isomer Example 106b (10% overall) as white foam. Electrospray MS $[M+1]^+$=491.1.

Example 107

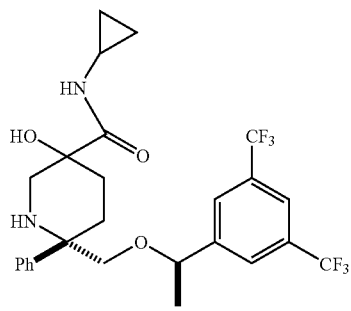

To a solution of cyclopropylamine (17 μl, 0.20 mmol) in toluene (1 ml) at RT under $N_2$, $Al(CH_3)_3$(0.1 ml, 0.20 mmol, 2.0M in toluene) was added. The mixture was allowed to stir at RT for 20 min. and a solution of Compound 97 (20 mg, 0.040 mmol) in toluene (1 ml) was added. The mixture was heated at 60° C. overnight and was cooled to RT. EtOAc was added and the mixture was quenched with saturated potassium sodium tartarate solution. The layers were separated and the aqueous layer was extracted with EtOAc (100 ml×2). The combined organic layers were dried ($MgSO_4$) and filtered. Solvents were removed in vacuum and purification by column chromatography [hexane-EtOAc, 2:1 (v/v)] gave Example 107 (11 mg, 56%) as colorless oil. Electrospray MS $[M+1]^+$=531.

Example 108

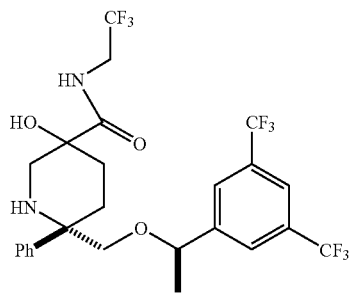

Example 108a and Example 108b were prepared from Compound 97 using the procedure similar to the preparation of Example 107 from Compound 97 but using 2,2,2-trifluoroethylamine in place of cyclopropylamine. Electrospray MS [M+1]+ 573.1 for the less polar isomer Example 108a and Electrospray MS [M+1]+ 573.1 for the more polar isomer Example 108b.

Example 109

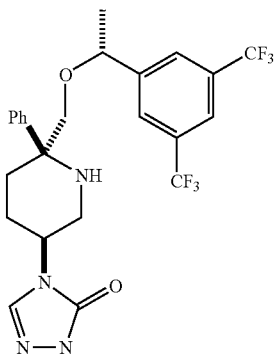

Step 1:

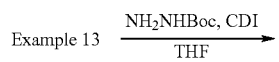

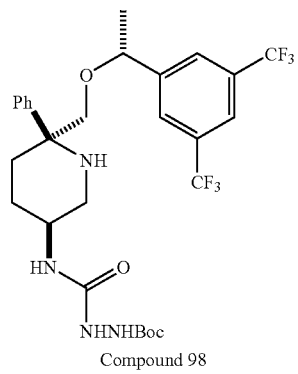
Compound 98

To a solution of diamine Example 13 (150 mg, 0.336 mmol, 1 equiv) in anhydrous THF (5 ml) at 0° C. was added tert-butylcarbazine (44.4 mg, 0.336 mmol, 1 equiv) followed by CDI (65.4 mg, 0.404 mmol, 1.2 equiv). The reaction mixture was warmed to RT and stirred for 2 h. The reaction mixture was then concentrated and purified on a biotage (5:95 MeOH/EtOAc) to give Compound 98 (170 mg, 84%), Electrospray MS [M+1]+ 605.3.

Step 2:

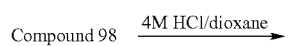

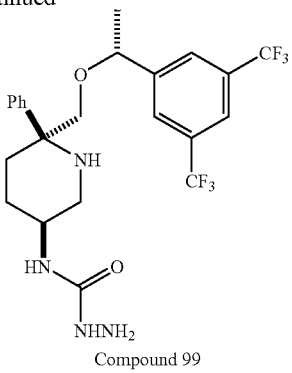
Compound 99

To a solution of Compound 98 (170 mg, 0.281 mmol, 1 equiv) in anhydrous CH2Cl2 (15 ml) at 0° C. was added a 4M HCl solution in 1,4-dioxane (0.7 ml, 2.81 mmol, 10 equiv). The reaction mixture was warmed to RT and stirred for 18 h. The reaction mixture was quenched with sat. aq. NaHCO3 (100 ml) and extracted with EtOAc (2×150 ml). The organic layer was dried (Na2SO4), filtered and concentrated. The crude product Compound 99 was used in the next reaction without further purification.

Step 3:

To a solution of Compound 99 (160 mg, 0.317 mmol, 1 equiv) in anhydrous DMF (5 ml) was added formaimidine acetate (165 mg, 1.6 mmol, 5 equiv) and the reaction mixture was stirred at RT for 30 min. HOAc (0.091 ml, 1.6 mmol, 5 equiv) was added and the reaction mixture was heated at 80° C. for 6 h. The reaction mixture was then cooled to RT, poured into EtOAc (200 ml) and washed with water (3×100 ml). The organic layer was dried (Na2SO4), filtered and concentrated. The crude mixture was purified on Gilson (1:9 H2O/CH3CN) to give Example 109 (50 mg, 35%), Electrospray MS [M+1]+ 515.3.

Example 110a and Example 110b

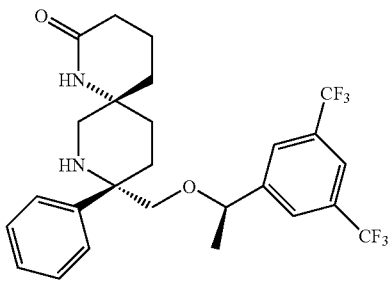
Example 110a

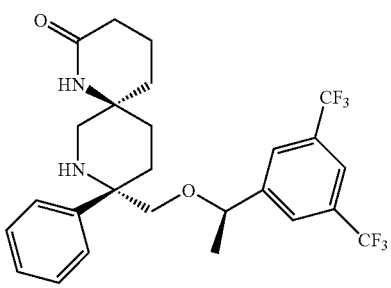
Example 110b

Step 1:

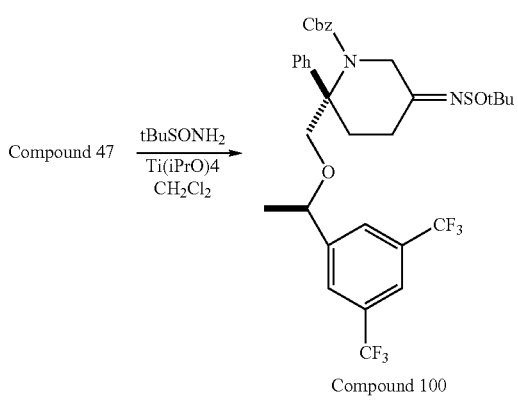
Compound 100

Using a procedure similar to Example 11, step 2, Compound 47 was converted to the corresponding sulfinimine, Compound 100.

Step 2:

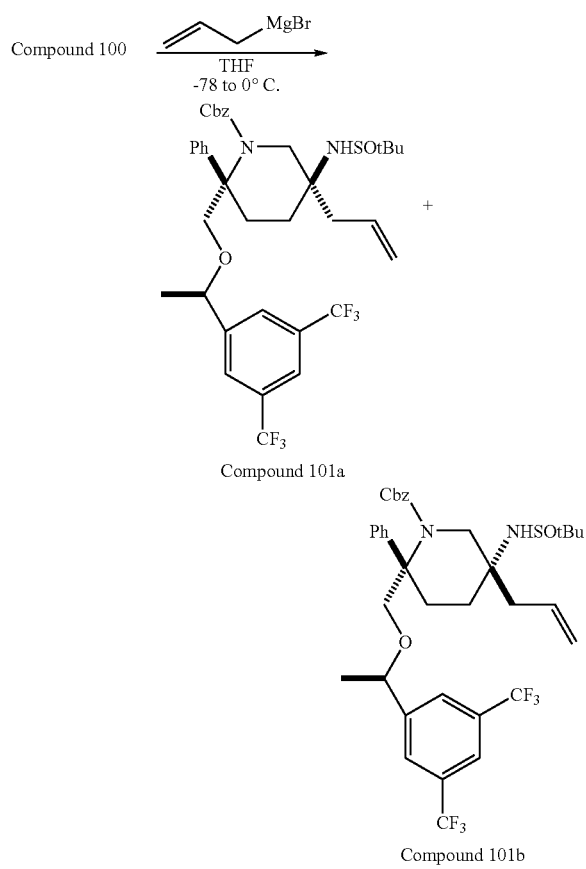

Following a procedure similar to Example 11, Step 3, Compound 100 was converted to sulfinamide Compounds 101a and 101b.

Step 3:

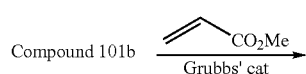

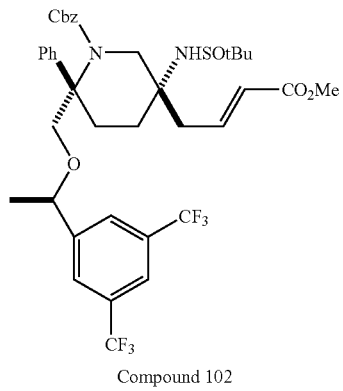
Compound 102

A 15 ml pear-shaped flask was charged with Compound 101b (140 mg, 0.193 mmol, 1 equiv) and $CH_2Cl_2$ (1 ml). To this pale yellow solution was added Grubbs' catalyst (13.7 mg, 0.016 mmol, 0.084 equiv), and methyl acrylate (21 μl, 0.232 mmol, 1.2 equiv). The resulting reddish solution was heated at 40° C. overnight and quenched with methylsulfoxide (0.2 ml). After stirring at RT for 20 h, it was diluted with $Et_2O$ and washed with water. The organic layer was dried over $MgSO_4$, filtered, and concentrated. The residue was purified by silica column to give Compound 102 (100 mg, 66%).

Step 4:

A RBF was charged with Compound 102 (100 mg, 0.128 mmol, 1 equiv) in EtOH (3 ml), and $Pd(OH)_2$ on carbon (90 mg, 0.128 mmol, 1 equiv, 20% wt). A hydrogen balloon was attached on the top and the mixture was hydrogenated overnight. The reaction mixture was carefully passed through a celited funnel and the celite pad was washed thoroughly with MeOH. The filtrate was concentrated, then re-taken up into MeOH (2 ml), treated with HCl (2 ml, 4.0M in 1,4-dioxane), stirred at RT for 2 h, then concentrated again, retaken up again into MeOH (5 ml), treated with an excess amount of $K_2CO_3$, and heated at 50° C. for 3 h, filtered, concentrated, and the resulted residue was purified on a silica column to afford Example 110a (42 mg, 64%), Electrospray MS [M+1]+ 515.1

Example 110b (49%) was prepared by a similar procedure, but using Compound 101a. Electrospray MS [M+1]+ 515.1

Example 111a and Example 111b

Example 111a

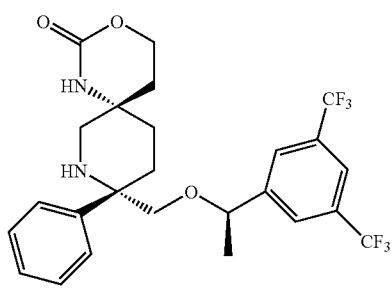

Example 111b

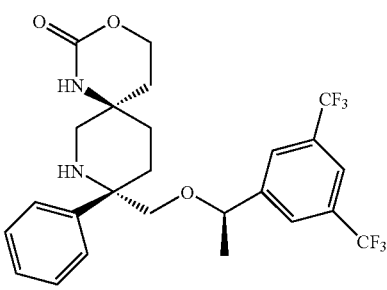

Step 1:

Compounds 101a and 101b  →  1) O₃  2) NaBH₄

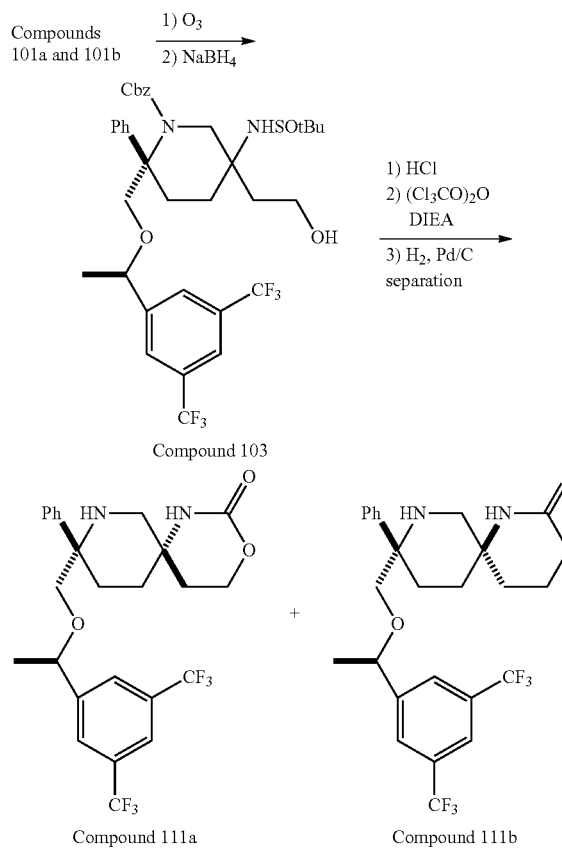

An RBF was charged with a mixture of Compound 101a and 101b (180 mg, 0.248 mmol, 1.0 equiv) and CH$_2$Cl$_2$ (2 ml). This pale orange solution was cooled to −78° C., and then O$_3$ was bubbled in. After the solution turned pale blue, the reaction solution was stirred at −78° C. for 10 min, then it was -flushed with N$_2$ to get rid of O$_3$. The solvent was then removed carefully. The residue was dissolved in EtOH followed by addition of NaBH$_4$ (120 mg). The solution was stirred at RT for 12 h. It was quenched with NH$_4$Cl solution. The reaction was extracted with EtOAc (3×10 ml). The organic solution was washed with brine, dried and concentrated to give Compound 103, which was used in the next reaction without further purification.

The crude Compound 103 was dissolved in MeOH (2 ml) and cooled to 0° C., followed by the addition of HCl (6 ml, 4N in dioxane). After stirring for 3 h, the solvent was removed and the residue was redissolved in 3 ml CH$_2$Cl$_2$, followed by the addition of DIEA (178 μl). The solution was cooled to 0° C., triphosgene (36 mg) was added, and the reaction was allowed to warm to RT and stirred for 3 h. It was then diluted with EtOAc, washed with 5% HCl, NaHCO$_3$ (aq.) and brine. The organic layers were dried with Na$_2$SO$_4$, filtered and concentrated. The crude product was hydrogenated to give a mixture of Example 111a and 111b. The mixture was separated using prep TLC (5% MeOH in CH$_2$Cl$_2$) to give Example 111a (less polar) and Example 111b (more polar). Electrospray MS Example 111a [M+1]$^+$ 517.1; Example 111a [M+1]$^+$ 517.1.

Example 112

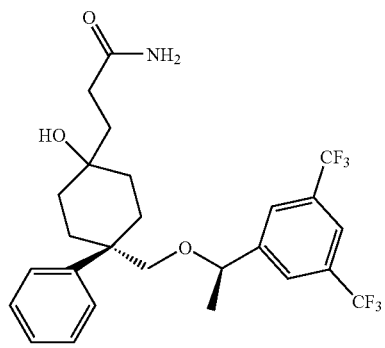

To a solution of ethyl propiolate (83 μl, 0.82 mmol) in THF (2 ml) at −78° C. under N$_2$, t-butyllithium (0.48 ml, 0.82 mmol, 1.7M in pentane) was added. The mixture was stirred at −78° C. for 10 min and a solution of Compound 47 (158 mg, 0.27 mmol) in THF (1 ml) was added. The mixture was stirred at −78° C. for 1 h before quenching with HOAC at −78° C. Water and EtOAc were added to the mixture. Layers were separated and the aqueous layer was extracted with EtOAc (200ml×2). The combined organic layers were dried (MgSO$_4$) and filtered. Solvents were removed in vacuum and purification by column chromatography.[hexanes-EtOAc, 4:1 (v/v)] gave a colorless oil (112 mg, 61%). The oil was dissolved in EtOH and catalytic amount of palladium (10% on charcoal) was added. The mixture was shaken in a Parr hydrogenator at 45 psi overnight. The mixture was filtered through a pad of celite and solvents were removed in vacuum to give an ester as a colorless oil. The oil was dissolved in CH$_3$OH (10 ml) and ammonia was bubbled through the solution for 30 min. The mixture was stirred at RT overnight and solvents were removed in vacuum. Purification by column chromatography [CH$_3$OH-EtOAc, 1:9 (v/v)] gave Example 112 as a colorless oil (54 mg, 61%). Electrospray MS [M+1]$^+$=519.1.

Examples 113a and 113b

Example 113a

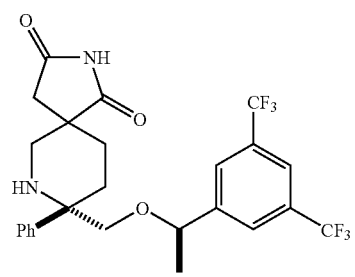

-continued

Example 113b

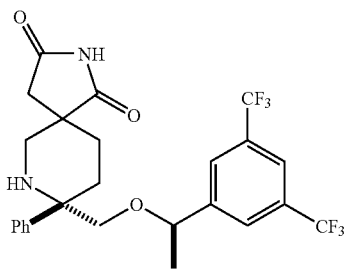

To a solution of Compound 51 (1.97 g, 3.10 mmol) in $CH_2Cl_2$ (50 ml) at −78° C., DIBAL-H (9.3 ml, 9.3 mmol, 1.0 M in toluene) was added. The mixture was stirred at −78° C. for 1 h before it was quenched with saturated potassium sodium tartrate solution. The mixture was warmed to RT and water and EtOAc were added. Layers were separated and the aqueous layer was extracted with EtOAc (200 ml×2). The combined organic layers were dried ($MgSO_4$) and filtered. Solvents were removed in vacuum and column chromatography [hexane-EtOAc, 3:1(v/v)] gave the allylic alcohol (1.6 g, 85%) as colorless oil.

The allylic alcohol (1.6 g, 2.63 mmol) was dissolved in triethylorthoacetate (30 ml) and catalytic amount of propanoic acid was added. The mixture was heated in a sealed-tube at 130° C. overnight. Solvents were removed in vacuum and column chromatography [hexane-$Et_2O$, 5:1 (v/v)] gave the alkene (891 mg, 50%) as colorless oil.

The alkene (891 mg, 1.31 mmol) was dissolved in $CH_2Cl_2$ (20 ml) and was cooled at −78° C. $O_3$ was bubbled through the solution until a pale blue color persisted in the solution. The mixture was purged with $N_2$ until a colorless solution was obtained. Methyl sulfide (1 ml) was added and the mixture was warmed to RT. Solvents were removed in vacuum and column chromatography [Hexanes-EtOAc, 5:1(v/v)] gave the aldehyde (800 mg, 90%) as colorless oil.

The aldehyde (280 mg, 0.41 mmol) was dissolved in isoprene (2.4 ml) and t-butyl alcohol (7 ml) at RT. A solution of sodium chlorite (414 mg, 4.12 mmol) in sodium dihydrogenphosphate (4 ml, 20% wt. in water) was added. The mixture was stirred at RT vigorously for 2 h. Water and EtOAc were added. Layers were separated and the aqueous layer was extracted with EtOAc (250 ml×2). The combined organic layers were dried ($MgSO_4$) and filtered. Solvents were removed in vacuum to give a crude acid as yellow oil.

The crude acid was dissolved in $CH_2Cl_2$ (10 ml) at RT and diisopropylamine (0.22 ml, 1.24 mmol), followed by PyBOP (322 mg, 0.62 mmol) were added. The mixture was stirred at RT for 20 min. before a solution of ammonia in dioxane (8 ml, 4.12 mmol) was added. The mixture was stirred at RT overnight before it was quenched with saturated $NaHCO_3$ solution. Water and EtOAc were added. Layers were separated and the aqueous layer was extracted with EtOAc (250 ml×2). The combined organic layers were dried ($MgSO_4$) and filtered. Solvents were removed in vacuum to give the crude amide as yellow oil.

The crude amide was dissolved in $CH_3OH$ (10 ml) and $Pd(OH)_2$ (20% on carbon) was added. The mixture was stirred under $H_2$ (balloon) for 4 h. Solid was filtered through a pad of celite and solvents were removed in vacuum to give the crude amino-amide as yellow oil.

The crude amino-amide was dissolved in $CH_3OH$ and excess $NaOCH_3$ was added. The mixture was heated at 60° C. for 1 h before it was quenched with saturated with saturated $NH_4Cl$ solution. Water and EtOAc were added. Layers were separated and the aqueous layer was extracted with EtOAc (250 ml×2). The combined organic layers were dried ($MgSO_4$) and filtered. Solvents were removed in vacuum and column chromatography [hexane-EtOAc, 2:1 (v/v)] gave the less polar isomer Example 113a (20 mg, 9%, 4 steps overall) as white foam. Electrospray MS $[M+1]^+=515.1$. Continuous elution with the same solvent system gave the more polar isomer Example 113b (25 mg, 12%, 4 steps overall) as colorless oil.

Electrospray MS $[M+1]^+=515.1$.

The above description is not intended to detail all modifications and variations of the invention. It will be appreciated by those skilled in the art that changes can be made to the embodiments described above without departing from the inventive concept. It is understood, therefore, that the invention is not limited to the particular embodiments described above, but is intended to cover modifications that are within the spirit and scope of the invention, as defined by the language of the following claims.

What is claimed is:

1. A compound having the formula (I):

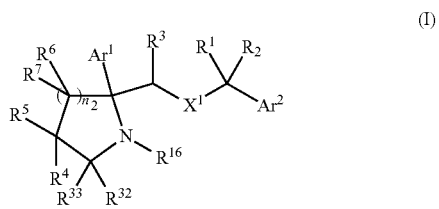

(I)

or a pharmaceutically acceptable salt thereof, wherein
$Ar^1$ is phenyl, wherein said phenyl can be unsubstituted or substituted with 1 to 3 fluoro;
$Ar^2$ is bis(trifluoromethyl)phenyl;
$X^1$ is —O—;
$R^1$ and $R^2$ are independently selected from the group consisting of H, $C_1$-$C_6$ alkyl or hydroxyl ($C_1$-$C_3$alkyl), providing that at least one of $R^1$ and $R^2$ is H;
$R^3$ is H;
$R^6$ and $R^7$ are each H;
$n_2$ is 2;
$R^4$ and $R^5$ are each independently selected from the group consisting of —$(CR^{28}R^{29})_{n1}$-G, where,
$n_1$ is 0-5; and G is
H, —$NR^{13}R^{14}$, —$NR^{12}C(O)R^{14}$, —$C(O)NR^{13}R^{14}$, —OC(O)$NR^{13}R^{14}$, $NR^{12}C(O)OR^{13}$, —$NR^{12}(C(O)NR^{13}R^{14})$, —$NR^{12}S)_2R^{13}$, $R^{19}$-heteroaryl, $R^{19}$-aryl, wherein heteroaryl is selected from the group consisting of pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazoyl, tetrazolyl, isothiazolyl, benzothiazolyl, benzoxazolyl, oxazolyl, pyrrolyl, isoxazolyl, 1,3,5-triazinyl or indolyl and aryl is selected from phenyl, —OH, —O($C_1$-$C_6$alkyl), —$C(OR^{12})(R^{13})$ ($R^{14}$), —$OC(O)R^{14}$, —$C(O)R^{13}$, heterocycloalkenyl optionally substituted by 1 substituent independently selected from the group consisting of $R^{30}$ and $R^{31}$,

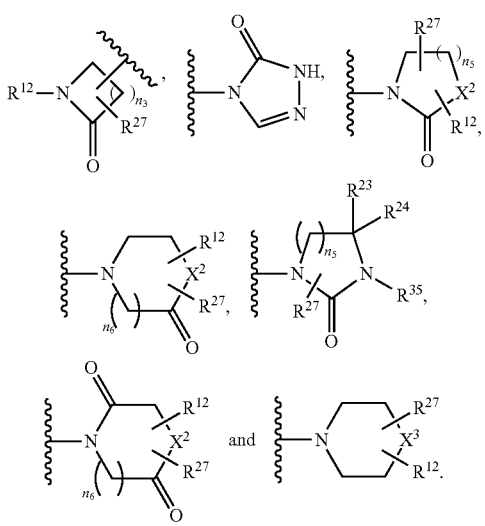

provided that R⁴ and R⁵ are not both selected from the group consisting of H, alkyl and cycloalkyl;
further provided that, when one of R⁴ and R⁵ is —OH, then the other one of R⁴ and R⁵ is not alkyl or (R$^{19}$aryl);

$R^{12}$ is H, $C_1$-$C_6$ alkyl or $C_3$-$C_8$ cycloalkyl;

$R^{13}$ and $R^{14}$ are reach independently selected from the group consisting of H, $C_1$-$C_6$alkyl, —CH$_2$CF$_3$, $C_3$-$C_6$ cycloalkyl, ($C_3$-$C_8$)cycloalkyl($C_1$-$C_6$)alkyl, phenyl or pyridinyl, pyrimidinyl, pyrazinyl, pyridazinyl, furanyl, benzofuranyl, thienyl, benzothienyl, thiazolyl, thiadiazolyl, imidazolyl, pyrazolyl, triazoyl, tetrazolyl, isothiazolyl, benzothiazolyl, benzoxazolyl, oxazolyl, pyrrolyl, isoxazolyl, 1,3,5-triazinyl or indolyl; or $R^{13}$ and $R^{14}$, together with the nitrogen atom to which they are both attached, form a 5- to 6-membered saturated or unsaturated ring that is optionally substituted with —OR$^{12}$, where one of the carbon atoms in the ring is optionally replaced by a heteroatom selected from —O—;

$n_6$ is 0, 1 or 2;

$R^{18}$ is H;

each $R^{19}$ is a substituent on the aryl or heteroaryl ring to which it is attached and is independently selected from the group consisting of H or $C_1$-$C_6$ alkyl;

$R^{23}$ and $R^{24}$ are each independently selected from the group consisting of H and $C_1$-$C_6$ alkyl; or $R^{23}$ and $R^{24}$, together with the carbon atom to which they are both attached, form a C=O or cyclopropyl group;

$R^{27}$ is H, —OH or $C_1$-$C_6$ alkyl;

$R^{28}$ and $R^{29}$ are each independently selected from the group consisting of H and $C_1$-$C_2$alkyl;

$R^{30}$ and $R^{31}$ are each independently selected from the group consisting of H, —OH, $C_1$-$C_6$ alkyl, $C_3$-$C_8$ cycloalkyl, ($C_3$-$C_8$)cycloalkyl($C_1$-$C_6$)alkyl and —C(0)NR$^{13}$R$^{14}$; or $R^{30}$ and $R^{31}$, together with the carbon atom to which they are both attached, form =O, =S, a cyclopropyl ring or =NR$^{36}$;

$R^{32}$ and $R^{33}$ are each H;

$R^{34}$ is H, $C_1$-$C_6$ alkyl, $C_3$-$C_8$ cycloalkyl, ($C_3$-$C_8$)cycloalkyl($C_1$-$C_6$)alkyl or hydroxyl($C_2$-$C_6$)alkyl;

$R^{35}$ is H, $C_1$-$C_6$ alkyl, $C_3$-$C_8$ cycloalkyl, ($C_3$-$C_8$)cycloalkyl($C_1$-$C_6$)alkyl, -P(0)(OH)$_2$, allyl, hydroxyl($C_2$-$C_6$)alkyl, ($C_1$-$C_6$)alkoxy($C_1$-$C_6$)alkyl, —SO$_2$R$^{15}$ or —(CH$_2$)$_2$—N(R$^{12}$)—SO$_2$—R$^{15}$;

$R^{36}$ is H, $C_1$-$C_6$ alkyl, $C_3$-$C_8$ cycloalkyl, ($C_3$-$C_8$)cycloalkyl($C_1$-$C_6$)alkyl, —NO$_2$, —CN or OR$^{12}$;

$R^{37}$ is 1 to 3 substituents independently selected from the group consisting of H, $C_1$-$C_6$ alkyl, —OH, $C_1$-$C_6$ alkoxy and halogen;

r is 1to 3;

$X^2$ is —NR$^{35}$—, —O—, —S—, —S(O)—, —S(O$_2$)—, —CH$_2$—, —CF$_2$— or —CR$^{12}$F—;

$X^3$ is —NR$^{34}$—, —N(CONR$^{13}$R$^{14}$)—, —N(CO$_2$R$^{15}$)—, —N(COR$^{12}$)—, —N(SO$_2$NHR$^{13}$)—, —O—, —S—, —S(O)—, SO$_2$—, —CH$_2$—, —CF$_2$—, or CR$^{12}$F—;

$n_3$ is 1 to 5; and $n_5$ is 1 to 3;

or a diastereomer, enantiomer, stereoisomer, regiostereomer, rotomer, or tautomer thereof.

2. The compound or salt according to claim 1 wherein R⁴ is —NR$^{13}$R$^{14}$, —NR$^{12}$C(O)R$^{14}$, NR$^{12}$C(O)OR$^{13}$, NR$^{12}$(C(O)NR$^{13}$R$^{14}$, —OH, —O—(C$_1$-C$_6$)alkyl, —O—(C$_3$-C$_8$cycloalkyl, —OC(O)R$^{14}$, —OC(O)NR$^{13}$R$^{14}$, —NR—SO$_2$NR$^{13}$R$^{14}$, R$^{19}$-heteroaryl,

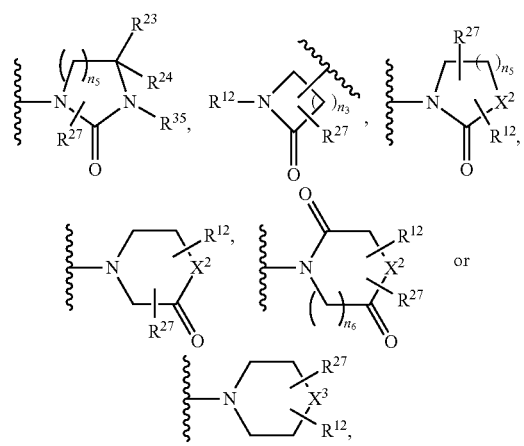

wherein X$_2$ is —O—, —S—, —CH$_2$— or —NR$^{35}$; and R⁵ is —C(O)OR$^{13}$ or —C(O)NR$^{13}$R$^{14}$.

3. The compound or salt according to claim 2 where R12 and R27 are independently selected from the group consisting of H and —CH3; n3 is 2 or 3; and n5 is 1 or 2.

4. the compound or salt according to claim 2, wherein R12 and R27 are H; n3 is 2 or 3; and n5 is 1 or 2.

5. A compound having the following structure:

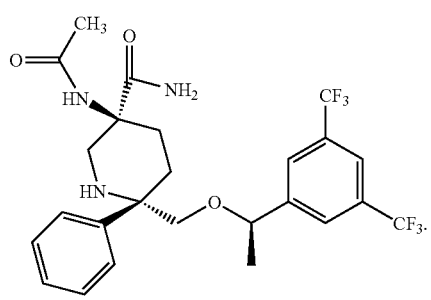

and pharmaceutically acceptable salts thereof.

6. A compound having the following structure:

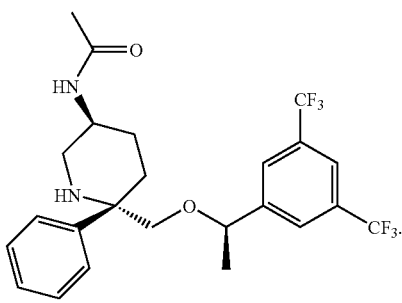

and pharmaceutically acceptable salts thereof.

7. A compound having the following structure:

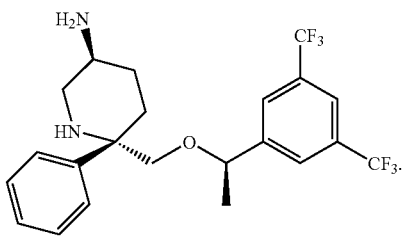

and pharmaceutically acceptable salts thereof.

8. The compound or salt according to claim 1, wherein the compound is:

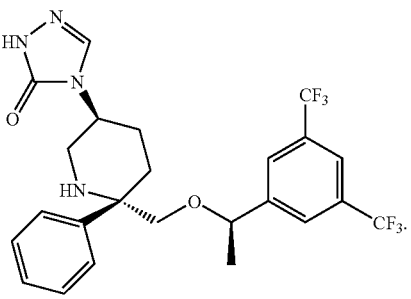

9. A pharmaceutical composition comprising a therapeutically effective amount of at least one compound of claim 1 in a pharmaceutically acceptable carrier.

10. The pharmaceutical composition according to claim 9, further comprising at least one serotonin reuptake inhibitor.

11. The pharmaceutical composition according to claim 9, further comprising at least one serotonin 5-HT3 receptor antagonist, or at least one corticosteroid or at least one substituted benzamide.

12. The pharmaceutical composition according to claim 9, further comprising at least one serotonin 5-HT3 receptor antagonist and at least one corticoid steroid.

13. The pharmaceutical composition according to claim 9, further comprising at least one substituted benzamide and at least one corticosteroid.

14. The pharmaceutical composition according to claim 10, where the selective serotonin reuptake inhibitor is fluoxetine, fluvoxamine, paroxetine, sertraline, or a pharmaceutically acceptable salt thereof.

15. The pharmaceutical composition according to claim 11, where the serotonin 5-HT3 receptor antagonist is ondansetron, dolasetron, palonsetron or granisetron, the corticosteroid is dexamethasone, and the substituted benzamide is metoclopramide.

16. The pharmaceutical composition according to claim 12 where the serotonin 5-HT3 receptor antagonist is ondansetron, dolasetron, palosetron or granisetron, the corticosteroid is dexamethasone.

17. The pharmaceutical composition according to claim 11, wherein the corticosteroid is dexamethasone, and the substituted benzamide is metoclopramide.

18. The pharmaceutical composition according to claim 13, where the corticosteroid is dexamethasone and the substituted benzamide is metoclopramide.

19. A compound selected from the group consisting of:

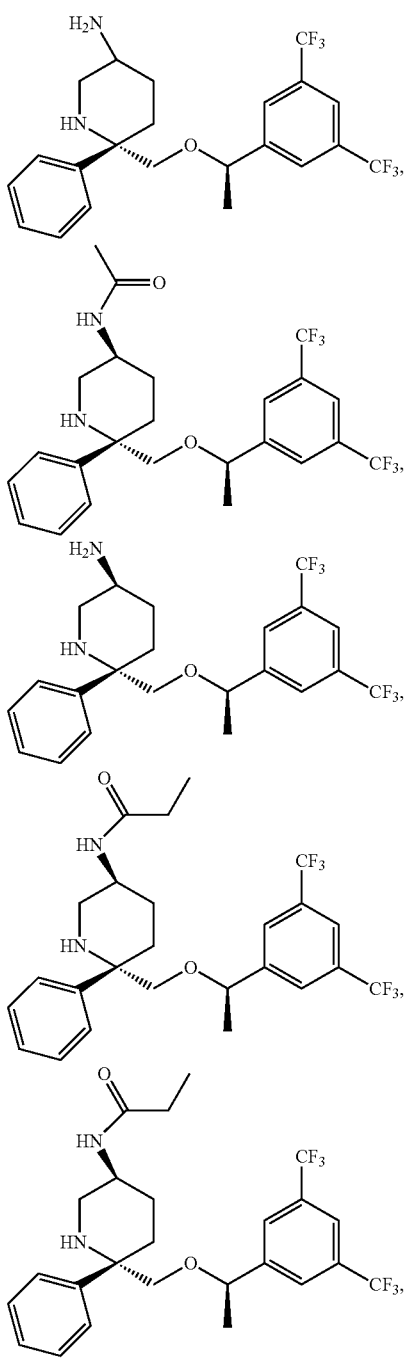

-continued
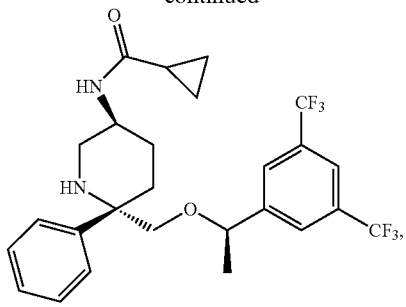
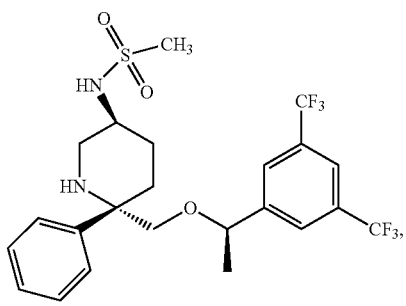
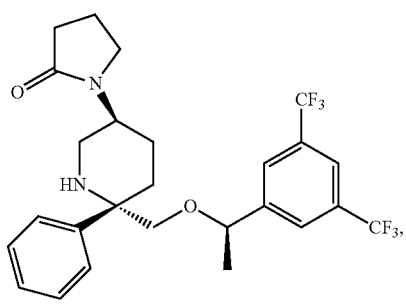
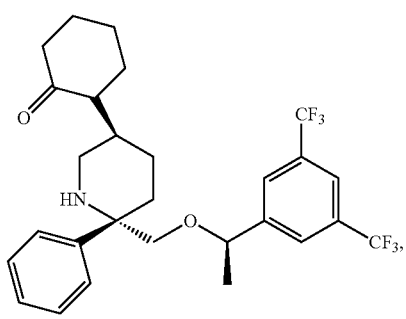
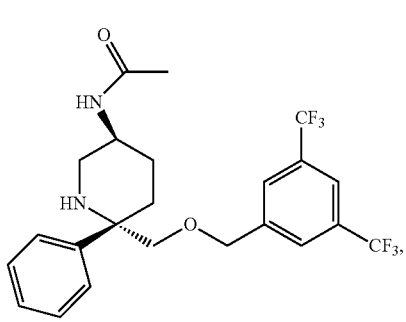
-continued
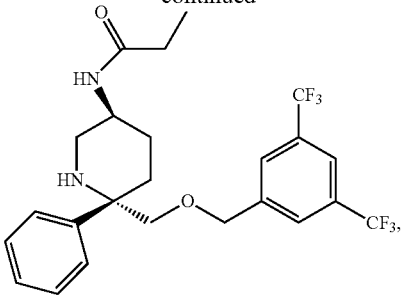
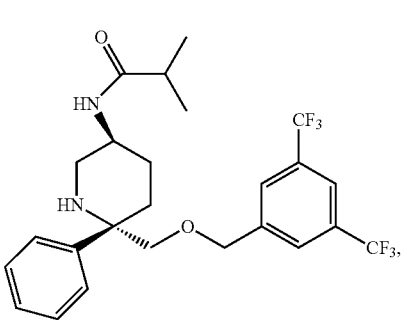
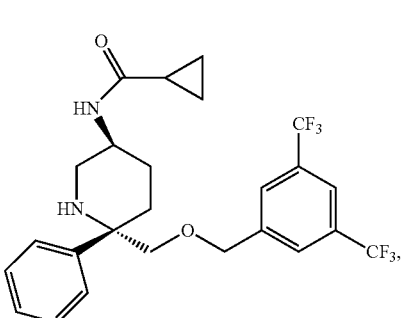
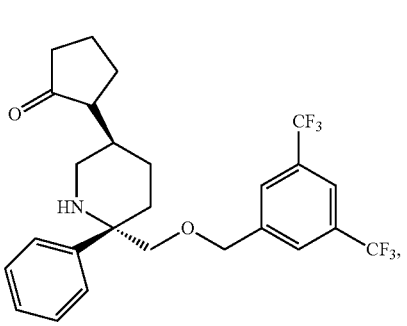
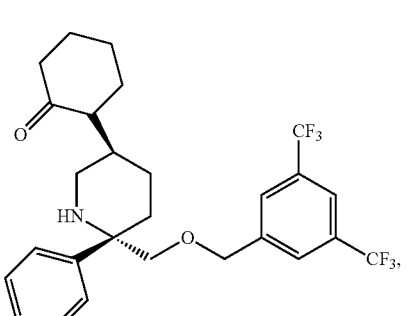

143
-continued
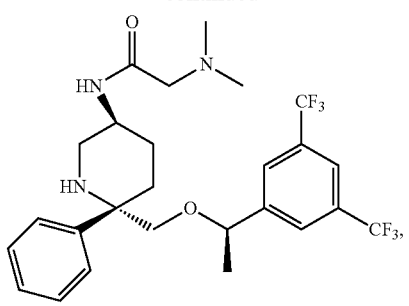
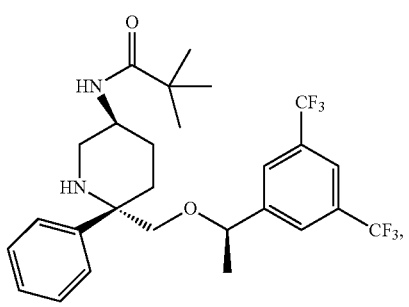
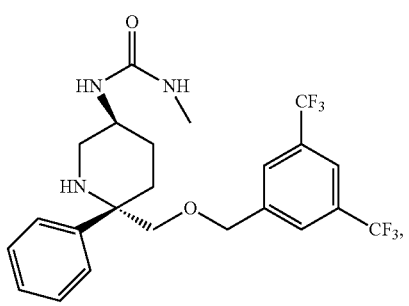
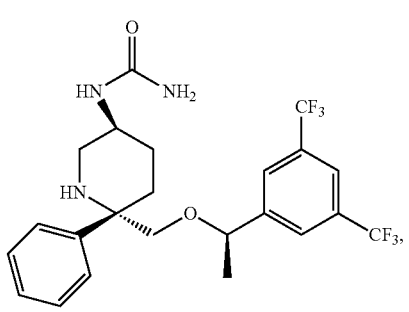
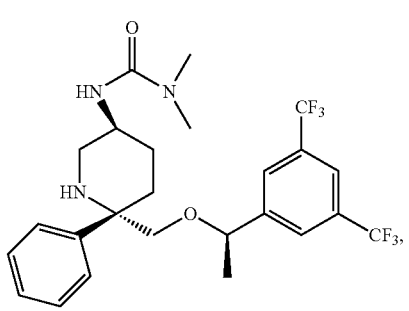
144
-continued
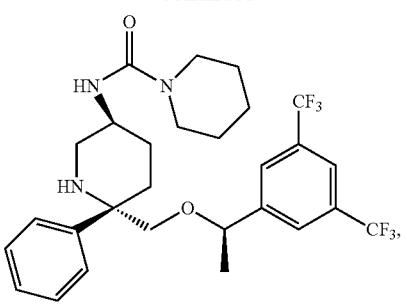
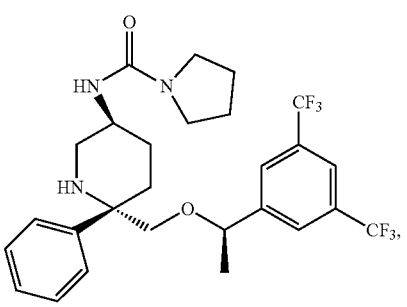
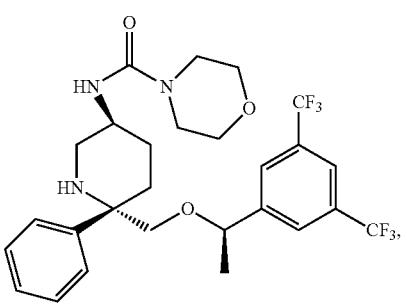
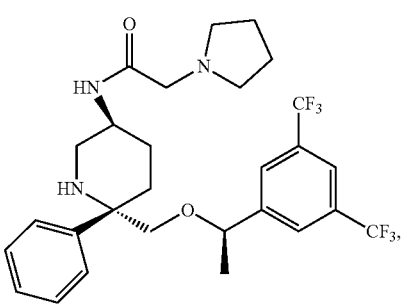
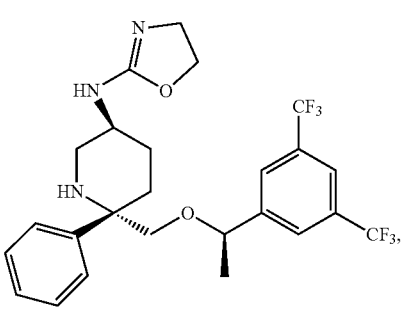

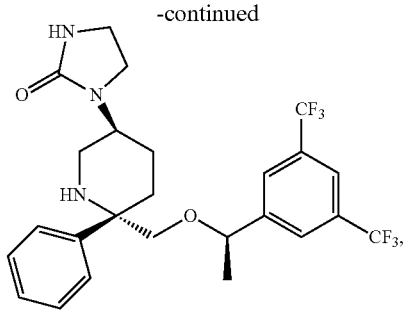
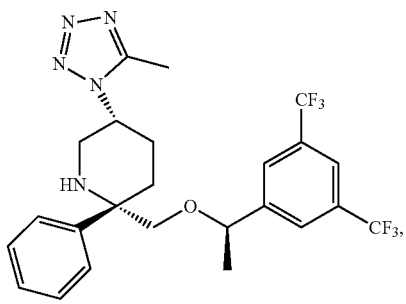
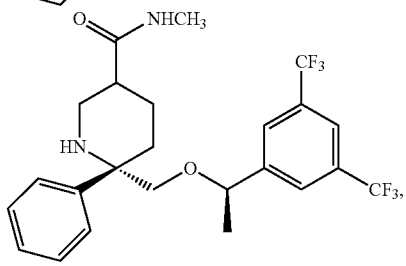
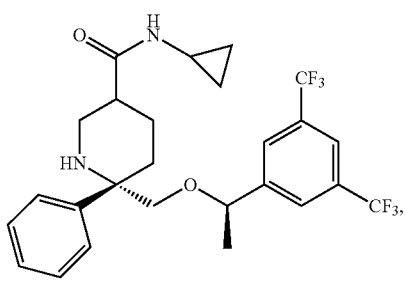
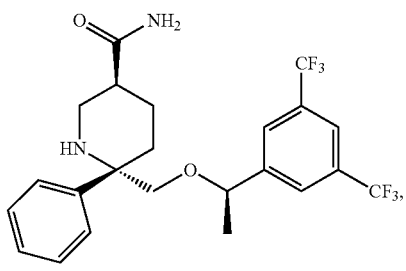
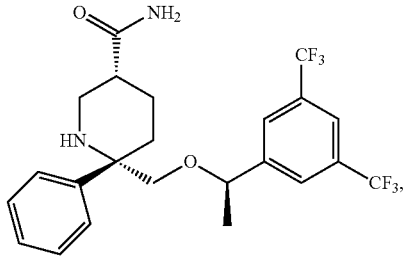
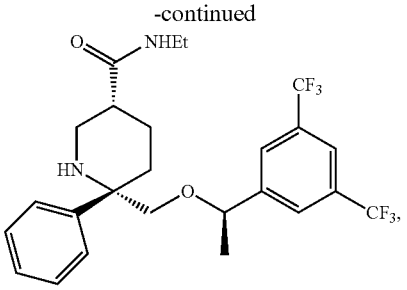
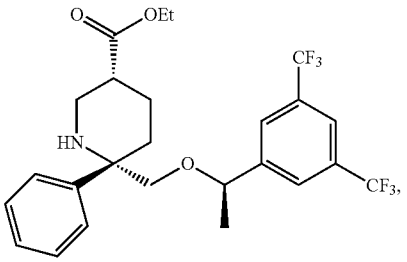
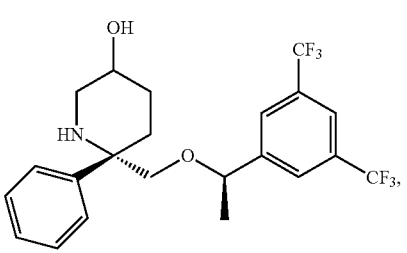
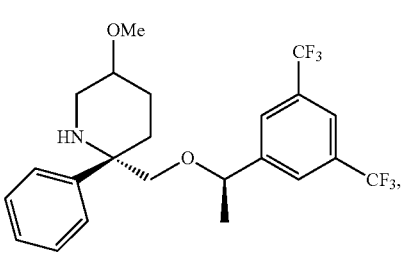
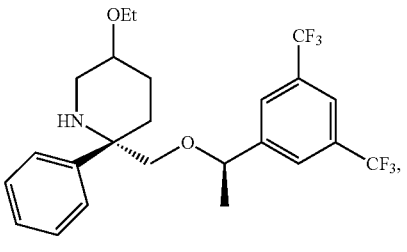
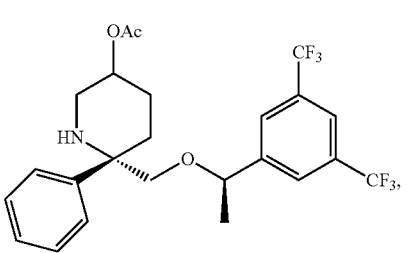

-continued
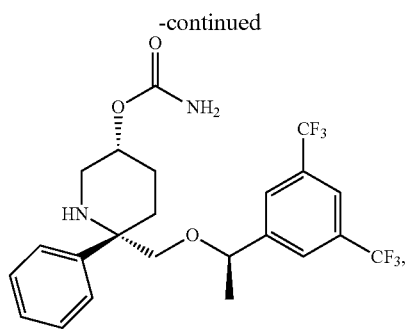
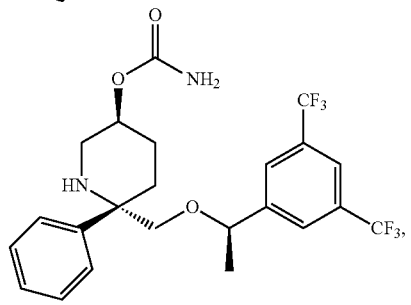
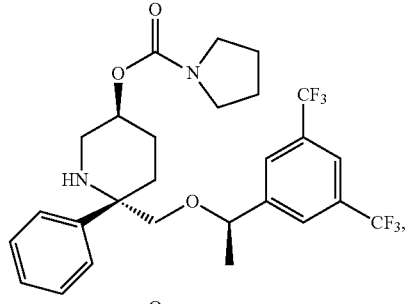
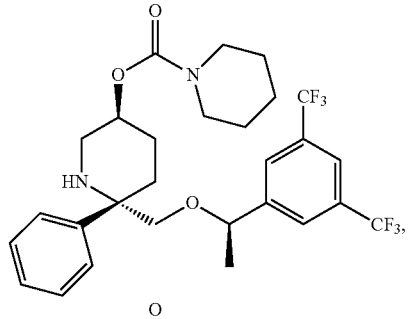
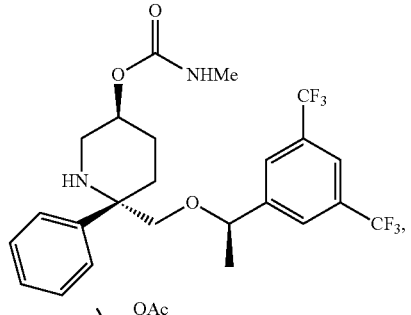
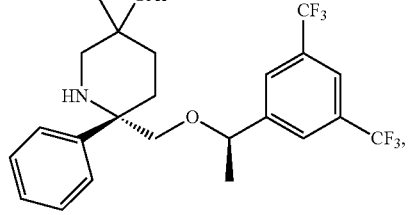
-continued
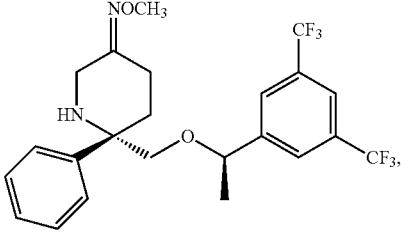
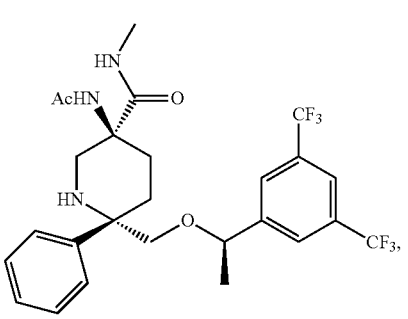
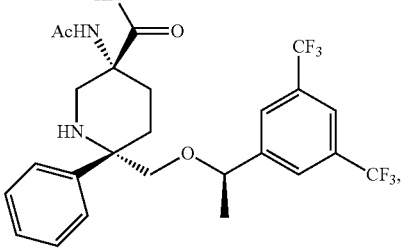
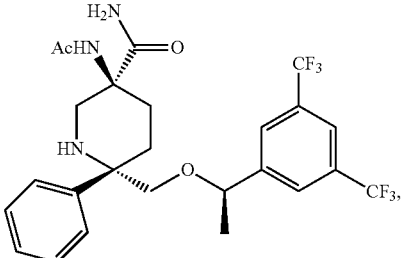
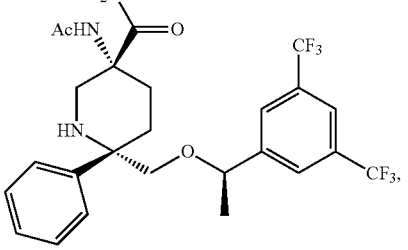

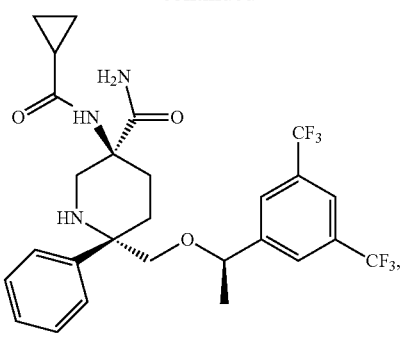
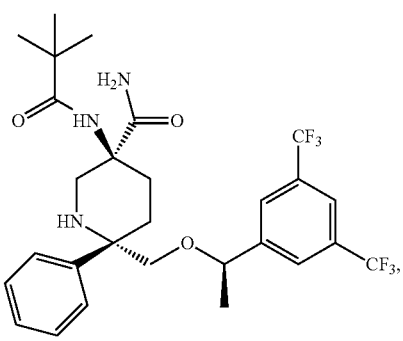
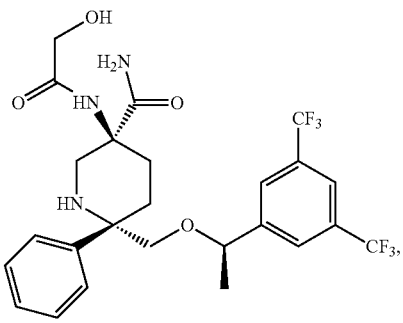
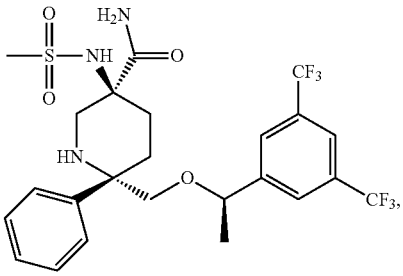
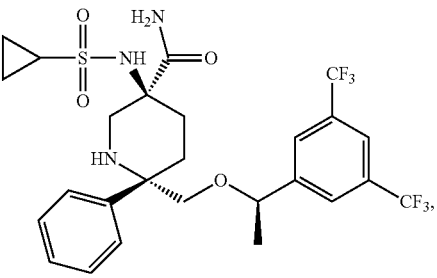
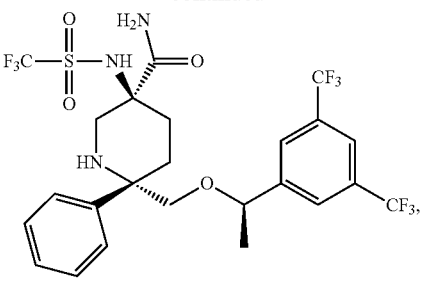
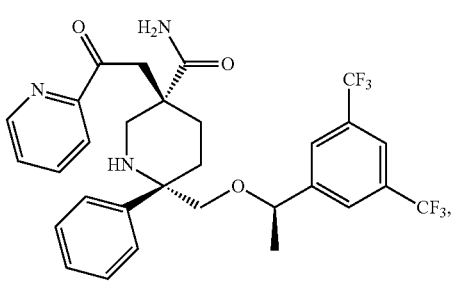
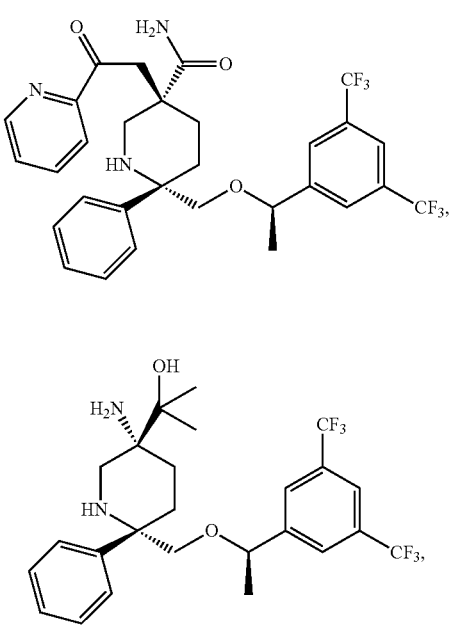
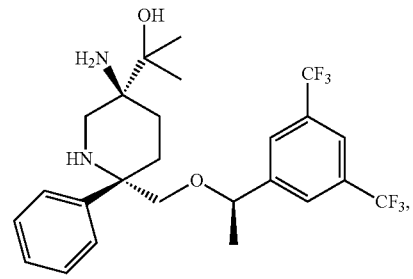
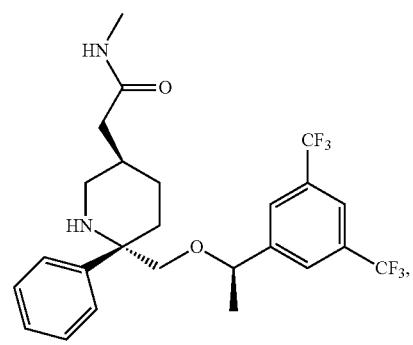

-continued
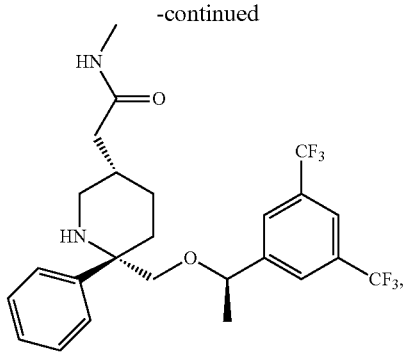
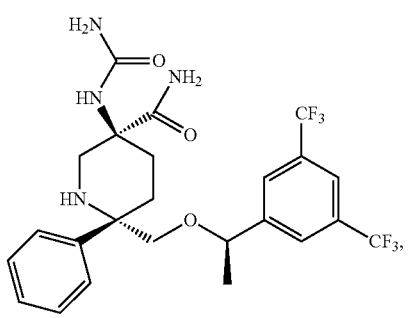
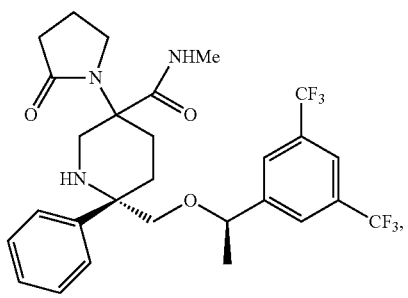
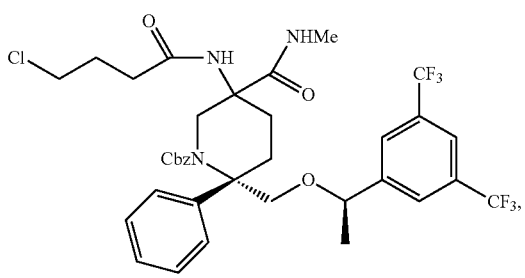
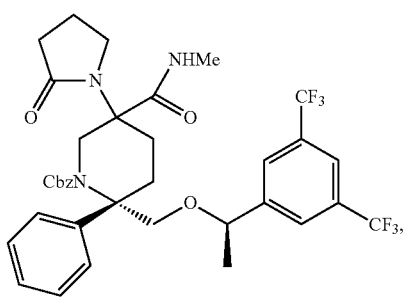
-continued
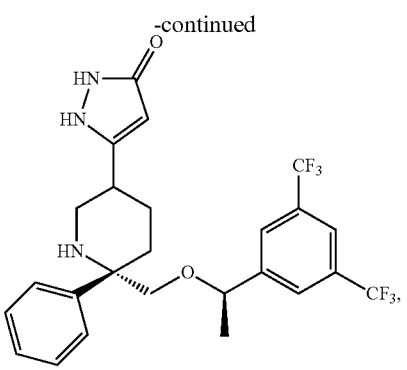
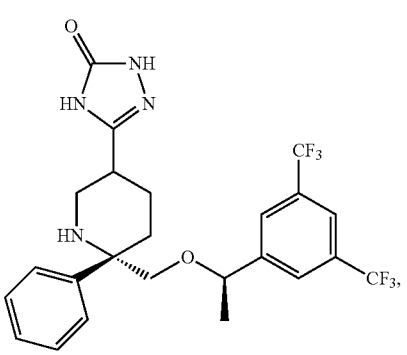
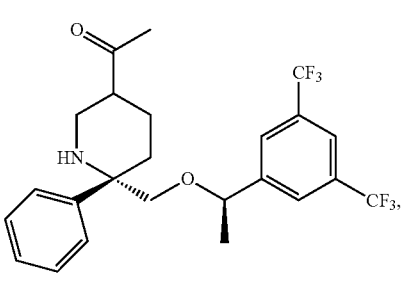
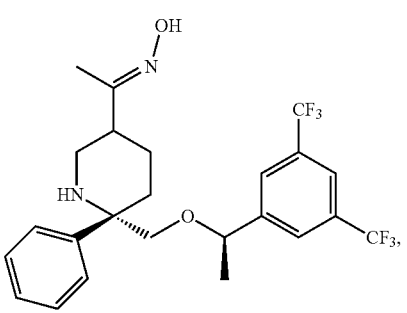
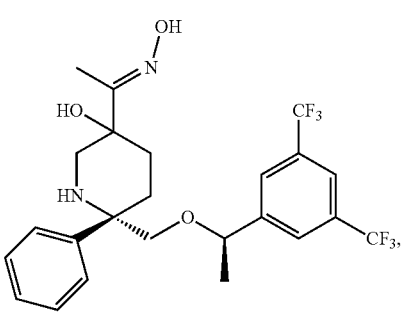

-continued
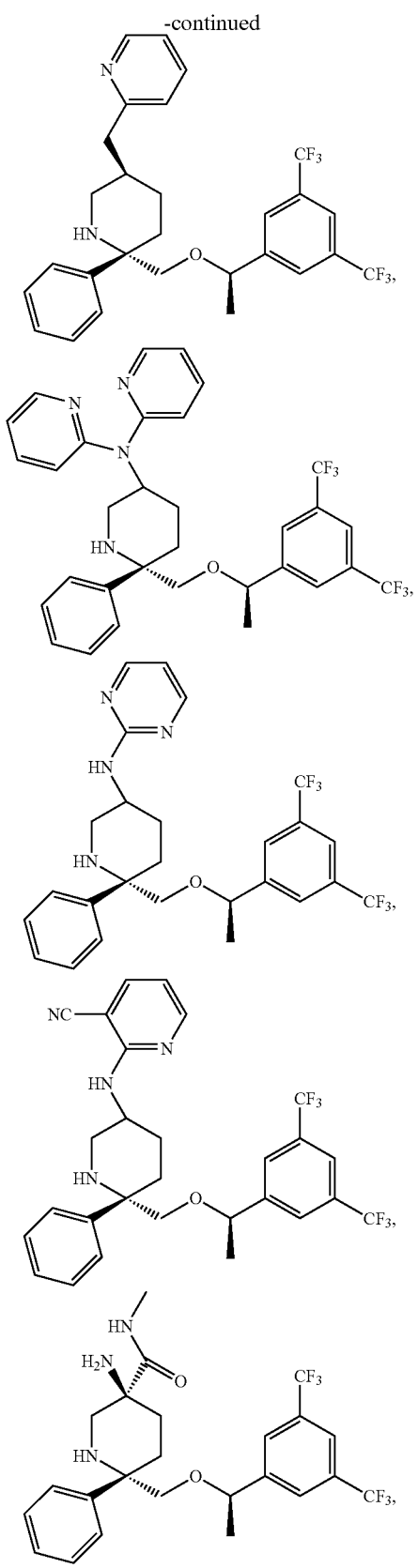
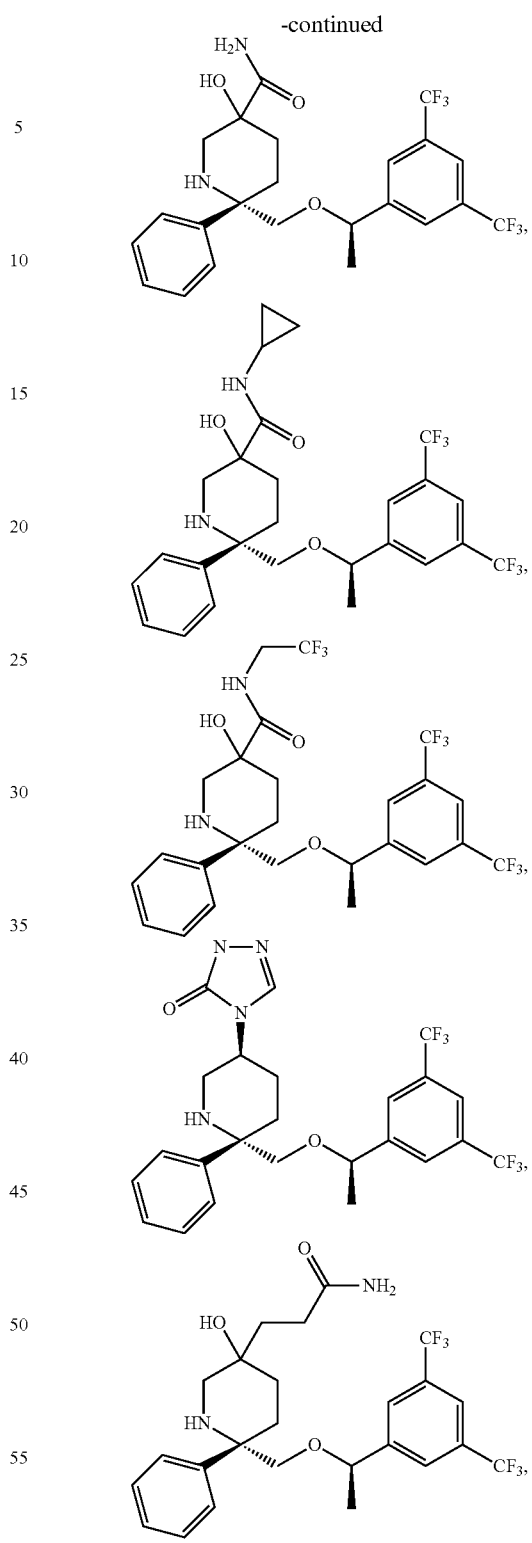
and pharmaceutically acceptable salts thereof.
* * * * *